US007439041B2

(12) United States Patent
Michelitsch et al.

(10) Patent No.: US 7,439,041 B2
(45) Date of Patent: Oct. 21, 2008

(54) PRION-SPECIFIC PEPTIDE REAGENTS

(75) Inventors: Melissa D. Michelitsch, Berkeley, CA (US); Celine Y-H. Hu, Tiburon, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 425 days.

(21) Appl. No.: 10/917,646

(22) Filed: Aug. 13, 2004

(65) Prior Publication Data

US 2005/0118645 A1 Jun. 2, 2005

Related U.S. Application Data

(60) Provisional application No. 60/586,509, filed on Jul. 9, 2004, provisional application No. 60/570,368, filed on May 12, 2004, provisional application No. 60/494,962, filed on Aug. 13, 2003.

(51) Int. Cl.
A61K 39/00 (2006.01)
C12N 15/00 (2006.01)
G01N 33/68 (2006.01)

(52) U.S. Cl. ............. 435/69.3; 424/184; 424/248.1
(58) Field of Classification Search ............ None
See application file for complete search history.

(56) References Cited

U.S. PATENT DOCUMENTS

| 6,211,149 | B1 | 4/2001 | Chesebro et al. ......... 514/12 |
| 6,372,214 | B1 | 4/2002 | Prusiner et al. |
| 6,462,171 | B1 | 10/2002 | Soto-Jara et al. ......... 530/326 |
| 6,656,716 | B1 * | 12/2003 | Plowman et al. ......... 435/194 |
| 6,680,170 | B2 * | 1/2004 | Plowman et al. ......... 435/6 |
| 6,765,088 | B1 | 7/2004 | Korth et al. ......... 530/388.1 |
| 2003/0166558 | A1 | 9/2003 | Frangione et al. ......... 514/12 |
| 2004/0186273 | A1 | 9/2004 | Hammond et al. ......... 530/325 |
| 2004/0208919 | A1 | 10/2004 | Nicolau et al. ......... 424/450 |
| 2005/0100962 | A1 | 5/2005 | van Oers et al. ......... 530/388 |
| 2006/0057671 | A1 | 3/2006 | Orser |

FOREIGN PATENT DOCUMENTS

| EP | 0 909 388 B1 | 9/2003 |
| EP | 1 457 500 A1 | 9/2004 |
| WO | WO 93/11155 | 6/1993 |
| WO | WO 93/23432 | 11/1993 |
| WO | WO 97/16728 | 5/1997 |
| WO | WO 99/15651 | 4/1999 |
| WO | WO 00/29849 A1 | 5/2000 |
| WO | WO 00/43791 A3 | 7/2000 |
| WO | WO 00/78344 A1 | 12/2000 |
| WO | WO 01/07479 A2 | 2/2001 |
| WO | WO 01/35104 A1 | 5/2001 |
| WO | WO 01/77687 A2 | 10/2001 |
| WO | WO 01/97785 A2 | 12/2001 |
| WO | WO 02/04954 A2 | 1/2002 |
| WO | WO 02/065134 A2 * | 8/2002 |
| WO | WO 02/097444 A2 | 12/2002 |
| WO | WO 03/045128 A2 | 6/2003 |
| WO | WO 03/050139 A3 | 6/2003 |
| WO | WO 03/073106 A3 | 9/2003 |
| WO | WO 03/085086 A2 | 10/2003 |
| WO | WO 2004/005920 A2 | 1/2004 |
| WO | WO 2004/018511 A3 | 3/2004 |
| WO | WO 2004/029072 A2 | 4/2004 |
| WO | WO 2004/091523 | 4/2004 |
| WO | WO 2004/037854 A1 | 5/2004 |
| WO | WO 2004/046728 A1 | 6/2004 |
| WO | WO 2004/050851 A2 | 6/2004 |
| WO | WO 2004/090102 A2 | 10/2004 |
| WO | WO 2006/026977 A2 | 3/2006 |

OTHER PUBLICATIONS

Bienkiewicz et al. J. Mo. Biol., 2000, vol. 297, p. 119-133.*
Lee et al. Cell, 1996, vol. 85, p. 931-942.*
Georgieva, Experimantal pathology and parasitology, 2002, p. 60-63.*
Coulthart et al. CMAJ, 2001, vol. 165, p. 51-58.*
Irani et al. Annu. rev. Med., 2003, vol. 54, p. 305-319.*
Koller et al., "Induction of antibodies against murine full-length prion protein in wild-type mice," Journal of Neuroimmunology 132:113-116 (2002).
Gasset et al., "Predicted α-Helical Regions of the Prion Protein When Synthesized as Peptides Form Amyloid" *Proc. Natl. Acad. Sci. USA* (1992) 89:10940-10944.
Nguyen et al., "Prion Protein Peptides Induce α-Helix to β-Sheet Conformational Transitions" *Biochemistry* (1995) 34:4186-4192.
Peretz et al., "A Conformational Transition at the N Terminus of the Prion Protein Features in Formation of the Scrapie Isoform" *J. Mol. Biol.* (1997) 273:614-622.
Peretz et al., "Antibodies Inhibit Prion Propagation and Clear Cell Cultures of Prion Infectivity" *Nature* (2001) 412:739-743.
Priola, "Prion Protein Diversity and Disease in the Transmissible Spongiform Encephalopathies" *Advances in Protein Chemistry* (2001) 57:1-27.
Ryou et al., "Differential Inhibition of Prion Propagation By Enantiomers of Quinacrine" *Laboratory Investigation* (2003) 83:837-843.
Tagliavini et al., "Synthetic Peptides Homologous to Prion Protein Residues 106-147 Form Amyloid-Like Fibrils in vitro" *Proc. Natl. Acad. Sci. USA* (1993) 90:9678-9682.
Tagliavini et al. "Studies on Peptide Fragments of Prion Proteins" *Advances in Protein Chemistry* (2001) 57:171-201.
Williamson et al., "Mapping the Prion Protein Using Recombinant Antibodies" *Journal of Virology* (1998) 72:9413-9418.

* cited by examiner

*Primary Examiner*—Bruce R. Campell
*Assistant Examiner*—Agnieszka Boesen
(74) *Attorney, Agent, or Firm*—Marcella Lillis; Dahna S. Pasternak

(57) ABSTRACT

Peptide reagents that interact preferentially with the $PrP^{sc}$ form of the prion protein are described. Methods of using the reagents or antibodies to the reagents for detection, diagnosis, purification, therapy and prophylaxis for prions and prion-associated diseases are also described.

32 Claims, 5 Drawing Sheets

FIGURE 1

PRION AMINO ACID SEQUENCES

Amino Acid Sequence of a Full Length Human Prion Protein:

SEQ ID NO. 1: M A N L G C W M L V L F V A T W S D L G L C K K
R P K P G G W N T G G S R Y P G Q G S P G G N R Y P P Q G G G G
W G Q P H G G G W G Q P H G G G W G Q P H G G G W G Q P H G
G G W G Q G G G T H S Q W N K P S K P K T N M K H M A G A A
A A G A V V G G L G G Y M L G S A M S R P I I H F G S D Y E D R
Y Y R E N M H R Y P N Q V Y Y R P M D E Y S N Q N N F V H D C
V N I T I K Q H T V T T T T K G E N F T E T D V K M M E R V V E
Q M C I T Q Y E R E S Q A Y Y Q R G S S M V L F S S P P V I L L I S
F L I F L I V G

Amino Acid Sequence of a Full Length Mouse Prion Protein:

SEQ ID. NO. 2: M A N L G Y W L L A L F V T M W T D V G L C K
K R P K P G G W N T G G S R Y P G Q G S P G G N R Y P P Q G G T
W G Q P H G G G W G Q P H G G S W G Q P H G G S W G Q P H G
G G W G Q G G G T H N Q W N K P S K P K T N L K H V A G A A A
A G A V V G G L G G Y M L G S A M S R P M I H F G N D W E D R
Y Y R E N M Y R Y P N Q V Y Y R P V D Q Y S N Q N N F V H D C
V N I T I K Q H T V T T T T K G E N F T E T D V K M M E R V V E
Q M C V T Q Y Q K E S Q A Y Y D G R R S S S T V L F S S P P V I L
L I S F L I F L I V G

FIGURE 2

```
Human    --MANLGCWMLVLFVATWSDLGLCKKRPKPGG-WNTGGSRYPGQGSPGGNRYPPQGGGGW
Hamster  --MANLSYWLLALFVAMWTDVGLCKKRPKPGG-WNTGGSRYPGQGSPGGNRYPPQGGGTW
Bovine   MVKSHIGSWILVLFVAMWSDVGLCKKRPKPGGGWNTGGSRYPGQGXPGGNRYPPQGGGGW
Sheep    MVKSHIGSWILVLFVAMWSDVGLCKKRPKPGGGWNTGGSRYPGQGSPGGNRYPPQGGGGW
Mouse    --MANLGYWLLALFVTMWTDVGLCKKRPKPGG-WNTGGSRYPGQGSPGGNRYPPQGG-TW
Elk      MVKSHIGSWILVLFVAMWSDVGLCKKRPKPGGGWNTGGSRYPGQGSPGGNRYPPQGGGGW
Fallow   MVKSHIGSWILVLFVAMWSDVGLCKKRPKPGGGWNTGGSRYPGQGSPGGNRYPPQGGGGW
Mule     MVKSHIGSWILVLFVAMWSDVGLCKKRPKPGGGWNTGGSRYPGQGSPGGNRYPPQGGGGW
White    MVKSHIGSWILVLFVAMWSDVGLCKKRPKPGGGWNTGGSRYPGQGSPGGNRYPPQGGGGW
          ::: . *:*.***: *:*:*********** ************ *********** *

Human    GQPHGGGWGQPHGGGWGQPHGG--------GWGQPHGGG-WGQGGGTHSQWNKPSKPKTN
Hamster  GQPHGGGWGQPHGGGWGQPHGG--------GWGQPHGGG-WGQGGGTHNQWNKPSKPKTN
Bovine   GQPHGGGWGQPHGGGWGQPHGGGWGQPHGGGWGQPHGGGGWGQGG-THGQWNKPSKPKTN
Sheep    GQPHGGGWGQPHGGGWGQPHGG--------GWGQPHGGGGWGQGG-SHSQWNKPSKPKTN
Mouse    GQPHGGGWGQPHGGSWGQPHGG--------SWGQPHGGG-WGQGGGTHNQWNKPSKPKTN
Elk      GQPHGGGWGQPHGGGWGQPHGG--------GWGQPHGGGGWGQGG-THSQWNKPSKPKTN
Fallow   GQPHGGGWGQPHGGGWGQPHGG--------GWGQPHGGGGWGQGG-THSQWNKPSKPKTN
Mule     GQPHGGGWGQPHGGGWGQPHGG--------GWGQPHGGGGWGQGG-THSQWNKPSKPKTN
White    GQPHGGGWGQPHGGGWGQPHGG--------GWGQPHGGGGWGQGG-THSQWNKPSKPKTN
         ***************.*******         .******* ***** :*.**********

Human    MKHMAGAAAAGAVVGGLGGYMLGSAMSRPIIHFGSDYEDRYYRENMHRYPNQVYYRPMDE
Hamster  MKHMAGAAAAGAVVGGLGGYMLGSAMSRPMMHFGNDWEDRYYRENMNRYPNQVYYRPVDQ
Bovine   MKHVAGAAAAGAVVGGLGGYMLGSAMSRPLIHFGXDYEDRYYRENMHRYPNQVYYRPVDQ
Sheep    MKHVAGAAAAGAVVGGLGGYMLGSAMSRPLIHFGNDYEDRYYRENMYRYPNQVYYRPVDR
Mouse    LKHVAGAAAAGAVVGGLGGYMLGSAMSRPMIHFGNDWEDRYYRENMYRYPNQVYYRPVDQ
Elk      MKHVAGAAAAGAVVGGLGGYMLGSAMSRPLIHFGNDYEDRYYRENMYRYPNQVYYRPVDQ
Fallow   MKHVAGAAAAGAVVGGLGGYMLGSAMNRPLIHFGNDYEDRYYRENMYRYPNQVYYRPVDQ
Mule     MKHVAGAAAAGAVVGGLGGYMLGSAMSRPLIHFGNDYEDRYYRENMYRYPNQVYYRPVDQ
White    MKHVAGAAAAGAVVGGLGGYMLGSAMSRPLIHFGNDYEDRYYRENMYRYPNQVYYRPVDQ
         :**:*******************.**::*** *:********* **********:*.

Human    YSNQNNFVHDCVNITIKQHTVTTTTKGENFTETDVKMMERVVEQMCITQYERESQAYYQ-
Hamster  YNNQNNFVHDCVNITIKQHTVTTTTKGENFTETDIKIMERVVEQMCTTQYQKESQAYYDG
Bovine   YSNQNNFVHDCVNITVKEHTVTTTTKGENFTETDIKMMERVVEQMCITQYQRESQAYYQ-
Sheep    YSNQNNFVHDCVNITVKQHTVTTTTKGENFTETDIKIMERVVEQMCITQYQRESQAYYQ-
Mouse    YSNQNNFVHDCVNITIKQHTVTTTTKGENFTETDVKMMERVVEQMCVTQYQKESQAYYDG
Elk      YNNQNTFVHDCVNITVKQHTVTTTTKGENFTETDIKMMERVVEQMCITQYQRESEAYYQ-
Fallow   YNNQNTFVHDCVNITVKQHTVTTTTKGENFTETDIKMMERVVEQMCITQYQRESEAYYQ-
Mule     YNNQNTFVHDCVNITVKQHTVTTTTKGENFTETDIKMMERVVEQMCITQYQRESQAYYQ-
White    YNNQNTFVHDCVNITVKQHTVTTTTKGENFTETDIKMMERVVEQMCITQYQRESQAYYQ-
         *.***.*********:*:***************:*:********* ***::**:***:

Human    -RGSSMVLFSSPPVILLISFLIFLIVG    (SEQ ID NO:3)
Hamster  RRSS-AVLFSSPPVILLISFLIFLMVG    (SEQ ID NO:4)
Bovine   -RGASVILFSSPPVILLISFLIFLIVG    (SEQ ID NO:5)
Sheep    -RGASVILFSSPPVILLISFLIFLIVG    (SEQ ID NO:6)
Mouse    RRSSSTVLFSSPPVILLISFLIFLIVG    (SEQ ID NO:7)
Elk      -RGASVILFSSPPVILLISFLIFLIVG    (SEQ ID NO:8)
Fallow   -RGASVILFSSPPVILLISFLIFLIVG    (SEQ ID NO:9)
Mule     -RGASVILFSSPPVILLISFLIFLIVG    (SEQ ID NO:10)
White    -RGASVILFSSPPVILLISFLIFLIVG    (SEQ ID NO:11)
```

FIGURE 3
(A)
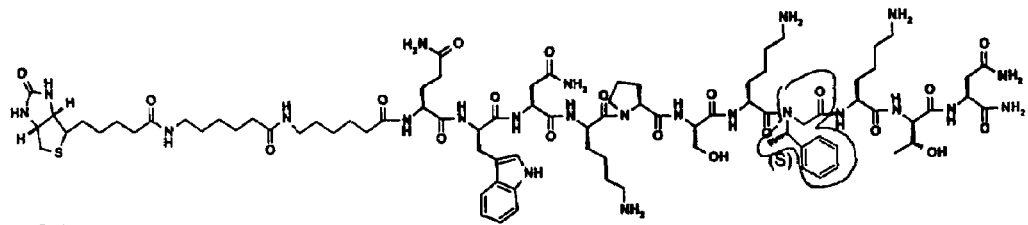
(B)
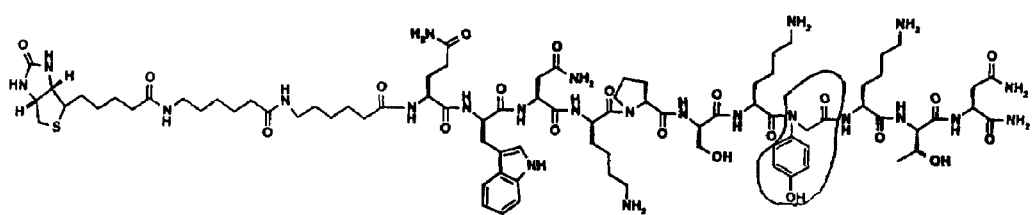
(C)
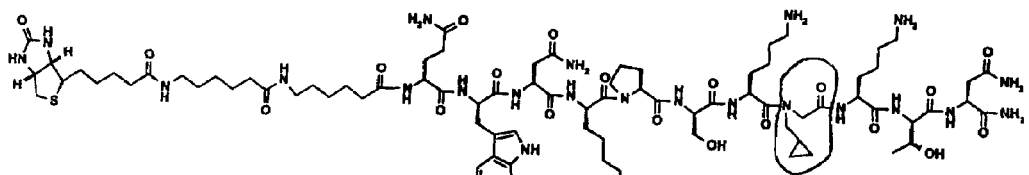
(D)
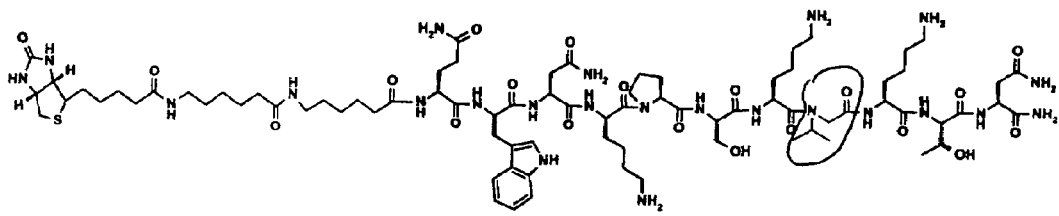
(E)
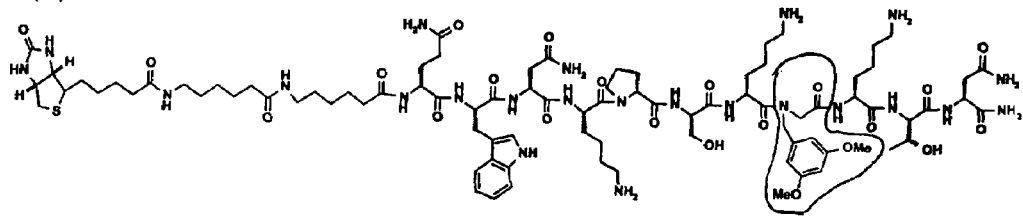
(F)
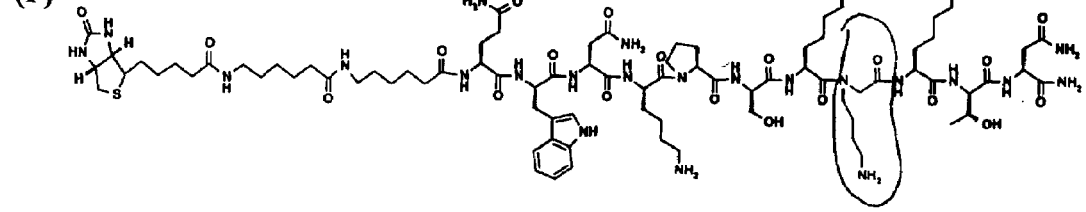

FIGURE 4: Peptide Specificity for PrPSc In Human Plasma and Mouse Brain

PRION-SPECIFIC PEPTIDE REAGENTS

FIELD OF THE INVENTION

The invention relates to peptide reagents that interact with prion proteins, polynucleotides encoding these peptide reagents, methods of generating antibodies using such peptide reagents and polynucleotides, and to antibodies generated using these methods. The invention further relates to methods of using these peptide reagents to detect the presence of pathogenic prions in a sample and to methods of using these peptide reagents as components in a therapeutic or prophylactic composition.

BACKGROUND

Protein conformational diseases include a variety of unrelated diseases, including transmissible spongiform encephalopathies, arising from aberrant conformational transition of a protein (a conformational disease protein) which in turn leads to self-association of the aberrant protein forms, with consequent tissue deposition and damage. These diseases also share striking similarities in clinical presentations, typically a rapid progression from diagnosis to death following varying lengths of incubation.

One group of conformational diseases are termed "prion diseases" or "transmissible spongiform encephalopathies (TSEs)." In humans these diseases include Creutzfeldt-Jakob disease (CJD), Gerstmann-Straussler-Scheinker syndrome (GSS), Fatal Familial Insomnia, and Kuru (see, e.g., Harrison's Principles of Internal Medicine, Isselbacher et al., eds., McGraw-Hill, Inc. New York, (1994); Medori et al. (1992) *N. Engl. J. Med.* 326: 444-9.). In animals the TSE's include sheep scrapie, bovine spongiform encephalopathy (BSE), transmissible mink encephalopathy, and chronic wasting disease of captive mule deer and elk (Gajdusek, (1990) Subacute Spongiform Encephalopathies: Transmissible Cerebral Amyloidoses Caused by Unconventional Viruses. Pp. 2289-2324 In: Virology, Fields, ed. New York: Raven Press, Ltd.). Transmissible spongiform encephalopathies are characterized by the same hallmarks: the presence of the abnormal (beta-rich, proteinase K resistant) conformation of the prion protein that transmits disease when experimentally inoculated into laboratory animals including primates, rodents, and transgenic mice.

Recently, the rapid spread of bovine spongiform encephalopathy and its correlation with elevated occurrence of spongiform encephalopathies in humans has lead to a significant increase of interest in the detection of transmissible spongiform encephalopathies in non-human mammals. The tragic consequences of accidental transmission of these diseases (see, e.g., Gajdusek, Infectious Amyloids, and Prusiner Prions In Fields Virology. Fields, et al., eds. Lippincott-Ravin, Pub. Philadelphia (1996); Brown et al. (1992) Lancet, 340: 24-27), decontamination difficulties (Asher et al. (1986) pages 59-71 In: Laboratory Safety: Principles and Practices, Miller ed. Am. Soc. Microb.), and recent concern about bovine spongiform encephalopathy (British Med. J. (1995) 311: 1415-1421) underlie the urgency of having both a diagnostic test that would identify humans and animals with transmissible spongiform encephalopathies and therapies for infected subjects.

Prions are the infectious pathogen that causes spongiform encephalopathies (prion diseases). Prions differ significantly from bacteria, viruses and viroids. The dominating hypothesis is that, unlike all other infectious pathogens, infection is caused by an abnormal conformation of the prion protein, which acts as a template and converts normal prion conformations into abnormal conformations. A prion protein was first characterized in the early 1980s. (See, e.g., Bolton, McKinley et al. (1982) Science 218:1309-1311; Prusiner, Bolton et al. (1982) Biochemistry 21:6942-6950; McKinley, Bolton et al. (1983) Cell 35:57-62). Complete prion protein-encoding genes have since been cloned, sequenced and expressed in transgenic animals. See, e.g., Basler, Oesch et al. (1986) Cell 46:417-428.

The key characteristic of prion diseases is the formation of an abnormally shaped protein ($PrP^{Sc}$), also referred to as a scrapie protein, from the normal (cellular or nonpathogenic) form of prion protein ($PrP^C$). See, e.g., Zhang et al. (1997) *Biochem.* 36(12):3543-3553; Cohen & Prusiner (1998) *Ann Rev. Biochem.* 67:793-819; Pan et al. (1993) Proc Natl Acad Sci USA 90:10962-10966; Safar et al. (1993) J Biol Chem 268:20276-20284. Optical spectroscopy and crystallography studies have revealed that disease-related forms of prions are substantially enriched in beta-sheet structure as compared to the predominantly alpha-helical folded non-disease forms. See, e.g., Wille et al. (2001) *Proc. Nat'l Acad. Sci. USA* 99:3563-3568; Peretz et al. (1997) *J. Mol. Biol.* 273:614-622; Cohen & Prusiner, Chapter 5: Structural Studies of Prion Proteins in PRION BIOLOGY AND DISEASES, ed. S. Prusiner, Cold Spring Harbor Laboratory Press, 1999, pp: 191-228). The structural changes appear to be followed by alterations in the biochemical properties: $PrP^C$ is soluble in non-denaturing detergents, $PrP^{Sc}$ is insoluble; $PrP^C$ is readily digested by proteases, while $PrP^{Sc}$ is partially resistant, resulting in the formation of an N-terminally truncated fragment known as "PrPres" (Baldwin et al. (1995); Cohen & Prusiner (1995)), "PrP 27-30" (27-30 kDa) or "PK-resistant" (proteinase K resistant) form. In addition, $PrP^{Sc}$ can convert $PrP^C$ to the pathogenic conformation. See, e.g., Kaneko et al. (1995) *Proc. Nat'l Acad. Sci. USA* 92:11160-11164; Caughey (2003) *Br Med Bull.* 66:109-20.

Detection of the pathogenic isoforms of conformational disease proteins in living subjects and samples obtained from living subjects has proven difficult. Thus, definitive diagnosis and palliative treatments for these transmissible and amyloid containing conditions before death of the subject remains a substantially unmet challenge. Histopathological examination of brain biopsies is risky to the subject and lesions and amyloid deposits can be missed depending on where the biopsy sample is taken from. However, there are still risks involved with biopsies to animals, patients, and health care personnel. Further, the results from brain tests on animals are not usually obtained until the animal has entered the food supply. In addition, antibodies generated against prion peptides recognize both denatured $PrP^{Sc}$ and $PrP^C$ but are unable to selectively recognize infectious (undenatured) $PrP^{Sc}$. (See, e.g., Matsunaga et al. (2001) PROTEINS: Structure, Function and Genetics 44:110-118).

Thus, there remains a need for compositions and methods for detecting the presence of pathogenic prion proteins in various samples, for example in samples obtained from living subjects, in blood supplies, in farm animals and in other human and animal food supplies. In addition, there remains a need for methods and compositions for diagnosing and treating prion-related diseases.

SUMMARY OF THE INVENTION

The present invention relates, in part, to peptide reagents that interact with prion proteins. More specifically, the peptide reagents described herein interact preferentially with the pathogenic isoforms of prion proteins. These peptide reagents can be used in a wide range of applications, including as tools to isolate pathogenic prions or to detect the presence of pathogenic prions in a sample, as components of a therapeutic or prophylactic composition and/or to generate prion-specific antibodies. For example, peptide reagents that interact preferentially with PrP$^{Sc}$ as compared to PrP$^C$ are useful for direct detection of pathogenic forms in samples obtained from living subjects, for example, for diagnosis of a disease or for screening donated blood samples or screening organs for organ donation.

In a broader aspect, the invention includes a peptide reagent that interacts preferentially with pathogenic forms of a conformational disease protein. In certain embodiments, the peptide reagents described herein interact preferentially with pathogenic forms of a prion protein as compared to nonpathogenic forms of the prion protein. The peptide reagents described herein may be partially or fully synthetic, for example, may comprise one or more the following moieties: cyclized residues or peptides, multimers of peptides, labels, and/or other chemical moieties. Examples of suitable peptide reagents include those derived from peptides of SEQ ID NOs: 12-132, for example, peptides such as those depicted in SEQ ID NOs: 66, 67, 68, 72, 81, 96, 97, 98, 107, 108, 119, 120, 121, 122, 123, 124, 125, 126, 127, 14, 35, 36, 37, 40, 50, 51, 77, 89, 100, 101, 109, 110, 111, 112, 113, 114, 115, 116, 117, 118, 128, 129, 130, 131, 132, 56, 57, 65, 82, or 84, and analogs and derivatives thereof. The peptide reagents described herein may interact with any conformational disease proteins, for example, prion proteins (e.g., the pathogenic protein PrP$^{Sc}$, and the nonpathogenic form PrP$^C$). In certain embodiments, peptide reagents interact preferentially with PrP$^{Sc}$ as compared to PrP$^C$. The peptide reagents will generally be specific for PrP$^{Sc}$ from more than one species, but may be specific for PrP$^{Sc}$ from a single species.

In another embodiment, peptide reagents derived from peptides shown in any of sequence described herein are provided. In certain embodiments, the peptide reagents are derived from regions of a prion protein, for example, those regions corresponding to residues 23-43 or 85-156 (e.g., 23-30, 86-111, 89-112, 97-107, 113-135, and 136-156 numbered according to the mouse prion sequence shown in SEQ ID NO:2) are employed. For convenience, the amino acid residue numbers set out above are those corresponding to the mouse prion protein sequence in SEQ ID NO:2; one of ordinary skill in the art could readily identify corresponding regions in prion proteins of other species based on the sequences known in the art and the teachings provided herein. Exemplary peptide reagents include those derived from peptides having SEQ ID NO: 66, 67, 68, 72, 81, 96, 97, 98, 107, 108, 119, 120, 121, 122, 123, 124, 125, 126, or 127; or from peptides having SEQ ID NO: 14, 35, 36, 37, 40, 50, 51, 77, 89, 100, 101, 109, 110, 111, 112, 113, 114, 115, 116, 117, 118, 129, 130, 131, 132 or 128; or from peptides having SEQ ID NO: 56, 57, 65, 82, or 84.

In another aspect, the invention includes a complex comprising one or more of the peptide reagents described herein and a prion protein.

In another aspect, a method of generating antibodies that recognize prion proteins is provided, the method comprising the step of administering any of the peptide reagents described herein (or polynucleotides encoding the peptide reagents) to a subject (e.g., animal). In certain embodiments, the method further comprises the step of isolating antibodies from the animal. A related aspect of the invention includes antibodies made by the method. Preferred antibodies are specific for the pathogenic form.

In yet another aspect, the invention includes a complex comprising any of the antibodies described herein and a prion protein. In certain embodiments, the prion protein is a nonpathogenic isoform while in other embodiments it is a pathogenic isoform.

Any of the peptide reagents and/or antibodies described herein may be encoded for, in whole or in part, by one or more polynucleotides, which also form part of the present invention.

In yet another aspect, methods for detecting the presence of prion proteins are provided. The detection methods may be used, inter alia, in connection with methods for diagnosing a prion-related disease (e.g., in human or non-human animal subjects), ensuring a substantially PrP$^{Sc}$-free blood supply, blood products supply, or food supply, analyzing organ and tissue samples for transplantation, monitoring the decontamination of surgical tools and equipment, as well as any other situation in which knowledge of the the presence or absence of the pathogenic prion is important.

The detection methods rely on the preferential interaction of the peptide reagents of the invention with the pathogenic prion isoform. In certain embodiments, a method for detecting the presence of a pathogenic prion in a biological sample is provided.

In one embodiment, the method comprises contacting the sample suspected of containing a pathogenic prion with one or more of the peptide reagents described herein under conditions that allow the interaction of the peptide reagent(s) and the pathogenic prion, if present; and detecting the presence or absence of the pathogenic prion in the sample by its binding to the peptide reagent(s). The interaction of the peptide reagent(s) and the pathogenic prion can be carried out in solution, or one or more of the reactants can be provided in or on a solid phase. Sandwich-type assays can be carried out in which the peptide reagents of the invention can be used as a capture reagent, a detection reagent or both. Other prion-binding reagents (e.g., antibodies and other binding molecules that bind to denatured prion protein) may be used in this aspect in combination with the peptide reagents of the invention.

In one aspect of this embodiment, one or more peptide reagents of the present invention is provided on a solid support and contacted with a sample suspected of containing a pathogenic prion, under conditions that allow binding of the pathogenic prion, if present, to the peptide reagent. Unbound sample materials, including any non-pathogenic prion, can be removed and the pathogenic prion can be detected, either while remaining bound to the peptide reagent or after dissociation from the peptide reagent. The pathogenic prion can be detected using a detectably labeled peptide reagent (either the same peptide reagent used to "capture" the pathogenic prion or a second peptide reagent of the invention) or a detectably labeled anti-prion antibody or other prion-binding reagent. This antibody or prion-binding reagent need not be specific for the pathogenic form of the prion.

In another aspect of this embodiment, a prion-binding reagent is provided on a solid support and contacted with a sample suspected of containing a pathogenic prion, under conditions that allow binding of the pathogenic prion, if present, to the prion-binding reagent. Unbound sample materials can be removed and the pathogenic prion can be detected, either while remaining bound to the peptide reagent or after dissociation from the peptide reagent. The pathogenic prion can be detected using one or more detectably labeled peptide reagents of the invention.

In another aspect of this embodiment, the pathogenic prion in a sample can be bound nonspecifically to a solid support (e.g., an ELISA plate) and detected by the binding of one or more detectably labeled peptide reagents of the invention that interact preferentially with the pathogenic prion isoform.

In a further embodiment, the method comprises contacting the sample suspected of containing a pathogenic prion with one or more peptide reagents selected from the group consisting of peptides having the sequences of SEQ ID NO: 12-132, and analogs and derivatives thereof, under conditions which allow the binding of the peptide reagent(s) to the pathogenic prion, if present; and detecting the presence or absence of the pathogenic prion in the sample by its binding to the peptide reagent(s). In preferred embodiments, the sample is contacted with one or more peptide reagents selected from the group consisting of peptides having the sequences of SEQ ID NO: 66, 67, 68, 72, 81, 96, 97, 98, 107, 108, 119, 120, 121, 122, 123, 124, 125, 126, 127, 14, 35, 36, 37, 40, 50, 51, 77, 89, 100, 101, 109, 110, 111, 112, 113, 114, 115, 116, 117, 118, 128, 129, 130, 131, 132, 56, 57, 65, 82, or 84, and analogs and derivatives thereof.

In still other embodiments, a method for detecting a pathogenic prion in a sample is provided, the method comprising: providing a solid support comprising a first peptide, wherein the first peptide comprises one or more of the peptide reagents as described herein that interact preferentially with $PrP^{Sc}$; contacting the solid support with the sample under conditions which allow pathogenic prions, when present in the sample, to bind to the first peptide; contacting the solid support with a detectably labeled second peptide, wherein the second peptide comprises one or more of the peptide reagents described herein that interact preferentially with $PrP^{Sc}$ proteins, under conditions which allow the second peptide to bind to pathogenic prions bound by the first peptide; and detecting complexes formed between the first peptide, a pathogenic prion from the sample and the second peptide, thereby detecting the presence of the pathogenic prion in the sample.

In still other embodiments, provided herein is a method for detecting the presence of a pathogenic prion in a sample comprising: providing a solid support comprising a prion-binding reagent, wherein the prion-binding reagents binds prion proteins; contacting the solid support with the sample under conditions which allow prion proteins, when present in the sample, to bind to the prion-binding reagent; contacting the solid support with a detectably labeled peptide reagent of the invention, wherein the peptide reagent interacts preferentially with the pathogenic prion protein; and detecting complexes formed between the prion-binding reagent, a pathogenic prion from the sample, and the peptide reagent.

In another embodiment, a method for detecting the presence of a pathogenic prion in a sample is provided, the method comprising the steps of providing a solid support comprising a first peptide reagent as described herein, wherein the first peptide reagent interacts preferentially with pathogenic forms; contacting the solid support with a detectably labeled first ligand (e.g., plasminogen, laminin receptor and heparan sulfate), under conditions that allow the formation of a detectably labeled peptide reagent-ligand complex, wherein the first peptide reagent's binding affinity for the detectably labeled first ligand is weaker than the first peptide reagent's binding affinity for a pathogenic prion; contacting a sample suspected of containing pathogenic prions with the solid support under conditions which allow a pathogenic prion, when present in the sample, to bind to the first peptide reagent and replace the first ligand; and detecting presence of the pathogenic prion in the sample by decrease in detectably labeled ligand on the solid support.

Any of the above methods of detection of a pathogenic prion can be used in a method to diagnose a prion-related disease.

The present invention also provides a method for isolating a pathogenic prion comprising: providing a solid support comprising one or more peptide reagents of the invention, contacting the solid support with a sample known or suspected of containing a pathogenic prion under conditions that allow the binding of the pathogenic prion, if present, to the peptide reagent; and removing any unbound sample materials. Additional embodiments further comprise the step of dissociating the bound pathogenic prion from the peptide reagent, and optionally, recovering the dissociated pathogenic prion.

The present invention also provides a method for removing pathogenic prions from a sample comprising: providing a solid support comprising one or more peptide reagents of the invention, contacting the solid support with a sample known or suspected of containing pathogenic prions, under conditions which allow the binding of the pathogenic prions, if present, to the peptide reagent; and recovering the unbound sample materials.

In all of the foregoing embodiments providing a solid support comprising one or more peptide reagents of the invention, alternative embodiments are contemplated in which the peptide reagent is contacted with the sample prior to the peptide reagent being attached to the solid support. In these embodiments, the peptide reagent comprises one member of a binding pair and the solid support comprises the second member of the binding pair. For example, the peptide reagent of the invention may contain or be modified to contain biotin. The biotinylated peptide reagent is contacted with a sample suspected to contain a pathogenic prion under conditions to allow binding of the peptide reagent to the pathogenic prion. A solid support comprising avidin or streptavidin is then contacted with the biotinylated peptide reagent. Other suitable binding pairs are described herein.

In any of the methods using a solid support described herein, the solid support can be, for example, nitrocellulose, polystyrene, polypropylene, latex, polyvinyl fluoride, diazotized paper, nylon membranes, activated beads, and/or magnetically responsive beads, polyvinylchloride; polypropylene, polystyrene latex, polycarbonate, nylon, dextran, chitin, sand, silica, pumice, agarose, cellulose, glass, metal, polyacrylamide, silicon, rubber, polysaccharides; diazotized paper; activated beads, magnetically responsive beads, and any materials commonly used for solid phase synthesis, affinity separations, purifications, hybridization reactions, immunoassays and other such applications. The support can be particulate or can be in the form of a continuous surface and includes membranes, mesh, plates, pellets, slides, disks, capillaries, hollow fibers, needles, pins, chips, solid fibers, gels (e.g. silica gels) and beads, (e.g., pore-glass beads, silica gels, polystyrene beads optionally cross-linked with divinylbenzene, grafted co-poly beads, polyacrylamide beads, latex beads, dimethylacrylamide beads optionally crosslinked with N-N'-bis-acryloylethylenediamine, iron oxide magnetic beads, and glass particles coated with a hydrophobic polymer.

In addition, in any of the methods described herein the sample can be a biological sample, that is, a sample obtained or derived from a living or once-living organism, for example, organs, whole blood, blood fractions, blood components, plasma, platelets, serum, cerebrospinal fluid (CSF), brain tissue, nervous system tissue, muscle tissue, bone marrow, urine, tears, non-nervous system tissue, organs, and/or biopsies or necropsies. In preferred embodiments, the biological sample comprises blood, blood fractions or blood components. The sample may be a non-biological sample.

In another aspect, the present invention provides a method of diagnosing a prion-related disease in a subject by detecting the presence of a pathogenic prion in a biological sample from said subject by any of the detection methods described herein.

In another aspect, the invention includes methods of preparing a blood supply that is substantially free of pathogenic prions, the method comprising the steps of screening aliquots of blood (e.g., whole blood, plasma, platelets or serum) from collected blood samples by any of the methods described herein; eliminating any sample in which pathogenic prions are detected; and combining samples where pathogenic prions are not detected to provide a blood supply substantially free of pathogenic prions.

In yet another aspect, the invention includes methods of preparing a food supply, in particular, a meat supply (e.g., beef, lamb, mutton or pork used for human or animal consumption) that is substantially free of pathogenic prions, the method of comprising the steps of screening, using any of the methods of detection described herein, samples collected from live or dead organisms that will enter the food supply or samples collected from food intended to enter the food supply; identifying samples in which pathogenic prions are detected; and removing from the food supply any live or dead organism or food intended to enter the food supply, in samples from which, pathogenic prions are detected; thereby providing a food supply that is substantially free of pathogenic prions.

In another aspect, the invention includes a solid support comprising one or more peptide reagents as described herein. The solid support can be used, inter alia, in the methods of the invention for detecting a pathogenic prion protein in a sample, for isolating a prion protein from a sample, and for eliminating pathogenic prion proteins from a sample. The solid support can be as described above.

In another aspect, the invention includes various kits for detecting the presence of a pathogenic prion in a sample, for isolating a pathogenic prion from a sample, for eliminating a pathogenic prion from a sample, the kit comprising: one or more of the peptide reagents described herein; and/or any of the solid supports comprising one or more of the peptide reagents described herein and other necessary reagents and, optionally, positive and negative controls. The peptide reagent(s) may be detectably labeled.

In other aspects, provided herein are compositions comprising one or more of the peptide reagents, polynucleotides and/or antibodies described herein.

In a further aspect, methods of treating or preventing prion disease are provided, for example, methods comprising administering to an animal (e.g., non-human or human mammal) one or more compositions described herein. In other embodiments, the methods comprise administering a first composition comprising any of the compositions described herein in a priming step and administering a second composition comprising a any of the compositions described herein as a booster, for example in an amount sufficient to induce an immune response in the subject. The composition(s) may be administered intramuscularly, intramucosally, intranasally, subcutaneously, intradermally, transdermally, intravaginally, intrarectally, orally and/or intravenously.

These and other embodiments of the subject invention will readily occur to those of skill in the art in light of the disclosure herein.

BRIEF DESCRIPTION OF THE DRAWINGS

FIG. 1 depicts the amino acid sequence of human (SEQ ID NO:1) and mouse (SEQ ID NO:2) prion proteins.

FIG. 2 depicts an alignment of prion proteins from human (SEQ ID NO:3), Syrian hamster (hamster) (SEQ ID NO:4), bovine (SEQ ID NO:5), sheep (SEQ ID NO:6), mouse (SEQ ID NO:7), elk (SEQ ID NO:8), fallow deer (fallow) (SEQ ID NO:9), mule deer (mule) (SEQ ID NO:10), and white tailed deer (white) (SEQ ID NO:11). Elk, Fallow Deer, Mule Deer, and White Tailed Deer only vary from each other at two residues, S/N128 and Q/E226 (shown in bold).

FIG. 3, panels A-F depict exemplary peptoid substitutions that may be made to prepare any of the peptide reagents described herein. The peptoids are circled in each panel and are shown in an exemplary peptide reagent as described herein (SEQ ID NO:14, QWNKPSKPKTNG), in which a proline residue (residue 8 of SEQ ID NO:14) is replaced with an N-substituted glycine (peptoid) residue. Panel A shows a peptide reagent in which a proline residue is substituted with the peptoid residue: N-(S)-(1-phenylethyl)glycine; panel B shows a peptide reagent in which a proline residue is substituted with the peptoid residue: N-(4-hydroxyphenyl)glycine; panel C shows a peptide reagent in which a proline residue is substituted with the peptoid residue: N-(cyclopropylmethyl) glycine; panel D shows a peptide reagent in which a proline residue is substituted with the peptoid residue: N-(isopropyl) glycine; panel E shows a peptide reagent in which a proline residue is substituted with the peptoid residue: N-(3,5-dimethoxybenzyl)glycine; and panel F shows a peptide reagent in which a proline residue is substituted with the peptoid residue: N-butylglycine.

DETAILED DESCRIPTION

Figure 4:
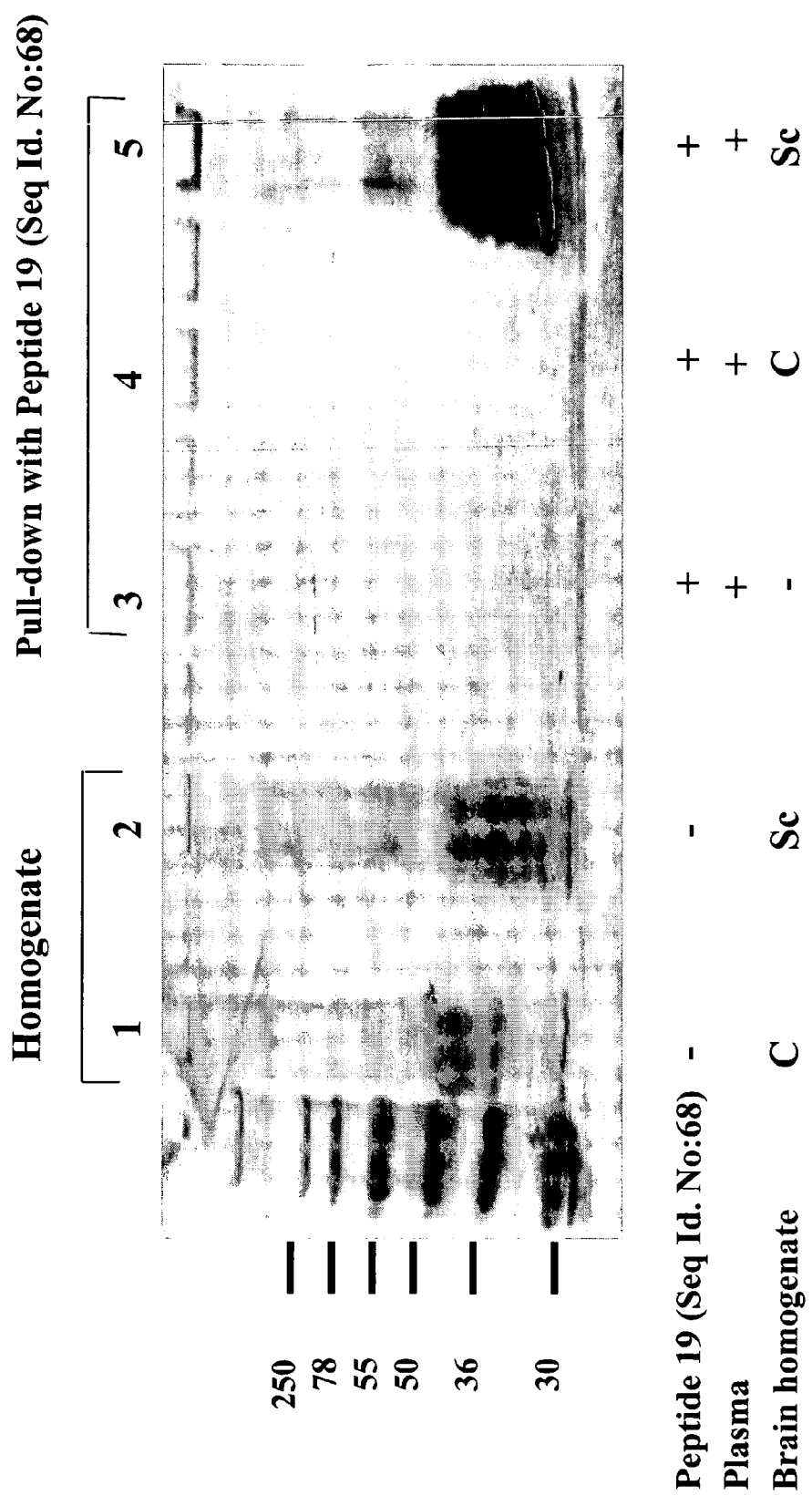
FIG. 4 depicts results of Western blotting experiments as described in Example 2. Lanes 1 and 2 show the presence of prion proteins in normal mouse brain homogenates (Lane 1, labeled "C") and in denatured infected mouse brain homogenates (lane 2, labeled "Sc"). Lanes 3, 4 and 5 show specific binding of a peptide reagent as described herein (SEQ ID NO:68) to pathogenic prion forms in the presence of human plasma. In particular, Lane 3 is a human plasma control and lane 4 is a normal mouse brain homogenate sample. Lane 5 shows strong binding by the peptide reagent to PrPSc in infected mouse brain homogenate samples.

The invention relates to the surprising and unexpected discovery that relatively small peptides (less than 50 to 100 amino acids in length, preferably less than 50 amino acids in length and even more preferably less than about 30 amino acids in length) can be used to discriminate between non-pathogenic and pathogenic prion proteins. Thus, the present disclosure relates to the surprising finding that these peptides and derivatives thereof (collectively "peptide reagents"), may bind pathogenic and nonpathogenic protein forms at different specificity and/or affinity and, accordingly, can be used, in and of themselves, as diagnostic/detection reagents or as components of therapeutic compositions. Prior to the present disclosure, it was believed that only larger molecules (e.g., antibodies, PrP$^C$, a-form rPrP and plasminogen) could be used to differentiate pathogenic and nonpathogenic forms. As such, previously described antigenic peptides were used to generate antibodies that were evaluated for their ability to discriminate between pathogenic and nonpathogenic forms. However, due to the relatively nonimmunogenic nature of prion proteins, it has proven difficult to generate antibodies specific for pathogenic forms. See, e.g., R. A. Williamson et al. "Antibodies as Tools to Probe Prion Protein Biology" in PRION BIOLOGY AND DISEASES, ed. S. Prusiner, Cold Spring Harbor Laboratory Press, 1999, pp:717-741.

The discovery that certain peptides as described herein interact preferentially with pathogenic ($PrP^{Sc}$) prion proteins allows for the development of novel reagents for diagnostics, detection assays and therapeutics, inter alia. Thus, the invention relates to peptide reagents and, in addition, relates to detection assays and diagnostic assays utilizing these peptide reagents, purification or isolation methods utilizing these peptide reagents and therapeutic compositions comprising these peptide reagents. Also provided are polynucleotides encoding these peptide reagents, and antibodies generated using these peptide reagents. The peptide reagents, polynucleotides and/or antibodies described herein are useful in compositions and methods for detecting the presence of pathogenic prions, for example in a biological sample. In addition, the invention further relates to methods of using such peptide reagents, antibodies and/or polynucleotides as a component in a therapeutic or prophylactic composition.

The peptide reagents (and polynucleotides encoding these peptide reagents) used in the invention comprise a peptide that interacts preferentially with pathogenic isoforms as compared to nonpathogenic isoforms. For example, in certain embodiments, peptide reagents as described herein specifically bind to pathogenic conformational disease protein forms and do not bind (or bind to a lesser extent) to non-pathogenic forms. The peptide reagents described herein (and polynucleotides encoding same) may be used, for example, to generate antibodies. These antibodies may recognize pathogenic forms, non-pathogenic forms or both. These molecules are useful, alone or in various combinations, in diagnostic assays and/or in prophylactic or therapeutic compositions.

The practice of the present invention will employ, unless otherwise indicated, conventional methods of chemistry, biochemistry, molecular biology, immunology and pharmacology, within the skill of the art. Such techniques are explained fully in the literature. See, e.g., *Remington's Pharmaceutical Sciences*, 18th Edition (Easton, Pa.: Mack Publishing Company, 1990); *Methods In Enzymology* (S. Colowick and N. Kaplan, eds., Academic Press, Inc.); and *Handbook of Experimental Immunology*, Vols. I-IV (D. M. Weir and C. C. Blackwell, eds., 1986, Blackwell Scientific Publications); Sambrook, et al., *Molecular Cloning: A Laboratory Manual* (2nd Edition, 1989); *Handbook of Surface and Colloidal Chemistry* (Birdi, K. S. ed., CRC Press, 1997); *Short Protocols in Molecular Biology*, 4th ed. (Ausubel et al. eds., 1999, John Wiley & Sons); *Molecular Biology Techniques: An Intensive Laboratory Course*, (Ream et al., eds., 1998, Academic Press); *PCR (Introduction to Biotechniques Series)*, 2nd ed. (Newton & Graham eds., 1997, Springer Verlag); Peters and Dalrymple, *Fields Virology* (2d ed), Fields et al. (eds.), B. N. Raven Press, New York, N.Y.

It is understood that the peptide reagents, antibodies and methods of this invention are not limited to particular formulations or process parameters as such may, of course, vary. It is also to be understood that the terminology used herein is for the purpose of describing particular embodiments of the invention only, and is not intended to be limiting.

All publications, patents and patent applications cited herein are hereby incorporated by reference in their entirety.

I. Definitions

In order to facilitate an understanding of the invention, selected terms used in the application will be discussed below.

The terms "prion", "prion protein", "PrP protein" and "PrP" are used interchangeably herein to refer to both the pathogenic protein form (variously referred to as scrapie protein, pathogenic protein form, pathogenic isoform, pathogenic prion and $PrP^{SC}$) and the non-pathogenic form (variously referred to as cellular protein form, cellular isoform, nonpathogenic isoform, nonpathogenic prion protein, and $PrP^{C}$), as well as the denatured form and various recombinant forms of the prion protein which may not have either the pathogenic conformation or the normal cellular conformation. The pathogenic protein form is associated with disease state (spongiform encephalopathies) in humans and animals; the non-pathogenic form is normally present in animal cells and may, under appropriate conditions, be converted to the pathogenic $PrP^{Sc}$ conformation. Prions are naturally produced in a wide variety of mammalian species, including human, sheep, cattle, and mice. A representative amino acid sequence of a human prion protein is set forth as SEQ ID NO:1. A representative amino acid sequence of a mouse prion protein is set forth as SEQ ID NO:2. Other representative sequences are shown in FIG. 2.

As used herein, the term "pathogenic" may mean that the protein actually causes the disease or it may simply mean that the protein is associated with the disease and therefore is present when the disease is present. Thus, a pathogenic protein as used in connection with this disclosure is not necessarily a protein that is the specific causative agent of a disease. Pathogenic forms may or may not be infectious. The term "pathogenic prion form" is used more specifically to refer to the conformation and/or the beta-sheet-rich conformation of mammalian, avian or recombinant prion proteins. Generally, the beta-sheet-rich conformation is proteinase K resistant. The terms "non-pathogenic" and "cellular" when used with respect to conformational disease protein forms are used interchangeably to refer to the normal isoform of the protein whose presence is not associated with sickness.

Furthermore, a "prion protein" or "conformational disease protein" as used herein is not limited to a polypeptide having the exact sequence to those described herein. It is readily apparent that the terms encompass conformational disease proteins from any of the identified or unidentified species or diseases (e.g., Alzheimer's, Parkinson's, etc.). One of ordinary skill in the art in view of the teachings of the present disclosure and the art can determine regions corresponding to the sequences shown in the Figures in any other prion proteins, using for example, sequence comparison programs (e.g., BLAST and others described herein) or identification and alignment of structural features or motifs.

The term "PrP gene" is used herein to describe any genetic material that expresses prion proteins including known polymorphisms and pathogenic mutations. The term "PrP gene" refers generally to any gene of any species that encodes any form of a PrP protein. Some commonly known PrP sequences are described in Gabriel et al., Proc. Natl. Acad. Sci. USA 89:9097-9101 (1992), and U.S. Pat. Nos. 5,565,186; 5,763, 740; 5,792,901; and WO97/04814, incorporated herein by reference to disclose and describe such sequences. The PrP gene can be from any animal, including the "host" and "test" animals described herein and any and all polymorphisms and mutations thereof, it being recognized that the terms include other such PrP genes that are yet to be discovered. The protein expressed by such a gene can assume either a $PrP^{C}$ (non-disease) or $PrP^{Sc}$ (disease) form.

"Prion-related disease" as used herein refers to a disease caused in whole or in part by a pathogenic prion protein ($PrP^{Sc}$). Prion-related diseases include, but are not limited to, scrapie, bovine spongiform encephalopathies (BSE), mad cow disease, feline spongiform encephalopathies, kuru, Creutzfeldt-Jakob Disease (CJD), new variant Creutzfeldt-Jakob Disease (nvCJD), chronic wasting disease (CWD), Gerstmann-Strassler-Scheinker Disease (GSS), and fatal familial insomnia (FFI).

The term "peptide reagent" as used herein generally refers to any compound comprising naturally occurring or synthetic polymers of amino acid or amino acid-like molecules, including but not limited to compounds comprising only amino and/or imino molecules. The peptide reagents of the present invention interact preferentially with a pathogenic prion protein and are typically derived from fragments of a prion protein. The term "peptide" will be used interchangeably with "oligopeptide" or "polypeptide" and no particular size is implied by use of these terms Included within the definition are, for example, peptides containing one or more analogs of an amino acid (including, for example, unnatural amino acids, peptoids, etc.), peptides with substituted linkages, as well as other modifications known in the art, both naturally occurring and non-naturally occurring (e.g., synthetic). Thus, synthetic peptides, dimers, multimers (e.g., tandem repeats, multiple antigenic peptide (MAP) forms, linearly-linked peptides), cyclized, branched molecules and the like, are included within the definition. The terms also include molecules comprising one or more N-substituted glycine residues (a "peptoid") and other synthetic amino acids or peptides. (See, e.g., U.S. Pat. Nos. 5,831,005; 5,877,278; and 5,977, 301; Nguyen et al. (2000) *Chem Biol.* 7(7):463-473; and Simon et al. (1992) *Proc. Natl. Acad. Sci. USA* 89(20):9367-9371 for descriptions of peptoids). Non-limiting lengths of peptides suitable for use in the present invention includes peptides of 3 to 5 residues in length, 6 to 10 residues in length (or any integer therebetween), 11 to 20 residues in length (or any integer therebetween), 21 to 75 residues in length (or any integer therebetween), 75 to 100 (or any integer therebetween), or polypeptides of greater than 100 residues in length. Typically, peptides useful in this invention can have a maximum length suitable for the intended application. Preferably, the peptide is between about 3 and 100 residues in length. Generally, one skilled in art can easily select the maximum length in view of the teachings herein. Further, peptide reagents as described herein, for example synthetic peptides, may include additional molecules such as labels, linkers, or other chemical moieties (e.g., biotin, amyloid specific dyes such as Control Red or Thioflavin). Such moieties may further enhance interaction of the peptides with the prion proteins and/or further detection of prion proteins.

Peptide reagents also includes derivatives of the amino acid sequences of the invention having one or more substitution, addition and/or deletion, including one or more non-naturally occurring amino acid. Preferably, derivatives exhibit at least about 50% identity to any wild type or reference sequence, preferably at least about 70% identity, more preferably at least about 75%, 80%, 85%, 90%, 91%, 92%, 93%, 94%, 95%, 96%, 97%, 98%, 99% or 100% sequence identity to any wild type or reference sequence described herein. Sequence (or percent) identity can be determined as described below. Such derivatives can include postexpression modifications of the polypeptide, for example, glycosylation, acetylation, phosphorylation, and the like.

Peptide derivatives can also include modifications to the native sequence, such as deletions, additions and substitutions (generally conservative in nature), so long as the polypeptide maintains the desired activity. These modifications may be deliberate, as through site-directed mutagenesis, or may be accidental, such as through mutations of hosts that produce the proteins or errors due to PCR amplification. Furthermore, modifications may be made that have one or more of the following effects: reducing toxicity; increasing affinity and/or specificity for prion proteins; facilitating cell processing (e.g., secretion, antigen presentation, etc.); and facilitating presentation to B-cells and/or T-cells. Polypeptides described herein can be made recombinantly, synthetically, purified from natural sources, or in tissue culture.

A "fragment" as used herein refers to a peptide consisting of only a part of the intact full-length protein and structure as found in nature. For instance, a fragment can include a C-terminal deletion and/or an N-terminal deletion of a protein. Typically, the fragment retains one, some or all of the functions of the full-length polypeptide sequence from which it is derived. Typically, a fragment will comprise at least 5 consecutive amino acid residues of the native protein; preferably, at least about 8 consecutive amino acid residues; more preferably, at least about 10, 11, 12, 13, 14, 15, 16, 17, 18, 19, 20, 21, 22, 23, 24, 25, 26, 27, 28, 29, or 30 consecutive amino acid residues of the native protein.

The term "polynucleotide", as known in the art, generally refers to a nucleic acid molecule. A "polynucleotide" can include both double- and single-stranded sequences and refers to, but is not limited to, prokaryotic sequences, eukaryotic mRNA, cDNA from viral, prokaryotic or eukaryotic mRNA, genomic RNA and DNA sequences from viral (e.g. RNA and DNA viruses and retroviruses), prokaryotic DNA or eukaryotic (e.g., mammalian) DNA, and especially synthetic DNA sequences. The term also captures sequences that include any of the known base analogs of DNA and RNA, and includes modifications such as deletions, additions and substitutions (generally conservative in nature), to the native sequence. These modifications may be deliberate, as through site-directed mutagenesis, or may be accidental, such as through mutations of hosts including prion-encoding polynucleotides. Modifications of polynucleotides may have any number of effects including, for example, facilitating expression of the polypeptide product in a host cell.

A polynucleotide can encode a biologically active (e.g., immunogenic or therapeutic) protein or polypeptide. Depending on the nature of the polypeptide encoded by the polynucleotide, a polynucleotide can include as little as 10 nucleotides, e.g., where the polynucleotide encodes an antigen or epitope. Typically, the polynucleotide encodes peptides of at least 18, 19, 20, 21, 22, 23, 24, 25, 30 or even more amino acids.

A "polynucleotide coding sequence" or a sequence that "encodes" a selected polypeptide, is a nucleic acid molecule that is transcribed (in the case of DNA) and translated (in the case of mRNA) into a polypeptide in vivo when placed under the control of appropriate regulatory sequences (or "control elements"). The boundaries of the coding sequence are determined by a start codon at the 5' (amino) terminus and a translation stop codon at the 3' (carboxy) terminus. A transcription termination sequence may be located 3' to the coding sequence. Typical "control elements," include, but are not limited to, transcription regulators, such as promoters, transcription enhancer elements, transcription termination signals, and polyadenylation sequences; and translation regulators, such as sequences for optimization of initiation of translation, e.g., Shine-Dalgarno (ribosome binding site) sequences, Kozak sequences (i.e., sequences for the optimization of translation, located, for example, 5' to the coding sequence), leader sequences (heterologous or native), translation initiation codon (e.g., ATG), and translation termination sequences. Promoters can include inducible promoters (where expression of a polynucleotide sequence operably linked to the promoter is induced by an analyte, cofactor, regulatory protein, etc.), repressible promoters (where expression of a polynucleotide sequence operably linked to the promote is included by an analyte, cofactor, regulatory protein, etc.), and constitutive promoters.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

A "recombinant" nucleic acid molecule as used herein to describe a nucleic acid molecule means a polynucleotide of genomic, cDNA, semi synthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting prokaryotic microorganisms or eukaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

By "isolated" is meant, when referring to a polynucleotide or a polypeptide, that the indicated molecule is separate and discrete from the whole organism with which the molecule is found in nature or, when the polynucleotide or polypeptide is not found in nature, is sufficiently free of other biological macromolecules so that the polynucleotide or polypeptide can be used for its intended purpose.

"Antibody" as known in the art includes one or more biological moieties that, through chemical or physical means, can bind to or associate with an epitope of a polypeptide of interest. For example, the antibodies of the invention may interact preferentially with (e.g., specifically bind to) pathogenic prion conformations. The term "antibody" includes antibodies obtained from both polyclonal and monoclonal preparations, as well as the following: hybrid (chimeric) antibody molecules (see, for example, Winter et al. (1991) Nature 349: 293-299; and U.S. Pat. No. 4,816,567; F(ab')$_2$ and F(ab) fragments; F$_v$, molecules (non-covalent heterodimers, see, for example, Inbar et al. (1972) Proc Natl Acad Sci USA 69:2659-2662; and Ehrlich et al. (1980) Biochem 19:4091-4096); single-chain Fv molecules (sFv) (see, for example, Huston et al. (1988) Proc Natl Acad Sci USA 85:5897-5883); dimeric and trimeric antibody fragment constructs; minibodies (see, e.g., Pack et al. (1992) Biochem 31:1579-1584; Cumber et al. (1992) J Immunology 149B: 120-126); humanized antibody molecules (see, for example, Riechmann et al. (1988) Nature 332:323-327; Verhoeyan et al. (1988) Science 239:1534-1536; and U.K. Patent Publication No. GB 2,276, 169, published 21 Sep. 1994); and, any functional fragments obtained from such molecules, wherein such fragments retain immunological binding properties of the parent antibody molecule. The term "antibody" further includes antibodies obtained through non-conventional processes, such as phage display.

As used herein, the term "monoclonal antibody" refers to an antibody composition having a homogeneous antibody population. The term is not limited regarding the species or source of the antibody, nor is it intended to be limited by the manner in which it is made. Thus, the term encompasses antibodies obtained from murine hybridomas, as well as human monoclonal antibodies obtained using human rather than murine hybridomas. See, e.g., Cote, et al. Monoclonal Antibodies and Cancer Therapy, Alan R. Liss. 1985, p 77.

If polyclonal antibodies are desired, a selected mammal (e.g., mouse, rabbit, goat, horse, etc.) is generally immunized with an immunogenic composition (e.g., a peptide reagent as described herein). Serum from the immunized animal is collected and treated according to known procedures. If serum containing polyclonal antibodies to the selected peptide reagent contains antibodies to other antigens, the polyclonal antibodies can be purified by immunoaffinity chromatography. Techniques for producing and processing polyclonal antisera are known in the art, see for example, Mayer and Walker, eds. (1987) IMMUNOCHEMICAL METHODS IN CELL AND MOLECULAR BIOLOGY (Academic Press, London).

One skilled in the art can also readily produce monoclonal antibodies directed against peptide reagents described herein. The general methodology for making monoclonal antibodies by hybridomas is well known. Immortal antibody-producing cell lines can be created by cell fusion, and also by other techniques such as direct transformation of B-lymphocytes with oncogenic DNA, or transfection with Epstein-Barr virus. See, e.g., M. Schreier et al. (1980) HYBRIDOMA TECHNIQUES; Hammerling et al. (1981), MONOCLONAL ANTIBODIES AND T-CELL HYBRIDOMAS; Kennett et al. (1980) MONOCLONAL ANTIBODIES; see also, U.S. Pat. Nos. 4,341,761; 4,399,121; 4,427,783; 4,444, 887; 4,466,917; 4,472,500; 4,491,632; and 4,493,890.

As used herein, a "single domain antibody" (dAb) is an antibody that is comprised of an VH domain, which binds specifically with a designated antigen. A dAb does not contain a VL domain, but may contain other antigen binding domains known to exist to antibodies, for example, the kappa and lambda domains. Methods for preparing dabs are known in the art. See, for example, Ward et al, Nature 341: 544 (1989).

Antibodies can also be comprised of VH and VL domains, as well as other known antigen binding domains. Examples of these types of antibodies and methods for their preparation are known in the art (see, e.g., U.S. Pat. No. 4,816,467, which is incorporated herein by reference), and include the following. For example, "vertebrate antibodies" refers to antibodies that are tetramers or aggregates thereof, comprising light and heavy chains which are usually aggregated in a "Y" configuration and which may or may not have covalent linkages between the chains. In vertebrate antibodies, the amino acid sequences of the chains are homologous with those sequences found in antibodies produced in vertebrates, whether in situ or in vitro (for example, in hybridomas). Vertebrate antibodies include, for example, purified polyclonal antibodies and monoclonal antibodies, methods for the preparation of which are described infra.

"Hybrid antibodies" are antibodies where chains are separately homologous with reference to mammalian antibody chains and represent novel assemblies of them, so that two different antigens are precipitable by the tetramer or aggregate. In hybrid antibodies, one pair of heavy and light chains are homologous to those found in an antibody raised against a first antigen, while a second pair of chains are homologous to those found in an antibody raised against a second antibody. This results in the property of "divalence", i.e., the ability to bind two antigens simultaneously. Such hybrids can also be formed using chimeric chains, as set forth below.

"Chimeric antibodies" refers to antibodies in which the heavy and/or light chains are fusion proteins. Typically, one portion of the amino acid sequences of the chain is homologous to corresponding sequences in an antibody derived from a particular species or a particular class, while the remaining segment of the chain is homologous to the sequences derived from another species and/or class. Usually, the variable region of both light and heavy chains mimics the variable regions or antibodies derived from one species of vertebrates, while the constant portions are homologous to the sequences in the antibodies derived from another species of vertebrates. However, the definition is not limited to this particular example. Also included is any antibody in which either or both of the heavy or light chains are composed of combinations of sequences mimicking the sequences in antibodies of different sources, whether these sources be from differing classes or different species of origin, and whether or not the fusion point is at the variable/constant boundary. Thus, it is possible, to produce antibodies in which neither the constant nor the variable region mimic known antibody sequences. It then becomes possible, for example, to construct antibodies whose variable region has a higher specific affinity for a particular antigen, or whose constant region can elicit enhanced complement fixation, or to make other improvements in properties possessed by a particular constant region.

Another example is "altered antibodies", which refers to antibodies in which the naturally occurring amino acid sequence in a vertebrate antibody has been varies. Utilizing recombinant DNA techniques, antibodies can be redesigned to obtain desired characteristics. The possible variations are many, and range from the changing of one or more amino acids to the complete redesign of a region, for example, the constant region. Changes in the constant region, in general, to attain desired cellular process characteristics, e.g., changes in complement fixation, interaction with membranes, and other effector functions. Changes in the variable region can be made to alter antigen-binding characteristics. The antibody can also be engineered to aid the specific delivery of a molecule or substance to a specific cell or tissue site. The desired alterations can be made by known techniques in molecular biology, e.g., recombinant techniques, site-directed mutagenesis, etc.

Yet another example are "univalent antibodies", which are aggregates comprised of a heavy-chain/light-chain dimer bound to the Fc (i.e., stem) region of a second heavy chain. This type of antibody escapes antigenic modulation. See, e.g., Glennie et al. Nature 295: 712 (1982). Included also within the definition of antibodies are "Fab" fragments of antibodies. The "Fab" region refers to those portions of the heavy and light chains which are roughly equivalent, or analogous, to the sequences which comprise the branch portion of the heavy and light chains, and which have been shown to exhibit immunological binding to a specified antigen, but which lack the effector Fc portion. "Fab" includes aggregates of one heavy and one light chain (commonly known as Fab'), as well as tetramers containing the 2H and 2L chains (referred to as F(ab)$_2$), which are capable of selectively reacting with a designated antigen or antigen family. Fab antibodies can be divided into subsets analogous to those described above, i.e., "vertebrate Fab", "hybrid Fab", "chimeric Fab", and "altered Fab". Methods of producing Fab fragments of antibodies are known within the art and include, for example, proteolysis, and synthesis by recombinant techniques.

"Antigen-antibody complex" refers to the complex formed by an antibody that is specifically bound to an epitope on an antigen.

A peptide (or peptide reagent) is said to "interact" with another peptide or protein if it binds specifically, non-specifically or in some combination of specific and non-specific binding. A peptide (or peptide reagent) is said to "interact preferentially" with a pathogenic prion protein if it bind with greater affinity and/or greater specificity to the pathogenic form than to nonpathogenic isoforms. A peptide reagent that interacts preferentially with a pathogenic prion protein is also referred to herein as a pathogenic prion-specific peptide reagent. It is to be understood that a preferential interaction does not necessarily require interaction between specific amino acid residues and/or motifs of each peptide. For example, in certain embodiments, the peptide reagents described herein interact preferentially with pathogenic isoforms but, nonetheless, may be capable of binding nonpathogenic isoforms at a weak, yet detectable, level (e.g., 10% or less of the binding shown to the polypeptide of interest). Typically, weak binding, or background binding, is readily discernible from the preferentially interaction with the compound or polypeptide of interest, e.g., by use of appropriate controls. In general, peptides of the invention bind pathogenic prions in the presence of $10^6$-fold excess of nonpathogenic forms.

The term "affinity" refers to the strength of binding and can be expressed quantitatively as a dissociation constant ($K_d$). Preferably, a peptide (or peptide reagent) that interacts preferentially with a pathogenic isoform preferably interacts with the pathogenic isoform with at least 2 fold greater affinity, more preferably at least 10 fold greater affinity and even more preferably at least 100 fold greater affinity than it interacts with the nonpathogenic isoform. Binding affinity (i.e., $K_d$) can be determined using standard techniques.

Techniques for determining amino acid sequence "similarity" or "percent identity" are well known in the art. In general, "similarity" means the amino acid to amino acid comparison of two or more polypeptides at the appropriate place, where amino acids are identical or possess similar chemical and/or physical properties such as charge or hydrophobicity. A so-termed "percent identity" then can be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded thereby, and comparing this to a second amino acid sequence. In general, "identity" refers to an exact nucleotide to nucleotide or amino acid to amino acid correspondence of two polynucleotides or polypeptide sequences, respectively.

Two or more amino acid or polynucleotide sequences can be compared by determining their "percent identity." Percent identity can be determined by a direct comparison of the sequence information between two molecules (the reference sequence and a sequence with unknown % identity to the reference sequence) by aligning the sequences, counting the exact number of matches between the two aligned sequences, dividing by the length of the reference sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRC™ package of programs copyrighted by the University of Edinburgh, developed by John F. Collins and Shane S. Sturrok, and available from numerous sources, for example on the internet. From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+Swiss protein+Spupdate+PIR. Details of these programs are readily available.

An "immunogenic composition" as used herein refers to any composition (e.g., peptide, antibody and/or polynucleotides) where administration of the composition to a subject results in the development in the subject of a humoral and/or a cellular immune response. The immunogenic composition can be introduced directly into a recipient subject, such as by injection, inhalation, oral, intranasal or any other parenteral or mucosal (e.g., intra-rectally or intra-vaginally) route of administration.

By "epitope" is meant a site on an antigen to which specific B cells and/or T cells respond, rendering the molecule including such an epitope capable of eliciting an immunological reaction or capable of reacting with antibodies present in a biological sample. The term is also used interchangeably with "antigenic determinant" or "antigenic determinant site." An epitope can comprise 3 or more amino acids in a spatial conformation unique to the epitope. Generally, an epitope consists of at least 5 such amino acids and, more usually, consists of at least 8-10 such amino acids. Methods of determining spatial confrontation of amino acids are known in the art and include, for example, x-ray crystallography and 2-dimensional nuclear magnetic resonance. Furthermore, the identification of epitopes in a given protein is readily accomplished using techniques well known in the art, such as by the use of hydrophobicity studies and by site-directed serology. See, also, Geysen et al., *Proc. Natl. Acad. Sci. USA* (1984) 81:3998-4002 (general method of rapidly synthesizing peptides to determine the location of immunogenic epitopes in a given antigen); U.S. Pat. No. 4,708,871 (procedures for identifying and chemically synthesizing epitopes of antigens); and Geysen et al., *Molecular Immunology* (1986) 23:709-715 (technique for identifying peptides with high affinity for a given antibody). Antibodies that recognize the same epitope can be identified in a simple immunoassay showing the ability of one antibody to block the binding of another antibody to a target antigen.

An "immunological response" or "immune response" as used herein is the development in the subject of a humoral and/or a cellular immune response to a peptide as described herein when the polypeptide is present in a vaccine composition. These antibodies may also neutralize infectivity, and/or mediate antibody-complement or antibody dependent cell cytotoxicity to provide protection to an immunized host. Immunological reactivity may be determined in standard immunoassays, such as a competition assays, well known in the art.

"Gene transfer" or "gene delivery" refers to methods or systems for reliably inserting DNA of interest into a host cell. Such methods can result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from alphaviruses, pox viruses and vaccinia viruses. When used for immunization, such gene delivery expression vectors may be referred to as vaccines or vaccine vectors.

The term "sample" includes biological and non-biological samples. Biological samples are those obtained or derived from a living or once-living organism. Non-biological samples are not derived from living or once-living organisms. Biological samples include, but are not limited to, samples derived from an animal (living or dead) such as organs (e.g., brain, liver, kidney, etc), whole blood, blood fractions, plasma, cerebrospinal fluid (CSF), urine, tears, tissue, organs, biopsies. Examples of non-biological samples include pharmaceuticals, foods, cosmetics and the like.

The terms "label" and "detectable label" refer to a molecule capable of detection, including, but not limited to, radioactive isotopes, fluorescers, luminescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof that is capable of exhibiting fluorescence in the detectable range. Particular examples of labels that may be used with the invention include, but are not limited to fluorescein, rhodamine, dansyl, umbelliferone, Texas red, luminol, acradimum esters, NADPH, beta-galactosidase, horseradish peroxidase, glucose oxidase, alkaline phosphatase and urease. The label can also be an epitope tag (e.g., a His-His tag), an antibody or a amplifiable or otherwise detectable oligonucleotide.

II. General Overview

Described herein are compositions comprising a peptide reagent (and/or polynucleotides encoding these peptide reagents) in which the peptide reagent is capable of distinguishing between pathogenic and nonpathogenic isoforms of prion proteins, for example by preferentially interacting with one form and not the other. Antibodies generated using these peptide reagents as well as compositions comprising and methods of making and using these peptide reagents and/or antibodies are also provided (e.g., for isolation and/or detection of the pathogenic prion protein).

The invention relies in part on the discovery by the present inventors that relatively small fragments of a prion protein can interact preferentially with the pathogenic form of the prion. These fragments need not be part of a larger protein structure or other type of scaffold molecule in order to exhibit this preferential interaction with the pathogenic prion isoform. While not wanting to be held to any particular theory, it appears that the peptide fragments spontaneously take on a conformation that allows binding to the pathogenic prion isoform but not to the nonpathogenic prion isoform, perhaps by mimicking a conformation that is present in the nonpathogenic isoform. This general principle, that certain fragments of a conformational disease protein interact preferentially with the pathogenic form of that conformational disease protein, here demonstrated for prions, can readily be applied to other conformational disease proteins to produce peptide reagents that interact preferentially with the pathogenic forms. It will be apparent to one of ordinary skill in the art that, while the fragments provide a starting point (in terms of size or sequence characteristics, for example), that many modifications can be made on the fragments to produce peptide reagents with more desirable attributes (e.g, higher affinity, greater stability, greater solubility, less protease sensitivity, greater specificity, easier to synthesize, etc.).

In general, the peptide reagents described herein are able to interact preferentially with pathogenic forms of prion proteins. Thus, these peptide reagents allow for ready detection of the presence of pathogenic prion proteins and, hence, diagnosis of prion-related diseases in virtually any sample, biological or non-biological, including living or dead brain, spinal cord, or other nervous system tissue as well as blood.

In addition, the peptide reagents described herein can be used to generate antibodies that may be used in diagnostic or therapeutic compositions and methods. In particular, where a peptide reagent and/or antibody interacts preferentially with a pathogenic protein, it can be used to detect the presence of pathogenic isoforms, for example by ordering, aggregating or otherwise inducing the disease form proteins to a state that can then be detected. The peptide reagents described herein are useful in a variety of diagnostic assays, including to detect pathogenic forms in blood-containing samples. The antibodies and/or peptide reagents (or one or more of their component parts) can be labeled or marked to facilitate detection and/or enhance interaction with the prion proteins.

In addition, any suitable signal amplification system can be used to further facilitate detection, including but not limited to, the use of branched DNA for signal amplification (see, e.g., U.S. Pat. Nos. 5,681,697; 5,424,413; 5,451,503; 5,4547, 025; and 6,235,483); applying target amplification techniques like PCR, rolling circle amplification, Third Wave's invader (Arruda et al. 2002 Expert. Rev. Mol. Diagn. 2:487; U.S. Pat. Nos. 6,090,606, 5,843,669, 5985557, 6090543, 5846717), NASBA, TMA etc. (U.S. Pat. No. 6,511,809; EP 0544212A1); and/or immuno-PCR techniques (see, e.g., U.S. Pat. No. 5,665,539; International Publications WO 98/23962; WO 00/75663; and WO 01/31056).

Furthermore, the peptide reagents and antibodies described herein can be used, alone or in any combinations, to treat or prevent disease.

III. A. Peptide Reagents

Described herein are peptide reagents that interact with pathogenic forms of a conformational disease protein. Conformational disease proteins are exemplified herein by prion proteins.

The following is a non-limiting list of diseases with associated proteins that assume two or more different conformations.

| Disease | Conformational Disease Protein(s) |
|---|---|
| Prion diseases (e.g., Creutzfeld Jakob disease, scrapie, bovine spongiform encephalopathy) | PrP$^{Sc}$ |
| Alzheimer's Disease | APP, A* peptide, *1-antichymotrypsin, tan, non-A* component |
| ALS | SOD and neurofilament |
| Pick's disease | Pick body |
| Parkinson's disease | Lewy body |
| Diabetes Type 1 | Amylin |
| Multiple myeloma - plasma cell dyscrasias | IgGL-chain |
| Familial amyloidotic polyneuropathy | Transthyretin |
| Medullary carcinoma of thyroid | Procalcitonin |
| Chronic Renal failure | beta2-microglobulin |
| Congestive heart failure | atrial natriuretic factor |
| senile cardiac and systemic amyloidosis | Transthyretin |
| Chronic inflammation | Serum amyloid A |
| Atherosclerosis | ApoA1 |
| Familial amyloidosis | Gelsolin |

Further, the conformational disease proteins listed above each include a number of variants or mutations that result in different strains that are all encompassed by the present invention. Functional analysis of various regions and sequences of a mouse prion protein are given below. See, also, Priola (2001) Adv. Protein Chem. 57:1-27. Regions and residues corresponding to those set forth below for mouse (Mo), hamster (Ha), human (Hu), avian (A) and sheep (Sh) can readily be determined for other species following standard procedures and the teachings herein.

| Amino Acid(s) | Function |
|---|---|
| Mo1-28 | Translocation domain (cleaved) |
| 22 | Putative cleavage site |
| 23-28 | Basic region potentially interacting with Protein X binding site as its deletion abrogates the effect of protein X associated mutations in the C-terminus of prion proteins. |
| 23-88 | Octarepeat region (1-9 insertions or 2 deletions potentiate disease); Copper coordination by the histidines in each of the repeats |
| 34-52 | Portion of Octarepeat shown for form a polyproline helix and also to form hydroxyproline |
| 86-91 | Cleavage sites of PrP$^{Sc}$ when Proteinase K digests |
| Hu82-146 | 7 Kda fragment found in diseased brains of GSS patients; synthetic peptide corresponding to this region forms ion channels |
| HuP102 | P102L mutation associated with GSS, does not appear to cause spontaneous conversion of the prion protein to protease resistant conformation; Proline conserved in all species examined. |
| HuP105 | P105L mutation associated with GSS, does not appear to cause spontaneous conversion of the prion protein to protease resistant conformation; Proline conserved in all species examined. |
| Hu102-105 | PXXP motif; possible polyproline type II helix |
| Mo_106 | Associated with disease resistance |
| Hu106-126 | Mutant forms of synthetic peptides suggested to form copper modulating ion channels; G114 and G119 shown to decrease fibrillogenic behavior of this peptide as peptide is more amyloidogenic when they are mutated to A. |
| Mo_111 | Associated with disease resistance |
| Sh104-113 | Peptide co-crystallized with D13 Fab |

-continued

| Amino Acid(s) | Function |
|---|---|
| Ha109-112 | Loop specifically recognized by D13 peptide as shown in crystal structure (M109 and M112 are inserted into binding pockets within the Fab). |
| Hu113-120 | Palindromic sequence; totally conserved |
| A117V | Pathogenic mutation in palindrome; increases amyloidogenic properties of peptides containing that region |
| Ha129-131 | Beta sheet 1 in $PrP^C$ |
| Hu129/ Go132 | Polymorphism associated with susceptibility/resistance to prion disease |
| Ha136 | Alanine polymorphism associated with increase in coated pits in sheep |
| Mo138/ Go142 | Polymorphism associated with susceptibility/resistance to prion disease |
| Mo141-176 | Area deleted (along with 23-88) in mouse miniprion PrP106 has no effect; suggests non-essential function for this region |
| Ha144-154 | Helix A |
| Ha155 | Polymorphism associated with susceptibility/resistance to prion disease |
| Ha160-163 | Sheet 2 |
| MoV165 | Species barrier; when human transgenic mice mutate these residues back to mouse sequence, much faster incubation times are obtained |
| MoQ167 | Species barrier; when human transgenic mice mutate these residues back to mouse sequence, much faster incubation times are obtained |
| MoQ168 | Putative Protein X binding site; when mutated it protects against prion disease |
| Sh171 | Polymorphism associated with susceptibility/resistance to prion disease |
| MoQ172 | Putative Protein X binding site; when mutated it protects against prion disease |
| 176 | Disulfide-linked cysteine. |
| Ha173-194 | Helix B |
| 178 | Disease-associated mutation |
| 180 | Disease-associated mutation; glycosylation site |
| 196 | Glycosylation site |
| 198 | Disease-associated mutation |
| Hu200-228 | Helix C |
| HuE200 | Mutation to K associated with familial CJD in Lybian Jews (M129 polymorphism in combo also increases chances of disease) |
| 208 | Disease-associated mutation |
| 210 | Disease-associated mutation |
| MoT215 | Putative Protein X binding site; when mutated it protects against prion disease |
| 217 | Disease-associated mutation |
| MoQ219 | Putative Protein X binding site; when mutated it protects against prion disease |
| 232 | Disease-associated mutation |
| 232 | GPI anchor |
| ~233 | Putative GPI anchor cleavage site |
| 233-254 | Portion removed from mature protein |

It should also be noted that prion proteins (and other conformational disease proteins) have two different 3-dimensional conformations with the same amino acid sequence. One conformation is associated with disease characteristics and is generally insoluble whereas the other conformation is not associated with disease characteristics and is soluble. See, e.g., Wille, et al., "Structural Studies of the Scrapie Prion Protein by Electron Crystallography", *Proc. Natl. Acad. Sci. USA,* 99 (6): 3563-3568 (2002). Although exemplified with respect to prion proteins, the present invention is not limited to the diseases, proteins and strains listed.

Thus, in certain aspects, the peptide reagents described herein comprise an amino acid sequence derived from a naturally occurring protein, for example a conformational disease protein (e.g., prion protein) or a protein that contains motifs or sequences that exhibit homology to prion proteins. In particular, the peptide reagents of the invention are typically derived from a naturally-occurring prion protein. The peptide reagents are preferably derived from the amino acid sequences from certain regions of the prion proteins. These preferred regions are exemplified with respect to the mouse prion sequence (SEQ ID NO:2), in regions from amino acid residue 23-43 and 85-156, and subregions thereof. The invention is not limited topeptide reagents derived from the mouse sequences but include peptide reagents derived in similar fashion as described herein, from prion sequences of any species, including human, bovine, sheep, deer, elk, hamster. When derived from prion proteins, the peptide reagents described herein may include a polyproline type II helix motif. This motif typically contains the general sequence PxxP (e.g., residues 102-105 of SEQ ID NO:1), although other sequences, in particular alanine tetrapeptides, have been suggested to form polyproline type II helices as well (see, e.g., Nguyen et al. *Chem Biol.* 20007:463; Nguyen et al. *Science* 1998 282:2088; Schweitzer-Stenner et al. *J. Am. Chem Soc.* 2004 126:2768). In the PxxP sequence, "x" can be any amino acid and "P" is proline in the naturally occuring sequence but may be replaced by a proline substitute in the peptide reagents of the invention. Such proline substitutes include N-substituted glycines commonly referred to as peptoids. Thus, in the peptide reagents of the invention that include a polyproline type II helix based on the PxxP sequence, "P" represents a proline or an N-substituted glycine residues and "x" represents any amino acid or amino acid analog. Particularly preferred N-substituted glycines are described herein.

Further, the polynucleotide and amino acid sequence for prion proteins produced by many different species are known, including human, mouse, sheep and cattle. Variants to these sequences also exist within each species. Thus, the peptide reagents used in the invention can comprise fragments or derivatives of the amino acid sequences of any species or variant. For example, in certain embodiments, the peptide reagents described herein are derived from any of the sequences set forth in FIG. 2 (SEQ ID NOs:3-11). The sequences of the peptide reagents that are specifically disclosed herein are generally based on the mouse prion sequence, however, one skilled in the art can readily substitute corresponding sequences from other species when appropriate. For example, if human diagostics or therapeutics are desired, replacement of the mouse sequences with those of the corresponding human sequences can be easily done. In a particular example, in peptide reagents derived from the region from about residue 85 to about residue 112 (e.g., SEQ ID NO:35, 36, 37, 40), the leucine at position corresponding to residue 109 may be replaced with a methionine, the valine at position corresponding to residue 112 may be replaced with methionine, and the asparagine at position corresponding to 97 may be replaced with serine. Likewise, if a bovine diagnostic is desired, the appropriate substitutions may be made in the disclosed peptide sequences to reflect the bovine prion sequence. Thus, continuing with the above example for peptide reagents derived from the region from about residue 85 to about residue 112, the leucine at position corresponding to residue 109 may be replaced with a methionine and the asparagine at position corresponding to 97 may be replaced with glycine. Derivatives of prion proteins, including amino acid replacements, deletions, additions and other mutations to these sequences can also be used. Preferably, any amino acid replacements, additions, and deletions as compared to a prion protein sequence do not affect the ability of the peptide reagent to interact with pathogenic form.

It should be understood that no matter what source is used for the peptide reagents described herein, these peptide reagents will not necessarily exhibit sequence identity to known prion proteins. Thus, the peptide reagents described herein can include one or more amino acid replacements, additions, and deletions relative to the naturally0occuring prion protein or the sequences disclosed herein, so long as they retain the ability to interact preferentially with pathogenic forms of conformational disease proteins. In certain embodiments, conservative amino acid replacements are preferred. Conservative amino acid replacements are those that take place within a family of amino acids that are related in their side chains. Genetically encoded amino acids are generally divided into four families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. For example, it is reasonably predictable that an isolated replacement of a leucine with an isoleucine or valine, an aspartate with a glutamate, a threonine with a serine, or a similar conservative replacement of an amino acid with a structurally related amino acid will not have a major effect on the biological activity.

It will also be apparent that any combination of the natural amino acids and non-natural amino acid analogs can be used to make the peptide reagents described herein. Commonly encountered amino acid analogs that are not gene-encoded include, but are not limited to, ornithine (Orn); aminoisobutyric acid (Aib); benzothiophenylalanine (BtPhe); albizziin (Abz); t-butylglycine (Tle); phenylglycine (PhG); cyclohexylalanine (Cha); norleucine (Nle); 2-naphthylalanine (2-Nal); 1-naphthylalanine (1-Nal); 2-thienylalanine (2-Thi); 1,2,3,4-tetrahydroisoquinoline-3-carboxylic acid (Tic); N-methylisoleucine (N-MeIle); homoarginine (Har); Na-methylarginine (N-MeArg); phosphotyrosine (pTyr or pY); pipecolinic acid (Pip); 4-chlorophenylalanine (4-ClPhe); 4-fluorophenylalanine (4-FPhe); 1-aminocyclopropanecarboxylic acid (1-NCPC); and sarcosine (Sar). Any of the amino acids used in the peptide reagents of the present invention may be either the D- or, more typically, L-isomer.

Other non-naturally occurring analogs of amino acids that may be used to form the peptide reagents described herein include peptoids and/or peptidomimetic compounds such as the sulfonic and boronic acid analogs of amino acids that are biologically functional equivalents are also useful in the compounds of the present invention and include compounds having one or more amide linkages optionally replaced by an isostere. In the context of the present invention, for example, —CONH— may be replaced by —CH$_2$NH—, —NHCO—, —SO$_2$NH—, —CH$_2$O—, —CH$_2$CH$_2$—, —CH$_2$S—, —CH$_2$SO—, —CH=CH—(cis or trans), —COCH$_2$—, —CH(OH)CH$_2$— and 1,5-disubstituted tetrazole such that the radicals linked by these isosteres would be held in similar orientations to radicals linked by —CONH—. One or more residues in the peptide reagents described herein may comprise peptoids.

Thus, the peptide reagents also may comprise one or more N-substituted glycine residues (peptides having one or more N-substituted glycine residues may be referred to as "peptoids"). For example, in certain embodiments, one or more proline residues of any of the peptide reagents described herein are replaced with N-substituted glycine residues. Particular N-substituted glycines that are suitable in this regard include, but are not limited to, N-(S)-(1-phenylethyl)glycine; N-(4-hydroxyphenyl)glycine; N-(cyclopropylmethyl)glycine; N-(isopropyl)glycine; N-(3,5-dimethoxybenzyl)glycine; and N-butylglycine. (e.g., FIG. 3). Other N-substituted glycines may also be suitable to replace one or more amino acid residues in the peptide reagents sequences described herein. For a general review of these and other amino acid analogs and peptidomimetics see, Nguyen et al. (2000) Chem Biol. 7(7):463-473; Spatola, A. F., in Chemistry and Biochemistry of Amino Acids, Peptides and Proteins, B. Weinstein, eds., Marcel Dekker, New York, p. 267 (1983). See also, Spatola, A. F., Peptide Backbone Modifications (general review), Vega Data, Vol. 1, Issue 3, (March 1983); Morley, Trends Pharm Sci (general review), pp. 463-468 (1980); Hudson, D. et al., Int J Pept Prot Res, 14:177-185 (1979) (—CH$_2$NH—, CH$_2$CH$_2$—); Spatola et al., Life Sci, 38:1243-1249 (1986) (—CH$_2$—S); Hann J. Chem. Soc. Perkin Trans. I, 307-314 (1982) (—CH—CH—, cis and trans); Almquist et al., J Med Chem, 23:1392-1398 (1980) (—COCH$_2$—); Jennings-White et al., Tetrahedron Lett, 23:2533 (1982) (—COCH$_2$—); Szelke et al., European Appln. EP 45665 CA: 97:39405 (1982) (—CH(OH)CH$_2$—); Holladay et al., Tetrahedron Lett, 24:4401-4404 (1983) (—C(OH)CH$_2$—); and Hruby, Life Sci, 31:189-199 (1982) (—CH$_2$—S—); each of which is incorporated herein by reference. The C-terminal carboxylic acid can be replaced by a boronic acid —B(OH)$_2$ or boronic ester —B(OR)$_2$ or other such boronic acid derivative as disclosed in U.S. Pat. No. 5,288,707, incorporated herein by reference.

The peptide reagents described herein may comprise monomers, multimers, cyclized molecules, branched molecules, linkers and the like. Multimers (i.e., dimers, trimers and the like) of any of the sequences described herein or biologically functional equivalents thereof are also contemplated. The multimer can be a homomultimer, i.e., composed of identical monomers, e.g., each monomer is the same peptide sequence. Alternatively, the multimer can be a heteromultimer, by which is meant that not all the monomers making up the multimer are identical.

Multimers can be formed by the direct attachment of the monomers to each other or to substrate, including, for example, multiple antigenic peptides (MAPS) (e.g., symmetric MAPS), peptides attached to polymer scaffolds, e.g., a PEG scaffold and/or peptides linked in tandem with or without spacer units.

Alternatively, linking groups can be added to the monomeric sequences to join the monomers together and form a multimer. Non-limiting examples of multimers using linking groups include tandem repeats using glycine linkers; MAPS attached via a linker to a substrate and/or linearly linked peptides attached via linkers to a scaffold. Linking groups may involve using bifunctional spacer units (either homobifunctional or heterobifunctional) as are known to one of skill in the art. By way of example and not limitation, many methods for incorporating such spacer units in linking peptides together using reagents such as succinimidyl-4-(p-maleimidomethyl)cyclohexane-1-carboxylate (SMCC), succinimidyl-4-(p-maleimidophenyl)butyrate and the like are described in the Pierce Immunotechnology Handbook (Pierce Chemical Co., Rockville, Ill.) and are also available from Sigma Chemical Co. (St. Louis, Mo.) and Aldrich Chemical Co. (Milwaukee, Wis.) and described in "Comprehensive Organic Transformations", VCK-Verlagsgesellschaft, Weinheim/Germany (1989). One example of a linking group which may be used to link the monomeric sequences together is —Y$_1$—F—Y$_2$— where Y$_1$ and Y$_2$ are identical or different and are alkylene groups of 0-20, preferably 0-8, more preferably 0-3 carbon atoms, and F is one or more functional groups such as —O—, —S—, —S—S—, —C(O)—O—, —NR—, —C(O)—NR—, —NR—C(O)—

O—, —NR—C(O)—NR—, —NR—C(S)—NR—, —NR—C(S)—O—. $Y_1$ and $Y_2$ may be optionally substituted with hydroxy, alkoxy, hydroxyalkyl, alkoxyalkyl, amino, carboxyl, carboxyalkyl and the like. It will be understood that any appropriate atom of the monomer can be attached to the linking group.

Further, the peptide reagents of the invention may be linear, branched or cyclized. Monomer units can be cyclized or may be linked together to provide the multimers in a linear or branched fashion, in the form of a ring (for example, a macrocycle), in the form of a star (dendrimers) or in the form of a ball (e.g., fullerenes). Skilled artisans will readily recognize a multitude of polymers that can be formed from the monomeric sequences disclosed herein. In certain embodiments, the multimer is a cyclic dimer. Using the same terminology as above, the dimer can be a homodimer or a heterodimer.

Cyclic forms, whether monomer or multimer, can be made by any of the linkages described above, such as but not limited to, for example: (1) cyclizing the N-terminal amine with the C-terminal carboxylic acid either via direct amide bond formation between the nitrogen and the C-terminal carbonyl, or via the intermediacy of spacer group such as for example by condensation with an epsilon-amino carboxylic acid; (2) cyclizing via the formation of a bond between the side chains of two residues, e.g., by forming a amide bond between an aspartate or glutamate side chain and a lysine side chain, or by disulfide bond formation between two cysteine side chains or between a penicillamine and cysteine side chain or between two penicillamine side chains; (3) cyclizing via formation of an amide bond between a side chain (e.g., aspartate or lysine) and either the N-terminal amine or the C-terminal carboxyl respectively; and/or (4) linking two side chains via the intermediacy of a short carbon spacer group.

Preferably, the peptide reagents described herein are not pathogenic and/or infectious.

The peptide reagents of the invention can be anywhere from 3 to about 100 residues long (or any value therebetween) or even longer, preferably from about 4 to 75 residues (or any value therebetween), preferably from about 5 to about 63 residues (or any value therebetween), and even more preferably from about 8 to about 30 residues (or any value therebetween), and most preferably the peptide reagent will be 10, 11, 12, 13, 14, 15, 16, 17, 18, 19, 20, 21, 22, 23, 24, 25, 26, 27, 28, 29 or 30 residues.

Non-limiting examples of peptide reagents useful in the compositions and methods described herein are derived from sequences shown in Table 1 and in Table 4. Peptide reagents in the tables are represented by conventional one letter amino acid codes and are depicted with their N-terminus at the left and C-terminus at the right. Amino acids in square brackets indicate alternative residues that can be used at that position in different peptide reagents. Round brackets indicate the residue(s) may be present or absent from the peptide reagent. Any proline residue may be substituted with N-substituted glycine residues to form peptoids. Any of the sequences in the tables may optionally include Gly linkers ($G_n$ where n=1,2,3, or 4) at the N- and/or C- terminal.

TABLE 1

| Peptide sequence | SEQ ID NO |
|---|---|
| KKRPK | 12 |
| MANLGCWMLVLFVATWSDLGLC | 13 |
| (GGG)QWNKPSKPKTN | 14 |
| QWNKPSKPKTNMKHV | 15 |
| NQNN[N/T]FVHDCVNIT[I/V]K[Q/E]HTVTTTTKGEN | 16 |
| TTKGENFTETD | 17 |
| GENFTETD | 18 |
| GENFTETD[V/I]K[M/I]MERVVEQMC[I/V]TQY[E/Q]ESQAYY[Q/D](G)(R)R[G/S][S/A]S | 19 |
| NQNN[N/T]FVHDCVNIT[I/V]K[Q/E]HTVTTTTKGENFTETD[V/I]K[M/I]MERVVEQMC[I/V]TQY[E/Q]ESQAYY[Q/D](G)(R)R[G/S][S/A]S | 20 |
| [A/V/T/M][V/I]LFSSPPVILLISFLIFL[I/M]VG | 21 |
| G[N/S]D[W/Y]EDRYYRENM[H/Y]RYPNQVYYRP[M/V]D[Q/E/R]Y[S/N]NQN[N/T]FVH | 22 |
| N[N/T]FVHDCVNIT[I/V]K[Q/E]HTVTTTTK | 23 |
| VYYR | 24 |
| RYPNQVYYRP[M/V]D[Q/E/R] | 25 |
| KKRPKPGG(G)WNTGGSRYPGQGSPGGNRYPPQGG | 26 |
| WNTGGSRYPGQGSPGGNRYPPQGG(G) | 27 |
| WNTGGSRYPGQGSPGGNRYPPQGG(G)[G/T]WGQPHGG | 28 |
| GGWGQGGTHSQWNKPSKPKTN | 29 |
| GGTHSQWNKPSKPKTN | 30 |
| WNTGGSRYPGQGSPGGNRYPPQGG(G)[G/T]WGQPHGGGWGQPHGGGWGQPHGG | 31 |
| GQPHGGGW | 32 |
| RPIIHFGSDYEDRYYRENMHR | 33 |
| RPMIHFGNDWEDRYYRENMYR | 34 |
| (GGGG)C(GG)GGWGQGGGTHNQWNKPSKPKTNLKHV(GGGG)C | 35 |
| (GGGG)GGWGQGGGTHNQWNKPSKPKTNLKHV | 36 |
| GGWGQGGGTHNQWNKPSKPKTNLKHV(GGGG) | 37 |
| [M/L]KH[M/V] | 38 |
| KPKTN[M/L]KH[M/V] | 39 |
| C(GG)GGWGQGGGTHNQWNKPSKPKTNLKHV(GGGG)C | 40 |
| SRPIIHFGSDYEDRYYRENMHRYPN | 41 |
| PMIHFGNDWEDRYYRENMYRPVD | 42 |
| AGAAAAGAVVGGLGGYMLGSAM | 43 |
| RPMIHFGNDWEDRYYRENMYR(GGG) | 44 |
| GGGRPMIHFGNDWEDRYYRENMYRGG | 45 |
| (GG)C(GGG)RPMIHFGNDWEDRYYRENMYR(GGG)C | 46 |
| AGAAAAGAVVGGLGG | 47 |
| GGLGG | 48 |
| LGS | 49 |

TABLE 1-continued

| Peptide sequence | SEQ ID NO |
|---|---|
| QWNKPSKPKTN(GGG) | 50 |
| QWNKPSKPKTN(GGG)QWNKPSKPKTN | 51 |
| QWNKPSKPKTNLKHV(GGG) | 52 |
| GGWGQGGGTHNQWNKPSKPKTN | 53 |
| GGTHNQWNKPSKPKTN | 54 |
| (GGG)AGAAAAGAVVGGLGGYMLGSAM | 55 |
| (GGG)AGAAAAGAVVGGLGG | 56 |
| (KKK)AGAAAAGAVVGGLGGYMLGSAM | 57 |
| YMLGSAM[S/N]R | 58 |
| [S/N]RP[M/I/L][I/L]H | 59 |
| YMLGSAM[S/N]RP[M/I/L][I/L]H | 60 |
| YMLGSAM[S/N]RP[M/I/L][I/L]HFG[N/S]D | 61 |
| [W/Y]EDRYYRENM[H/Y]RYPNQVYYRP[M/V]D[Q/E/R]Y | 62 |
| [W/Y]EDRYYRENM[H/Y]RYPNQVYYRP[M/V]D[Q/E/R]Y[S/N]NQN[N/T] | 63 |
| D[Q/E/R]Y[S/N]NQN[N/T] | 64 |
| (KKK)AGAAAAGAVVGGLGG | 65 |
| (GGG)KKRPKPGGWNTGGSRYPGQGS | 66 |
| (GGG)KKRPKPGGWNTGG | 67 |
| (GGG)KKRPKPGG | 68 |
| PHGGGWGQHGGSWGQPHGGSWGQ | 69 |
| PHGGGWGQPHGGSWGQ | 70 |
| PHGGGWGQ | 71 |
| (GGG)KKRPKPGGGKKRPKPGG | 72 |
| (GGG)GPKRKGPK | 73 |
| (GGG)WNTGGSRYPGQGS | 74 |
| (GGG)WNKPSKPKT | 75 |
| (GGG)RPMIHFGNDWEDRYYRENMYR(GG)C | 76 |
| QWNKPSKPKTNLKHV(GGG) | 77 |
| (GGG)AGAAAAGAVVGGLGGYMLGSAM | 78 |
| (GGG)NKPSKPK | 79 |
| (GGG)KPSKPK | 80 |
| (GGG)KKRPKPGGGQWNKPSKPKTN | 81 |
| KKKAGAAAAGAVVGGLGGYMLGSAMDDD | 82 |
| DDDAGAAAAGAVVGGLGGYMLGSAM | 83 |
| KKKAGAAAAGAVVGGLGGYMLGSAMKKK | 84 |
| (GGG)KKKKKKKK | 85 |
| DDDAGAAAAGAVVGGLGGYMLGSAMDDD | 86 |

TABLE 1-continued

| Peptide sequence | SEQ ID NO |
|---|---|
| (GGG)NNKQSPWPTKK | 87 |
| DKDKGGVGALAGAAVAAGGDKDK | 88 |
| (GGG)QANKPSKPKTN | 89 |
| (GGG)QWNKASKPKTN | 90 |
| (GGG)QWNKPSKAKTN | 91 |
| (GGG)QWNAPSKPKTN | 92 |
| (GGG)QWNKPSAPKTN | 93 |
| (GGG)QWNKPSKPATN | 94 |
| (GGG)QWNKASKAKTN | 95 |
| (GGG)KKRAKPGG | 96 |
| (GGG)KKRPKAGG | 97 |
| (GGG)KKRAKAGG | 98 |
| (GGG)QWNKASKPKTN | 99 |
| (GGG)QWAKPSKPKTN | 100 |
| (GGG)QWNKPAKPKTN | 101 |
| (GGG)QWNKPSKPKAN | 102 |
| (GGG)QWNKPSKPKTA | 103 |
| (GGG)AKRPKPGG | 104 |
| (GGG)KARPKPGG | 105 |
| (GGG)KKAPKPGG | 106 |
| (GGG)KKRPAPGG | 107 |
| (GGG)KKAPKAGG | 108 |
| (GGG)KKRPKPGGGWNTGG | 127 |
| QWNKPSKPKTNGGGQWNKPSKPKTNGGGQWNKPSKPKTN | 128 |

In one aspect, the peptide reagent of the invention includes each of the peptides disclosed herein and derivatives (as described herein) thereof. The invention thus includes a peptide reagent derived from a peptide of SEQ ID NO: 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, or 132.

The invention preferably includes a peptide reagent derived from a peptide of SEQ ID NO: 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 72, 74, 76, 77, 78, 81, 82, 84, 89, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, or 132.

In certain preferred embodiments, the peptide reagents specifically bind to pathogenic prion, for example peptide reagents derived from peptides of SEQ ID NOs: 66, 67, 68, 72, 81, 96, 97, 98, 107, 108, 119, 120, 121, 122, 123, 124, 125, 126, 127, 14, 35, 36, 37, 40, 50, 51, 77, 89, 100, 101, 109, 110, 111, 112, 113, 114, 115, 116, 117, 118, 128, 129, 130, 131, 132, 56, 57, 65, 82, or 84, and analogs (e.g., substitution of one or more proline with a N-substituted glycine) and derivatives thereof.

As described above, the peptide reagents described herein may include one or more substitutions, additions, and/or mutations. For example, one or more residues may be replaced in the peptide reagents with other residues, for example alanine residues or with an amino acid analog or N-substituted glycine residue in order to make a peptoid (see, e.g., Nguyen et al. (2000) *Chem Biol.* 7(7):463-473).

Furthermore, the peptide reagents described herein may also include additional peptide or non-peptide components. Non-limiting examples of additional peptide components include spacer residues, for example two or more glycine (natural or derivatized) residues or aminohexanoic acid linkers on one or both ends or residues that may aid in solubilizing the peptide reagents, for example acidic residues such as aspartic acid (Asp or D) as depicted for example in SEQ ID NOs:83, 86. In certain embodiments, for example, the peptide reagents are synthesized as multiple antigenic peptides (MAPs). Typically, multiple copies of the peptide reagents (e.g., 2-10 copies) are synthesized directly onto a MAP carrier such as a branched lysine or other MAP carrier core. See, e.g., Wu et al. (2001) *J Am Chem Soc.* 2001 123(28):6778-84; Spetzler et al. (1995) *Int J Pept Protein Res.* 45(1):78-85.

Non-limiting examples of non-peptide components (e.g., chemical moieties) that may be included in the peptide reagents described herein include, one or more detectable labels, tags (e.g., biotin, His-Tags, oligonucleotides), dyes, members of a binding pair, and the like, at either terminus or internal to the peptide reagent. The non-peptide components may also be attached (e.g., via covalent attachment of one or more labels), directly or through a spacer (e.g., an amide group), to position(s) on the compound that are predicted by quantitative structure-activity data and/or molecular modeling to be non-interfering. Peptide reagents as described herein may also include prion-specific chemical moieties such as amyloid-specific dyes (e.g., Congo Red, Thioflavin, etc.). Derivatization (e.g., labeling, cyclizing, attachment of chemical moieties, etc.) of compounds should not substantially interfere with (and may even enhance) the binding properties, biological function and/or pharmacological activity of the peptide reagent.

The peptide reagents of the invention will typically have at least about 50% sequence identity to prion protein fragments or to the peptide sequences set forth herein. Preferably, the peptide reagents will have at least 70% sequence identity: more preferably at least 75, 80, 85, 90, 91, 92, 93, 94, 95, 96, 97, 98, 99, or 100% sequence identity identity to prion protein fragments or to the peptide sequences set forth herein.

The peptide reagents as described herein interact preferentially with the pathogenic forms and, accordingly, are useful in a wide range of isolation, purification, detection, diagnostic and therapeutic applications. For example, in embodiments in which the peptide reagent interacts preferentially with pathogenic forms, the peptide reagents themselves can be used to detect pathogenic forms in a sample, such as a blood, nervous system tissue (brain, spinal cord, CSF, etc) or other tissue or organ sample. The peptide reagents are also useful to diagnose the presence of disease associated with the pathogenic forms, to isolate the pathogenic forms and to decontaminate samples by removing the pathogenic forms.

The interaction of the peptide reagents with prion proteins can be tested using any known binding assay, for example standard immuno assays such as ELISAs, Western blots and the like.

One convenient method of testing the specificity of the peptide reagents of the present invention is to select a sample containing both pathogenic and non-pathogenic prions. Typical such samples include brain or spinal cord tissue from diseased animals. Peptide reagents as described herein that bind specifically to pathogenic forms are attached to a solid support (by methods well-known in the art and as further described below) and used to separate ("pull down") pathogenic prion from the other sample components and obtain a quantitative value directly related to the number of peptide-prion binding interactions on the solid support. Variations and other assays known in the art can also be used to demonstrate the specificity of the peptide reagents of the invention. See, e.g., Examples.

Although not required when using the peptide reagents described herein, these assays may utilize the fact that prions having a pathogenic conformation are generally resistant to certain proteases, such as proteinase K. The same proteases are able to degrade prions in a non-pathogenic conformation. Therefore, when using a protease, the sample can be separated into two equal volumes. Protease can be added to the second sample and the same test performed. Because the protease in the second sample will degrade any non-pathogenic prions, any peptide-prion binding interactions in the second sample can be attributed to pathogenic prions.

Thus, non-limiting examples of methods of evaluating binding specificity and/or affinity of the peptide reagents described herein include standard Western and Far-Western Blotting procedures; labeled peptides; ELISA-like assays; and/or cell based assays. Western blots, for example, typically employ a tagged primary antibody that detects denatured prion protein from an SDS-PAGE gel, on samples obtained from a "pull-down" assay (as described herein), that has been electroblotted onto nitrocellulose or PVDF. Antibodies that recognize denatured prion protein have been described (described, inter alia, in Peretz et al. 1997 J. Mol. Biol. 273: 614; Peretz et al. 2001 Nature 412:739; Williamson et al. 1998 J. Virol. 72:9413; U.S. Pat. No. 6,765,088; U.S. Pat. No. 6,537548) and some are commercially available. Other prion-binding molecules have been described e.g., motif-grafted hybrid polypeptides (see, WO03/085086), certain cationic or anionic polymers (see, WO03/073106), certain peptides that are "propagation catalysts" (see, WO02/0974444) and plasminogen. The primary antibody is then detected (and/or amplified) with a probe for the tag (e.g., streptavidin-conjugated alkaline phosphatase, horseradish peroxidase, ECL reagent, and/or amplifiable oligonucleotides). Binding can also be evaluated using detection reagents such as a peptide with an affinity tag (e.g., biotin) that is labeled and amplified with a probe for the affinity tag (e.g., streptavidin-conjugated alkaline phosphatase, horseradish peroxidase, ECL reagent, or amplifiable oligonucleotides). In addition, microtitre plate procedures similar to sandwich ELISA may be used, for example, a prion-specific peptide reagent as described herein is used to immobilize prion protein(s) on a solid support (e.g., well of a microtiter plate, bead, etc.) and an additional detection reagent which could include, but is not limited to, another prion-specific peptide reagent with an affinity and/or detection label such as a conjugated alkaline phosphatase, horseradish peroxidase, ECL reagent, or amplifiable oligonucleotides. Cell based assays can also be employed, for example, where the prion protein is detected directly on individual cells (e.g., using a fluorescently labeled prion-specific peptide reagent that enables fluorescence based cell sorting, counting, or detection of the specifically labeled cells).

III.B. Peptide Reagent Production

The peptide reagents of the present invention can be produced in any number of ways, all of which are well known in the art.

In one embodiment, in which the peptide reagent is, in whole or in part, a genetically encoded peptide, the peptide can be generated using recombinant techniques, well known in the art. One of skill in the art could readily determining nucleotide sequences that encode the desired peptide using standard methodology and the teachings herein. Once isolated, the recombinant peptide, optionally, can be modified to include non-genetically encoded components (e.g., detectable labels, binding pair members, etc.) as described herein and as well-known in the art, to produce the peptide reagents.

Oligonucleotide probes can be devised based on the known sequences and used to probe genomic or cDNA libraries. The sequences can then be further isolated using standard techniques and, e.g., restriction enzymes employed to truncate the gene at desired portions of the full-length sequence. Similarly, sequences of interest can be isolated directly from cells and tissues containing the same, using known techniques, such as phenyl extraction and the sequence further manipulated to produce the desired truncations. See, e.g., Sambrook et al., supra, for a description of techniques used to obtain and isolate DNA.

The sequences encoding the peptide can also be produced synthetically, for example, based on the known sequences. The nucleotide sequence can be designed with the appropriate codons for the particular amino acid sequence desired. The complete sequence is generally assembled from overlapping oligonucleotides prepared by standard methods and assembled into a complete coding sequence. See, e.g., Edge (1981) *Nature* 292:756; Nambair et al. (1984) *Science* 223: 1299; Jay et al. (1984) *J. Biol. Chem.* 259:6311; Stemmer et al. (1995) *Gene* 164:49-53.

Recombinant techniques are readily used to clone sequences encoding polypeptides useful in the claimed peptide reagents that can then be mutagenized in vitro by the replacement of the appropriate base pair(s) to result in the codon for the desired amino acid. Such a change can include as little as one base pair, effecting a change in a single amino acid, or can encompass several base pair changes. Alternatively, the mutations can be effected using a mismatched primer that hybridizes to the parent nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. See, e.g., Innis et al, (1990) PCR Applications: Protocols for Functional Genomics; Zoller and Smith, *Methods Enzymol.* (1983) 100: 468. Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbie-McFarland et al. *Proc. Natl. Acad. Sci USA* (1982) 79:6409.

Once coding sequences have been isolated and/or synthesized, they can be cloned into any suitable vector or replicon for expression. (See, also, Examples). As will be apparent from the teachings herein, a wide variety of vectors encoding modified polypeptides can be generated by creating expression constructs which operably link, in various combinations, polynucleotides encoding polypeptides having deletions or mutations therein.

Numerous cloning vectors are known to those of skill in the art, and the selection of an appropriate cloning vector is a matter of choice. Examples of recombinant DNA vectors for cloning and host cells which they can transform include the bacteriophage? (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) and bovine papilloma virus (mammalian cells). See, generally, *DNA Cloning*: Vols. I & II, supra; Sambrook et al., supra; B. Perbal, supra.

Insect cell expression systems, such as baculovirus systems, can also be used and are known to those of skill in the art and described in, e.g., Summers and Smith, *Texas Agricultural Experiment Station Bulletin No.* 1555 (1987). Materials and methods for baculovirus/insect cell expression systems are commercially available in kit form from, inter alia, Invitrogen, San Diego Calif. ("MaxBac" kit).

Plant expression systems can also be used to produce the peptide reagents described herein. Generally, such systems use virus-based vectors to transfect plant cells with heterologous genes. For a description of such systems see, e.g., Porta et al., *Mol. Biotech.* (1996) 5:209-221; and Hackland et al., *Arch. Virol.* (1994) 139:1-22.

Viral systems, such as a vaccinia based infection/transfection system, as described in Tomei et al., *J. Virol.* (1993) 67:4017-4026 and Selby et al., *J. Gen. Virol.* (1993) 74:1103-1113, will also find use with the present invention. In this system, cells are first transfected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA that is then translated into protein by the host translational machinery. The method provides for high level, transient, cytoplasmic production of large quantities of RNA and its translation product(s).

The gene can be placed under the control of a promoter, ribosome binding site (for bacterial expression) and, optionally, an operator (collectively referred to herein as "control" elements), so that the DNA sequence encoding the desired polypeptide is transcribed into RNA in the host cell transformed by a vector containing this expression construction. The coding sequence may or may not contain a signal peptide or leader sequence. With the present invention, both the naturally occurring signal peptides or heterologous sequences can be used. Leader sequences can be removed by the host in post-translational processing. See, e.g., U.S. Pat. Nos. 4,431, 739; 4,425,437; 4,338,397. Such sequences include, but are not limited to, the TPA leader, as well as the honey bee mellitin signal sequence.

Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector. Alternatively, the coding sequence can be cloned directly into an expression vector that already contains the control sequences and an appropriate restriction site.

In some cases it may be necessary to modify the coding sequence so that it may be attached to the control sequences with the appropriate orientation; i.e., to maintain the proper reading frame. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; DNA Cloning, Vols. I and II, supra; *Nucleic Acid Hybridization*, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Vero293 cells, as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda,* and *Trichoplusia ni*.

Depending on the expression system and host selected, the proteins of the present invention are produced by growing host cells transformed by an expression vector described above under conditions whereby the protein of interest is expressed. The selection of the appropriate growth conditions is within the skill of the art.

In one embodiment, the transformed cells secrete the polypeptide product into the surrounding media. Certain regulatory sequences can be included in the vector to enhance secretion of the protein product, for example using a tissue plasminogen activator (TPA) leader sequence, an interferon (γ or α) signal sequence or other signal peptide sequences from known secretory proteins. The secreted polypeptide product can then be isolated by various techniques described herein, for example, using standard purification techniques such as but not limited to, hydroxyapatite resins, column chromatography, ion-exchange chromatography, size-exclusion chromatography, electrophoresis, HPLC, immunoadsorbent techniques, affinity chromatography, immunoprecipitation, and the like.

Alternatively, the transformed cells are disrupted, using chemical, physical or mechanical means, which lyse the cells yet keep the recombinant polypeptides substantially intact. Intracellular proteins can also be obtained by removing components from the cell wall or membrane, e.g., by the use of detergents or organic solvents, such that leakage of the polypeptides occurs. Such methods are known to those of skill in the art and are described in, e.g., *Protein Purification Applications: A Practical Approach*, (E. L. V. Harris and S. Angal, Eds., 1990).

For example, methods of disrupting cells for use with the present invention include but are not limited to: sonication or ultrasonication; agitation; liquid or solid extrusion; heat treatment; freeze-thaw; desiccation; explosive decompression; osmotic shock; treatment with lytic enzymes including proteases such as trypsin, neuraminidase and lysozyme; alkali treatment; and the use of detergents and solvents such as bile salts, sodium dodecylsulphate, Triton, NP40 and CHAPS. The particular technique used to disrupt the cells is largely a matter of choice and will depend on the cell type in which the polypeptide is expressed, culture conditions and any pretreatment used.

Following disruption of the cells, cellular debris is removed, generally by centrifugation, and the intracellularly produced polypeptides are further purified, using standard purification techniques such as but not limited to, column chromatography, ion-exchange chromatography, size-exclusion chromatography, electrophoresis, HPLC, immunoadsorbent techniques, affinity chromatography, immunoprecipitation, and the like.

For example, one method for obtaining the intracellular polypeptides of the present invention involves affinity purification, such as by immunoaffinity chromatography using antibodies (e.g., previously generated antibodies), or by lectin affinity chromatography. Particularly preferred lectin resins are those that recognize mannose moieties such as but not limited to resins derived from *Galanthus nivalis* agglutinin (GNA), *Lens culinaris* agglutinin (LCA or lentil lectin), *Pisum sativum* agglutinin (PSA or pea lectin), *Narcissus pseudonarcissus* agglutinin (NPA) and *Allium ursinum* agglutinin (AUA). The choice of a suitable affinity resin is within the skill in the art. After affinity purification, the polypeptides can be further purified using conventional techniques well known in the art, such as by any of the techniques described above.

Peptide reagents can be conveniently synthesized chemically, for example by any of several techniques that are known to those skilled in the peptide art. In general, these methods employ the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. See, e.g., J. M. Stewart and J. D. Young, *Solid Phase Peptide Synthesis* (Pierce Chemical Co., Rockford, Ill. 1984) and G. Barany and R. B. Merrifield, *The Peptides: Analysis, Synthesis, Biology*, editors E. Gross and J. Meienhofer, Vol. 2, (Academic Press, New York, 1980), pp. 3-254, for solid phase peptide synthesis techniques; and M. Bodansky, *Principles of Peptide Synthesis*, (Springer-Verlag, Berlin 1984) and E. Gross and J. Meienhofer, Eds., *The Peptides: Analysis, Synthesis Biology*, Vol. 1, for classical solution synthesis. These methods are typically used for relatively small polypeptides, i.e.; up to about 50-100 amino acids in length, but are also applicable to larger polypeptides.

Typical protecting groups include t-butyloxycarbonyl (Boc), 9-fluorenylmethoxycarbonyl(Fmoc)benzyloxycarbonyl(Cbz); p-toluenesulfonyl(Tx); 2,4-dinitrophenyl; benzyl (Bzl); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like.

Typical solid supports are cross-linked polymeric supports. These can include divinylbenzene cross-linked-styrene-based polymers, for example, divinylbenzene-hydroxymethylstyrene copolymers, divinylbenzene-chloromethylstyrene copolymers and divinylbenzene-benzhydrylaminopolystyrene copolymers.

Synthesis of peptoid containing polymers can be carried out according to, e.g., U.S. Pat. Nos. 5,877,278; 6,033,631; Simon et al. (1992) *Proc. Natl. Acad. Sci. USA* 89:9367.

The peptide reagent of the present invention can also be chemically prepared by other methods such as by the method of simultaneous multiple peptide synthesis. See, e.g., Houghten *Proc. Natl. Acad. Sci. USA* (1985) 82:5131-5135; U.S. Pat. No. 4,631,211.

IV. Antibodies

In addition, the peptide reagents described herein used in the invention can be used to generate antibodies. In certain embodiments, the antibodies raised against these peptide reagents are specific for pathogenic prions. In other embodiments, the antibodies bind to both pathogenic and non-pathogenic forms. In still further embodiments, the antibodies are specific for nonpathogenic isoforms. Optionally, the antibodies described herein inhibit conversion of the non-pathogenic form to the pathogenic conformation. Typically, the antibodies of the invention are generated by administering a peptide reagent as described herein (or polynucleotide encoding such a peptide reagent) to an animal. The methods may also include isolating the antibodies from the animal.

The antibodies of the invention may be polyclonal or monoclonal antibody preparations, monospecific antisera, human antibodies, or may be hybrid or chimeric antibodies, such as humanized antibodies, altered antibodies (Fab')$_2$ fragments, F(ab) fragments, Fv fragments, single-domain antibodies, dimeric or trimeric antibody fragments or constructs, minibodies, or functional fragments thereof which bind to the antigen in question.

Antibodies are produced using techniques well known to those of skill in the art and disclosed in, for example, U.S. Pat. Nos. 4,011,308; 4,722,890; 4,016,043; 3,876,504; 3,770,380; and 4,372,745. For example, polyclonal antibodies are generated by immunizing a suitable animal, such as a mouse, rat, rabbit, sheep, or goat, with an antigen of interest (e.g., a peptide reagent as described herein). In order to enhance immunogenicity, the antigen can be linked to a carrier prior to immunization. Such carriers are well known to those of ordinary skill in the art. Immunization is generally performed by mixing or emulsifying the antigen in saline, preferably in an adjuvant such as Freund's complete adjuvant, and injecting the mixture or emulsion parenterally (generally subcutaneously or intramuscularly). The animal is generally boosted 2-6 weeks later with one or more injections of the antigen in saline, preferably using Freund's incomplete adjuvant. Antibodies may also be generated by in vitro immunization, using methods known in the art. Polyclonal antiserum is then obtained from the immunized animal.

Monoclonal antibodies are generally prepared using the method of Kohler and Milstein (1975) *Nature* 256:495-497, or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the antigen. B-cells, expressing membrane-bound immunoglobulin specific for the antigen, will bind to the plate, and are not rinsed away with the rest of the suspension. Resulting B-cells, or all dissociated spleen cells, are then induced to fuse with myeloma cells for form hybridomas, and are cultured in a selective medium (e.g., hypoxanthine, aminopterin, thymidine medium, "HAT"). The resulting hybridomas are plated by limiting dilution, and are assayed for the production of antibodies that bind specifically to the immunizing antigen (and which do not bind to unrelated antigens). The selected monoclonal antibody-secreting hybridomas are then cultured either in vitro (e.g., in tissue culture bottles or hollow fiber reactors), or in vivo (e.g., as ascites in mice).

Humanized and chimeric antibodies are also useful in the invention. Hybrid (chimeric) antibody molecules are generally discussed in Winter et al. (1991) *Nature* 349: 293-299 and U.S. Pat. No. 4,816,567. Humanized antibody molecules are generally discussed in Riechmann et al. (1988) *Nature* 332: 323-327; Verhoeyan et al. (1988) *Science* 239:1534-1536; and U.K. Patent Publication No. GB 2,276,169, published 21 Sep. 1994). One approach to engineering a humanized antibody involves cloning recombinant DNA containing the promoter, leader, and variable-region sequences from a mouse antibody gene and the constant-region exons from a human antibody gene to create a mouse-human antibody, a humanized antibody. See generally, Kuby, "Immunology, $3^{rd}$ Edition", W.H. Freeman and Company, New York (1998) at page 136.

Antibodies, both monoclonal and polyclonal, which are directed against peptide reagents as described herein are particularly useful in diagnosis and therapeutic applications, for example, those antibodies that are neutralizing are useful in passive immunotherapy. Monoclonal antibodies, in particular, may be used to raise anti-idiotype antibodies.

Anti-idiotype antibodies are immunoglobulins that carry an "internal image" of the antigen of the agent against which protection is desired. Techniques for raising anti-idiotype antibodies are known in the art. See, e.g., Grzych (1985), Nature 316:74; MacNamara et al. (1984), Science 226:1325, Uytdehaag et al (1985), J. Immunol. 134:1225. These anti-idiotype antibodies may also be useful for treatment and/or diagnosis of conformational diseases.

Antibody fragments are also included within the scope of the invention. A number of antibody fragments are known in the art that comprise antigen-binding sites capable of exhibiting immunological binding properties of an intact antibody molecule. For example, functional antibody fragments can be produced by cleaving a constant region, not responsible for antigen binding, from the antibody molecule, using e.g., pepsin, to produce F(ab')$_2$ fragments. These fragments will contain two antigen binding sites, but lack a portion of the constant region from each of the heavy chains. Similarly, if desired, Fab fragments, comprising a single antigen binding site, can be produced, e.g., by digestion of polyclonal or monoclonal antibodies with papain. Functional fragments, including only the variable regions of the heavy and light chains, can also be produced, using standard techniques such as recombinant production or preferential proteolytic cleavage of immunoglobulin molecules. These fragments are known as $F_v$. See, e.g., Inbar et al. (1972) *Proc. Nat. Acad. Sci USA* 69:2659-2662; Hochman et al. (1976) *Biochem* 15:2706-2710; and Ehrlich et al. (1980) *Biochem* 19:4091-4096.

A single-chain Fv ("sFv" or "scFv") polypeptide is a covalently linked $V_H$-$V_L$ heterodimer that is expressed from a gene fusion including $V_H$- and $V_L$- encoding genes linked by a peptide-encoding linker. Huston et al. (1988) *Proc. Nat. Acad. Sci. USA* 85:5879-5883. A number of methods have been described to discern and develop chemical structures (linkers) for converting the naturally aggregated, but chemically separated, light and heavy polypeptide chains from an antibody V region into an sFv molecule which will fold into a three dimensional structure substantially similar to the structure of an antigen-binding site. See, e.g., U.S. Pat. Nos. 5,091,513; 5,132,405; and 4,946,778. The sFv molecules may be produced using methods described in the art. See, e.g., Huston et al. (1988) *Proc. Nat. Acad. Sci USA* 85:5879-5338; U.S. Pat. Nos. 5,091,513; 5,132,405 and 4,946,778. Design criteria include determining the appropriate length to span the distance between the C-terminus of one chain and the N-terminus of the other, wherein the linker is generally formed from small hydrophilic amino acid residues that do not coil or form secondary structures. Such methods have been described in the art. See, e.g., U.S. Pat. Nos. 5,091,513; 5,132.405 and 4,946,778. Suitable linkers generally comprise polypeptide chains of alternating sets of glycine and serine residues, and may include glutamic acid and lysine residues inserted to enhance solubility.

"Mini-antibodies" or "minibodies" will also find use with the present invention. Minibodies are sFv polypeptide chains that include oligomerization domains at their C-termini, separated from the sFv by a hinge region. Pack et al., (1992) *Biochem* 31:1579-1584. The oligomerization domain comprises self-associating α-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al., (1992) *Biochem* 31:1579-1584; Cumber et al. (1992) *J. Immunology* 149B:120-126.

Non-conventional means can also be used to generate and identify antibodies. For example, a phage display library can be screened for antibodies that bind more to pathogenic forms than non-pathogenic forms or vice versa. See generally, Siegel, "Recombinant Monoclonal Antibody Technology", *Transfus. Clin. Biol.* (2002) 9(1): 15-22; Sidhu, "Phage Display in Pharmaceutical Biotechnology", *Curr. Opin. Biotechnol.* (2000) 11(6):610-616; Sharon, et al., "Recombinant Polyclonal Antibody Libraries", *Comb. Chem. High Throughput Screen* (2000) 3(3): 185-196; and Schmitz et al., "Phage Display: A Molecular Tool for the Generation of Antibodies—Review", *Placenta*, (2000) 21 SupplA: S106-12.

As noted above, the antibodies may also be generated by administering a polynucleotide sequence encoding a peptide reagent as described herein into an animal. When the peptide is expressed in vivo, antibodies are generated in vivo. Methods for polynucleotide delivery are discussed in below.

The specificity of the antibodies of the invention can be tested as described above for peptide reagents. As mentioned above, prions having a pathogenic conformation are generally resistant to certain proteases, such as proteinase K. The same proteases are able to degrade prion a non-pathogenic conformation. One method of testing the specificity of the antibodies of the present invention is to select a biological sample containing both pathogenic and non-pathogenic prions. The sample can be separated into two equal volumes. Antibodies of the invention can be added adsorbed onto a solid support (as further described below) and used to obtain a quantitative value directly related to the number of antibody-prion binding interactions on the solid support. Protease can be added to the second sample and the same test performed. Because the protease in the second sample will degrade any non-pathogenic prions, any antibody-prion binding interactions in the second sample can be attributed to pathogenic prions. Variations and other assays known in the art can also be used to demonstrate the specificity of the antibodies of the invention.

V. Assays

The peptide reagents of the invention can be used in a variety of assays to screen samples (e.g., biological samples such as blood, brain, spinal cord, CSF or organ samples), for example to detect the presence or absence of pathogenic forms of conformational disease proteins in these samples. Unlike many current prion diagnostic reagents, the peptide reagents described herein will allow for detection in virtually any type of biological or non-biological sample, including blood sample, blood products or biopsy samples.

The invention thus provides a method for detecting the presence of a pathogenic prion in a sample comprising: contacting the sample suspected of containing a pathogenic prion with a peptide reagent of the invention under conditions that allow the binding of the peptide reagent to the pathogenic prion protein, if present; and detecting the presence the pathogenic prion, if any, in the sample by its binding to the peptide reagent.

For use in the method of the invention, the sample can be anything known to, or suspected of, containing a pathogenic prion protein. The sample can be a biological sample (that is, a sample prepared from a living or once-living organism) or a non-biological samples include, but are not limited to, organs, whole blood, blood fractions, blood components, plasma, platelets, serum, cerebrospinal fluid (CSF), brain tissue, nervous system tissue, muscle tissue, bone marrow, urine, tears, non-nervous system tissue, organs, and/or biopsies or necropsies. Preferred biological samples include whole blood, blood fractions, blood components, plasma, platelets, and serum.

The sample is contacted with one or more peptide reagents of the invention under conditions that allow the binding of the peptide reagent(s) to the pathogenic prion protein if it is present in the sample. It is well within the competence of one of ordinary skill in the art to determine the particular conditions based on the disclosure herein. Typically, the sample and the peptide reagent(s) are incubated together in a suitable buffer at about neutral pH (e.g., a TBS buffer at pH 7.5) at a suitable temperature (e.g., about 4° C.), for a suitable time period (e.g., about 1 hour to overnight) to allow the binding to occur.

The presence of pathogenic prion protein in the sample is detected by its binding to the peptide reagent(s). Detection of the presence of the pathogenic prion protein by its binding to the peptide reagent(s) of the invention can be accomplished in a number of ways. For example, the peptide reagent(s) of the invention can be used to specifically "capture" the pathogenic prion protein by the formation of a first complex between the peptide reagent(s) and the pathogenic prion protein which first complex can be separated from the unbound sample materials, including any nonpathogenic prion protein present in the sample. The pathogenic prion protein can then be detected by the addition and binding of one or more peptide reagents of the invention, which peptide reagents have been detectably labeled (i.e., labeled peptide reagent(s)). The pathogenic prion protein can be detected while in the first complex, or the pathogenic prion protein can be dissociated from the first complex before the addition of and binding to the labeled peptide reagent(s) of the invention.

Alternatively, when the peptide reagent(s) of the invention are used to capture the pathogenic prion protein as described above, and the first complex is separated from the unbound sample materials, a detectably-labeled prion-binding reagent can be used to detect the pathogenic prion protein, either while the pathogenic prion protein is in the first complex or after the dissociation of the pathogenic prion protein from the first complex. A "prion-binding reagent" is a reagent that binds to a prion protein in any conformation, typically the prion-binding reagent will bind to a denatured form of the prion protein. Such reagents have been described and include, for example, anti-prion antibodies (described, inter alia, in Peretz et al. 1997 J. Mol. Biol. 273: 614; Peretz et al. 2001 Nature 412:739; Williamson et al. 1998 J. Virol. 72:9413; U.S. Pat. No. 6,765,088; U.S. Pat. No. 6,537548), motif-grafted hybrid polypeptides (see, WO03/085086), certain cationic or anionic polymers (see, WO03/073106), certain peptides that are "propagation catalysts" (see, WO02/0974444) and plasminogen. It will be apparent that if the particular prion-binding reagent used binds to a denatured form of the prion that the "captured" pathogenic prion protein should be denatured prior to detection with the prion-binding reagent.

In another alternative, a prion-binding reagent can be used to capture any prions (pathogenic or nonpathogenic) present in the sample to form a first complex, and one or more detectably-labeled peptide reagent(s) of the invention can be used to detect the pathogenic prions in the first complex or after dissociation from the first complex.

In a further alternative, the sample can be captured directly (i.e., without any prion-binding reagent) onto a solid support and the pathogenic prion proteins, if present, can be detected using one or more detectably labeled peptide reagent(s) of the invention.

The above-described capture and detection steps can be carried out in solution or can be carried out in or on a solid support, or some combination of solution and solid phase. Some suitable solution phase formats include for example, fluoresecence correlation spectroscopy (see, Giese et al. *Arch. Virol. Suppl.* 2000 16:161; Bieschke et al. *Proc. Natl. Acad. Sci. USA* 2000 97:55468) and fluoresecence resonance energy transfer. Typically, the peptide reagent(s) of the invention will be detectably labeled in these solution phase formats. Preferably, the peptide reagent(s) will be labeled with two or more distinguishable detectable labels. The presence of a pathogenic prion protein can be detected by the coincidence of two or more detectable labels in a first complex. Suitable solid phase assay formats are described herein. In general, for solid phase formats, the capture reagent (which can be one or more of the peptide reagents of the invention, or one or more prion-binding reagents) is attached, or adapted for attachment, to a solid support. The capture reagent can be adapted for attachment to a solid support by any means known in the art, for example, the capture reagent and the solid support can each comprise one member of a binding pair, such that when the capture reagent is contacted with the solid support the capture reagent is attached to the solid support through the binding of the members of the binding pair. For example, the capture reagent can comprise biotin and the support can comprise avidin or streptavidin. In addition to biotin-avidin and biotin-streptavidin, other suitable binding pairs for this embodiment include, for example, antigen-antibody, hapten-antibody, mimetope-antibody, receptor-hormone, receptor-ligand, agonist-antagonist, lectin-carbohydrate, Protein A-antibody Fc. Such binding pairs are well known (see, e.g., U.S. Pat. Nos. 6,551,843 and 6,586,193) and one of ordinary skill in the art would be competent to select suitable binding pairs and adapt them for use with the present invention. When the capture reagent is adapted for attachment to the support as described above, the sample can be contacted with the capture reagent before or after the capture reagent is attached to the support.

The invention thus provides a method for detecting the presence of a pathogenic prion in a sample comprising:
(a) contacting a sample suspected of containing a pathogenic prion with a first peptide reagent under conditions that allow the binding of the first peptide reagent to the pathogenic prion protein, if present, to form a first complex; and
(b) detecting the presence the pathogenic prion, if any, in the sample by its binding to the first peptide reagent.

The peptide reagent is as described herein, preferably the peptide reagent is derived from a peptide having a sequence of SEQ ID NO:12-132, more preferably, from a peptide having a sequence of one of SEQ ID NO: SEQ ID NO: 66, 67, 68, 72, 81, 96, 97, 98, 107, 108, 119, 120, 121, 122, 123, 124, 125, 126, 127, 129, 130, 131, 132; or from peptides having SEQ ID NO: 14, 35, 36, 37, 40, 50, 51, 77, 89, 100, 101, 109, 110, 111, 112, 113, 114, 115, 116, 117, 118 or 128; or from peptide shaving SEQ ID NO: 56, 57, 65, 82, or 84. The peptide reagent can be biotinylated. The peptide reagent can be attached to a solid support. In some embodiments, the peptide reagent can be detectably labeled.

The invention also provides a method for detecting the presence of a pathogenic prion in a sample comprising:
(a) contacting a sample suspected of containing a pathogenic prion with a first peptide reagent under conditions that allow the binding of the first peptide reagent to the pathogenic prion, if present, to form a first complex;
(b) contacting said first complex with a second peptide reagent under conditions that allow the binding of the second peptide reagent to the pathogenic prion in said first complex, wherein said second peptide reagent comprises a detectable label; and
(c) detecting the presence the pathogenic prion, if any, in the sample by its binding to the second peptide reagent.

When the method utilizing a first peptide reagent and a second peptide reagent, the first and second peptide reagents can be the same or different. By "the same" is meant that the first and second peptide reagents differ only in the inclusion of a detectable label in the second peptide reagent.

The first peptide reagent and the second peptide reagent can be derived from peptide fragments from the same region of a prion protein or from peptide fragments from a different region of a prion protein. The first peptide reagent and the second peptide reagent can each be independently selected from peptide reagents derived from peptides having SEQ ID NO: 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, or 132.

The first peptide reagent and the second peptide reagent can each independently be selected from a peptide reagent derived from peptides having SEQ ID NO:66, 67, 68, 72, 81, 96, 97, 98, 107, 108, 119, 120, 121, 122, 123, 124, 125, 126, 127, 14, 35, 36, 37, 40, 50, 51, 77, 89, 100, 101, 109, 110, 111, 112, 113, 114, 115, 116, 117, 118, 128, 129, 130, 131, 132, 56, 57, 65, 82, and 84.

The first peptide reagent can be selected from a peptide reagent derived from peptides having SEQ ID NO:66, 67, 68, 72, 81, 96, 97, 98, 107, 108, 119, 120, 121, 122, 123, 124, 125, 126, or 127, and the second peptide reagent can be selected from peptide reagent derived from peptides having SEQ ID NO: 14, 35, 36, 37, 40, 50, 51, 77, 89, 100, 101, 109, 110, 111, 112, 113, 114, 115, 116, 117, 118, 128, 129, 130, 131, or 132, or vice versa. The first peptide reagent can be selected from a peptide reagent derived from peptides having SEQ ID NO:66, 67, 68, 72, 81, 96, 97, 98, 107, 108, 119, 120, 121, 122, 123, 124, 125, 126, or 127, and the second peptide reagent can be selected from peptide reagent derived from peptides having SEQ ID NO: 56, 57, 65, 82, and 84, or vice versa. The first peptide reagent can be selected from a peptide reagent derived from peptides having SEQ ID NO: 14, 35, 36, 37, 40, 50, 51, 77, 89, 100, 101, 109, 110, 111, 112, 113, 114, 115, 116, 117, 118, 128, 129, 130, 131, or 132, and the second peptide reagent can be selected from peptide reagent derived from peptides having SEQ ID NO: 56, 57, 65, 82, and 84, or vice versa.

The first peptide reagent can be biotinylated and may be attached to a solid support.

The invention also provides a method for detecting the presence of a pathogenic prion in a sample comprising:
(a) contacting a sample suspected of containing a pathogenic prion with a first peptide reagent under conditions that allow the binding of the first peptide reagent to the pathogenic prion, if present, to form a first complex;
(b) removing unbound sample materials;
(c) dissociating said pathogenic prion from said first complex;
(d) contacting said dissociated pathogenic prion with a second peptide reagent under conditions that allow the binding of the second peptide reagent to the pathogenic prion, wherein said second peptide reagent comprises a detectable label; and
(e) detecting the presence the pathogenic prion, if any, in the sample by its binding to the second peptide reagent. The first and second peptide reagents can be the same or different.

The invention also provides a method for detecting the presence of a pathogenic prion in a sample comprising:
(a) contacting a sample suspected of containing a pathogenic prion with a first peptide reagent under conditions that allow the binding of the first peptide reagent to the pathogenic prion, if present, to form a first complex;
(b) removing unbound sample materials;
(c) dissociating said pathogenic prion from said first complex;
(d) contacting said dissociated pathogenic prion with a prion-binding reagent under conditions that allow the binding of the prion-binding reagent to the pathogenic prion, wherein said prion-binding reagent comprises a detectable label; and
(e) detecting the presence the pathogenic prion, if any, in the sample by its binding to the prion-binding reagent. The prion-binding reagent can be an anti-prion antibody, motif-grafted hybrid polypeptide, cationic or anionic polymers, propagation catalysts and plasminogen, or any other moiety known to bind prion proteins.

The invention also provides a method for detecting the presence of a pathogenic prion in a sample comprising:
(a) contacting a sample suspected of containing a pathogenic prion with a prion-binding reagent under conditions that allow the binding of the prion-binding reagent to the pathogenic prion, if present, to form a first complex;
(b) removing unbound sample materials;
(c) contacting said first complex with a peptide reagent under conditions that allow the binding of the peptide reagent to the pathogenic prion, wherein said peptide reagent comprises a detectable label; and
(d) detecting the presence the pathogenic prion, if any, in the sample by its binding to the peptide reagent.

The invention also provides a method for detecting a pathogenic prion in a sample, comprising:
(a) providing a solid support comprising first peptide reagent
(b) contacting the solid support with a sample under conditions which allow pathogenic prions, when present in the sample, to bind to the first peptide reagent;
(c) contacting the solid support with a detectably labeled second peptide reagent under conditions which allow the second peptide reagent to bind to pathogenic prions bound by the first peptide reagent; and,
(d) detecting complexes formed between the first peptide reagent, a pathogenic prion from the sample and the second peptide reagent, thereby detecting the presence of the pathogenic prion in the sample.

Alternatively the prion-binding reagent can be provided on the solid support. The invention thus provides a method for detecting the presence of a pathogenic prion in a sample comprising:
(a) providing a solid support comprising a prion-binding reagent;
(b) contacting the solid support to a sample under conditions which allow prion proteins, when present in the sample, to bind to the prion-binding reagent;
(c) contacting the solid support to a detectably labeled second peptide reagent; and
(d) detecting complexes formed between the prion-binding reagent, a pathogenic prion from the biological sample, and the second peptide reagent.

The assay can be provided in a competitive format; thus the invention provides a method for detecting the presence of a pathogenic prion in a sample comprising:
(a) providing a solid support comprising a first peptide reagent;
(b) combining the solid support with a detectably labeled first ligand, wherein the first peptide reagent's binding affinity to the detectably labeled first ligand is weaker than the first peptide reagent's binding affinity to a pathogenic prion;
(c) combining a sample with the solid support under conditions which allow a pathogenic prion, when present in the sample, to bind to the first peptide reagent and replace the first ligand;
(d) detecting complexes formed between the first peptide reagent and the pathogenic prion from the sample.

Generally, peptide reagents as described herein are used to bind to prion proteins in a sample (e.g., as a capture reagent) and/or to detect the presence of prion proteins (e.g., as a detection reagent). The capture reagent and detection reagent may be separate molecules or, alternatively one molecule may serve both capture and detection functions. In certain embodiments, the capture and/or detection reagents are peptide reagents described herein that interact preferentially with pathogenic prions (i.e., are pathogenic-prion specific). In other embodiments, the capture reagent is specific for pathogenic prions and the detection reagent binds to both pathogenic and nonpathogenic forms, for example antibodies that bind to prion proteins. Such prion-binding reagents have been described above herein. Alternatively, in other embodiments, the capture reagent is not specific for pathogenic prions and the detection reagent is specific for pathogenic prions.

Any suitable means of detection can then be used to identify binding between a peptide reagent as described herein and a prion protein. For example, assays as described herein may involve the use of labeled peptide reagents or antibodies. Detectable labels suitable for use in the invention include any molecule capable of detection, including, but not limited to, radioactive isotopes, fluorescers, chemiluminescers, chromophores, fluorescent semiconductor nanocrystals, enzymes, enzyme substrates, enzyme cofactors, enzyme inhibitors, chromophores, dyes, metal ions, metal sols, ligands (e.g., biotin, strepavidin or haptens) and the like. Additional labels include, but are not limited to, those that use fluorescence, including those substances or portions thereof that are capable of exhibiting fluorescence in the detectable range. Particular examples of labels that may be used in the invention include, but are not limited to, horse radish peroxidase (HRP), fluorescein, FITC, rhodamine, dansyl, umbelliferone, dimethyl acridinium ester (DMAE), Texas red, luminol, NADPH and β-galactosidase. In addition, the detectable label may include an oligonucleotide tag, which tag can be detected by any known method of nucleic acid detection including PCR, TMA, b-DNA, NASBA, etc.

In addition to the use of labeled detection reagents (described above), immunoprecipitation may be used to separate out peptide reagents that are bound to the prion protein (e.g., pathogenic prion). Preferably, the immunoprecipitation is facilitated by the addition of a precipitating enhancing agent. A precipitation-enhancing agent includes moieties that can enhance or increase the precipitation of the peptide reagents that are bound to pathogenic prions. Such precipitation enhancing agents include polyethylene glycol (PEG), protein G, protein A and the like. Where protein G or protein A are used as precipitation enhancing agents, the protein can optionally be attached to a bead, preferably a magnetic bead. Precipitation can be further enhanced by use of centrifugation or with the use of magnetic force. Use of such precipitating enhancing agents is known in the art.

Assays that amplify the signals from the detection reagent are also known. Examples of which are assays that utilize biotin and avidin, and enzyme-labeled and mediated immunoassays, such as ELISA assays.

One or more of the steps of the assays described herein may be conducted in solution (e.g., a liquid medium) or on a solid support. A solid support, for purposes of the invention, can be any material that is an insoluble matrix and can have a rigid or semi-rigid surface to which a molecule of interest (e.g., peptide reagents of the invention, prion proteins, antibodies, etc) can be linked or attached. Exemplary solid supports include, but are not limited to, substrates such as nitrocellulose, polyvinylchloride; polypropylene, polystyrene, latex, polycarbonate, nylon, dextran, chitin, sand, silica, pumice, agarose, cellulose, glass, metal, polyacrylamide, silicon, rubber, polysaccharides, polyvinyl fluoride; diazotized paper; activated beads, magnetically responsive beads, and any materials commonly used for solid phase synthesis, affinity separations, purifications, hybridization reactions, immunoassays and other such applications. The support can be particulate or can be in the form of a continuous surface and includes membranes, mesh, plates, pellets, slides, disks, capillaries, hollow fibers, needles, pins, chips, solid fibers, gels (e.g. silica gels) and beads, (e.g., pore-glass beads, silica gels, polystyrene beads optionally cross-linked with divinylbenzene, grafted co-poly beads, polyacrylamide beads, latex beads, dimethylacrylamide beads optionally crosslinked with N-N'-bis-acryloylethylenediamine, iron oxide magnetic beads, and glass particles coated with a hydrophobic polymer.

Peptide reagents as described herein can be readily coupled to the solid support using standard techniques. Immobilization to the support may be enhanced by first coupling the peptide reagent to a protein (e.g., when the protein has better solid phase-binding properties). Suitable coupling proteins include, but are not limited to, macromolecules such as serum albumins including bovine serum albumin (BSA), keyhole limpet hemocyanin, immunoglobulin molecules, thyrogiobuline, ovalbumin, and other proteins well known to those skilled in the art. Other reagents that can be used to bind molecules to the support include polysaccharides, polylactic acids, polyglycolic acids, polymeric amino acids, amino acid copolymers, and the like. Such molecules and methods of coupling these molecules to proteins, are well known to those of ordinary skill in the art. See, e.g., Brinkley, M. A., (1992) *Bioconjugate Chem.*, 3:2-13; Hashida et al. (1984) *J. Appl. Biochem.*, 6:56-63; and Anjaneyulu and Staros (1987) *International J. of Peptide and Protein Res.* 30:117-124.

If desired, the molecules to be added to the solid support can readily be functionalized to create styrene or acrylate moieties, thus enabling the incorporation of the molecules into polystyrene, polyacrylate or other polymers such as polyimide, polyacrylamide, polyethylene, polyvinyl, polydiacetylene, polyphenylene-vinylene, polypeptide, polysaccharide, polysulfone, polypyrrole, polyimidazole, polythiophene, polyether, epoxies, silica glass, silica gel, siloxane, polyphosphate, hydrogel, agarose, cellulose and the like.

The peptide reagents can be attached to the solid support through the interaction of a binding pair of molecules. Such binding pairs are well known and examples are described elsewhere herein. One member of the binding pair is coupled by techniques described above to the solid support and the other member of the binding pair is attached to the peptide reagent (before, during, or after synthesis). The peptide reagent thus modified can be contacted with the sample and interaction with the pathogenic prion, if present, can occur in solution, after which the solid support can be contacted with the peptide reagent (or peptide-prion complex). Preferred binding pairs for this embodiment include biotin and avidin, and biotin and streptavidin.

Suitable controls can also be used in the assays of the invention. For instance, a negative control of $PrP^C$ can be used in the assays. A positive control of $PrP^{Sc}$ (or PrPres) could also be used in the assays. Such controls can optionally be detectably labeled.

Several variations and combinations using the peptide reagents of the invention may be applied in the assays of the invention. The following non-limiting examples are described for illustration.

In certain embodiments, assays are described for detecting pathogenic prions in a biological sample. In such methods, the peptide reagent of the invention can be used a s a capture reagent for pathogenic prions in a biological or a non-bioligical sample. In on such embodiment, a solid support (e.g., magnetic beads) is first reacted with a peptide reagent as described herein that interacts preferentially with pathogenic prions such that the peptide reagent is sufficiently immobilized to the support. The solid support is then contacted with a sample suspected of containing pathogenic prions under conditions that allow the peptide reagent to bind to pathogenic prions. Following removal of the unbound sample material, the bound pathogenic prions can be dissociated from the peptide reagent and detected using any known detection mechanism, including but not limited to Western Blot and ELISA, for example, as described below in the Examples and references cited therein. Alternatively, the bound pathogenic prion can be detected without dissociation from the peptide reagent.

Alternatively, the peptide reagent of the invention may be contacted with the sample suspected of containing pathogenic prions before being attached to the solid support, followed by attachment of the peptide reagent to the solid support (for example, the peptide reagent can be biotinylated and the solid support comprise avidin or streptavidin). Following removal of the unbound sample material, the pathogenic prions may be dissociated from the peptide reagent and detected using any known detection mechanism, including but not limited to Western Blot and ELISA, for example, as described below in the Examples and references cited therein. Alternatively, the pathogenic prions need not be dissociated from the peptide reagent prior to detection.

Detection of the pathogenic prions in the sample may be accomplished by using a peptide reagent as described herein, that interacts preferentially with pathogenic forms. Alternatively, pathogenic prions may be detected by non-specific detection reagents (e.g., peptides or antibodies that bind to PrP generally). In certain embodiments, following dissociation from the solid support, the captured pathogenic prion is denatured prior to detection, which may facilitate detection by allowing the use of nonspecific detection reagents. Alternatively, the captured pathogenic prion can be denatured without dissociation from the peptide reagent if, for example, the peptide reagent is modified to contain an activatable reactive group (e.g., a photoreactive group) that can be used to covalently link the peptide reagent and the pathogenic prion.

Protocols such as ELISAs as described in Ryou et al. (2003) *Lab Invest.* 83(6):837-43 can be performed to quantify that amount of pathogenic prion eluted from the solid support. (See, Examples). Briefly, the wells of a microtiter plate are coated with the captured pathogenic prion that has been dissociated (eluted) from the solid support. The plate(s) can be washed to remove unbound moieties and a detectably labeled binding molecule, such as a anti-prion antibody or a peptide reagent of the invention (either the same one used for capture or a different one) is added. This binding molecule is allowed to react with any captured sample prion, the plate washed and the presence of the labeled antibodies and/or labeled peptide reagents detected using methods well known in the art. The binding molecule need not be specific for the pathogenic prion form but can bind to both isoforms or a denatured PrP, as long as the capture reagent is specific for the pathogenic prion form.

In other exemplary assays, the capture reagent and prion are not dissociated prior to detection. For example, a solid support (e.g., the wells of a microtiter plate) is linked to a first pathogenic-prion specific molecule (peptide reagent). A biological sample containing or suspected of containing pathogenic prions is then added to the solid support. After a period of incubation sufficient to allow any pathogenic prions to bind to the first molecule, the solid support can be washed to remove unbound moieties and a detectably labeled secondary binding molecule as described above, such as a second anti-PrP antibody or a prion-specific peptide reagent, added. Alternatively, a molecule that binds to pathogenic and non-pathogenic forms (e.g., nonspecific capture reagent) can be coupled to a solid support (e.g., coated onto the wells of a microtiter plate) and detection can be accomplished using a pathogenic prion-specific detection reagent (e.g., peptide reagent described herein).

Another exemplary assay is a "two peptide sandwich" assay can be used to detect prions (e.g., pathogenic prions). In this technique, the solid support is reacted with one or more first peptide reagents of the invention as described herein, washed to remove unreacted first peptide reagent and then exposed to the test sample (e.g., a biological sample) suspected of containing a pathogenic prion protein under conditions that allow interaction between the first peptide reagent(s) and any pathogenic prion protein present in the sample. Unreacted sample components are removed and one or more second peptide reagents of the invention are added under conditions that allow interaction of the second peptide reagent(s) to interact with any pathogenic prion protein present. The interaction between first peptide-prion protein-second peptide can be detected by any means that are known in the art. Typically the second peptide reagent(s) comprise a detectable label. For this assay, the first peptide reagent(s) and/or the second peptide reagent(s) interact preferentially with a pathogenic prion protein.

In certain embodiments, anti-PrP antibodies are used to detect prion proteins. Antibodies, modified antibodies and other reagents, that bind to prions, particularly to $PrP^C$ or to the denatured PrP, have been described and some of these are available commercially (see, e.g., anti-prion antibodies described in Peretz et al. 1997 J. Mol. Biol. 273: 614; Peretz et al. 2001 Nature 412:739; Williamson et al. 1998 J. Virol. 72:9413; U.S. Pat. No. 6,765,088. Some of these and others are available commercially from, inter alia, InPro Biotechnology, South San Francisco, Calif., Cayman Chemicals, Ann Arbor Mich.; Prionics AG, Zurich; also see, WO 03/085086 for description of modified antibodies).

The peptide reagents of the invention may also be used in competition assays. Means of detection can be used to identify when a ligand weakly binds to $PrP^{Sc}$ is displaced by a peptide reagent described herein that is specific for $PrP^{Sc}$. For instance a sample suspected of containing $PrP^{Sc}$ may be adsorbed onto a solid support. Subsequently, the solid support is combined with a detectably labeled ligand that binds to $PrP^{Sc}$ (e.g., plasminogen, laminin receptor and heparan sulfate) under conditions such that the detectably labeled ligand binds to $PrP^{Sc}$. The ligand-$PrP^{Sc}$ complexes are detected. A $PrP^{Sc}$-binding peptide reagent as described herein is then added. The binding affinity of the detectably labeled ligand is weaker than the binding affinity of the peptide reagent for a pathogenic prion. Accordingly, the $PrP^{Sc}$-binding peptide reagent will replace the labeled ligand and the decrease in detected amounts of the labeled ligand indicate complexes formed between the peptide reagent and pathogenic prions from the biological sample can be detected.

The above-described assay reagents, including the peptide reagents described herein, can be provided in kits, with suitable instructions and other necessary reagents, in order to conduct detection assays as described above. Where the peptide reagent is adsorbed onto a solid support, the kit may additionally or alternatively comprise such peptide reagents adsorbed onto one or more solid supports. The kit may further contain suitable positive and negative controls, as described above. The kit can also contain, depending on the particular detection assay used, suitable labels and other packaged reagents and materials (i.e., wash buffers and the like).

In still further embodiments, the invention is directed to solid supports comprising a pathogenic prion-specific peptide reagent. Methods of producing these solid supports are also provided, for example by (a) providing a solid support; and (b) binding thereto one or more pathogenic prion-specific peptide reagents.

The prion-specific peptide reagents may further be used to isolate pathogenic prion proteins using affinity supports. The peptide reagents can be affixed to a solid support by, for example, adsorption, covalent linkage, etc. so that the peptide reagents retain their prion-selective binding activity. Optionally, spacer groups may be included, for example so that the binding site of the peptide reagent remains accessible. The immobilized molecules can then be used to bind the pathogenic prion protein from a biological sample, such as blood, plasma, brain, spinal cord, other tissues. The bound peptide reagents or complexes are recovered from the support by, for example, a change in pH or the pathogenic prion may be dissociated from the complex Samples that can be tested according to the invention include any sample amenable to an antibody assay, including samples from nervous system tissue (e.g., brain, spinal cord, CSF, etc.) blood and/or other tissue samples from living or dead subjects. As noted above, in preferred embodiments, the samples are blood, blood product or tissue samples obtained from a living subject.

VI. Additional Applications

A. Detection

As described above, the peptide reagents described herein can be used to diagnose prion disease in a subject. In addition, the peptide reagents described above can also be used to detect pathogenic prion contamination in blood and/or food supplies. Thus, a blood supply can be prepared that is substantially free of pathogenic prions by screening aliquots from individual collected samples or pooled samples using any of the detection assays described herein. Samples or pooled samples that are contaminated with pathogenic prions can be eliminated before they are combined. In this way, a blood supply substantially free of pathogenic prion contamination can be provided. By "substantially free of pathogenic prions" is meant that the present of pathogenic prions is not detected using any of the assays described herein. Importantly, the peptide reagents described herein, which have already been shown to detect pathogenic protein forms in brain tissue diluted $10^6$ fold by normal tissue, are the only demonstrated reagent that may be capable of detecting pathogenic prions in blood.

The invention thus provides a method of preparing blood supply that is substantially free of pathogenic prions, said blood supply comprising whole blood, red blood cells, plasma, platelets or serum, said method comprising:

(a) screening aliquots of whole blood, red blood cells, plasma, platelets or serum from collected blood samples by any of the detection methods provided herein for detecting pathogenic prions;
(b) eliminating samples in which pathogenic prions are detected; and
(c) combining samples in which pathogenic prions are not detected to provide a blood supply that is substantially free of pathogenic prions.

Similarly, the food supply can be screened for the presence of pathogenic prions in order to provide food that is substantially free of pathogenic prions. Thus, using any of the methods described herein, samples from live organisms intended to as food for human or animal consumption can be screened for the presence of pathogenic prions. Samples taken from food product intended to enter the food supply can also be screened. Samples in which pathogenic prions are detected are identified and the live organism or food intended to enter the food supply from which the samples in which pathogenic prions were detected are removed from the food supply. In this way, a food supply that is substantially free of pathogenic prions can be provided.

The invention thus provides a method of preparing food supply that is substantially free of pathogenic prions, said method comprising:

(a) screening a sample collected from live organisms that will enter the food supply or a sample collected from food intended to enter the food supply by any of the detection methods provided herein for detecting pathogenic prions
(b) eliminating samples in which pathogenic prions are detected; and
(c) combining samples in which pathogenic prions are not detected to provide a food supply that is substantially free of pathogenic prions.

B. Purification

The peptides of the invention can also be used remove pathogenic prions from a sample, both for the purpose of isolating the pathogenic prion (e.g., for concentrating the prion protein prior to detection) and for the purpose of eliminating the pathogenic prion from the (e.g, as a means of providing a sample that is substantially free of pathogenic prions. In these methods, the peptide reagents are typically provided on a solid support. The solid support comprising the peptide reagent is contacted with the sample containing the pathogenic prion under conditions to bind the prion to the peptide reagent. If the aim is to isolate the pathogenic prion, the unbound sample is removed and the solid support containing the prions is collected; if the aim is to eliminate the prions from the sample, the unbound sample is collected.

The Invention thus provides a method for isolating a pathogenic prion protein from a sample comprising:

(a) providing a solid support comprising a peptide reagent according to the invention;
(b) contacting said sample with said solid support under conditions that allow the binding of a pathogenic prion protein, if present in said sample, to said first peptide reagent, to form a first complex and
(c) removing unbound sample materials.

In a further embodiment, said pathogenic prion protein may be dissociated from said first complex. This dissociating can be accomplished by techniques that are well known in the protein purification arts.

The invention also provides a method for eliminating pathogenic prion proteins from a sample comprising;

(a) providing a solid support comprising a peptide reagent according to the invention;
(b) contacting said solid support with a sample suspected of containing pathogenic prion proteins under conditions that allow the binding of the pathogenic prion proteins, if present, to the peptide reagent; and
(c) recovering the unbound sample materials.

C. Compositions

The invention further relates to compositions comprising the peptide reagents and/or antibodies described herein (and polynucleotides encoding these peptide reagents and/or antibodies) and methods of using these compositions in therapeutic and prophylactic compositions for the treatment or prevention of prion-related diseases. Furthermore, the antibodies, peptide reagents (and polynucleotides encoding these antibodies and/or peptide reagents) can also be used in compositions, individually or in combination, for prophylactic (i.e., to prevent pathogenesis) or therapeutic (to treat disease following infection) purposes.

The precise mechanism by which the compositions described herein act to treat or prevent disease is not critical.

Without being bound by one theory, the compositions described herein may act to treat or prevent conformation diseases by one or more of the following mechanisms: induction of an immune response in the subject which then treats or prevents the disease state; interaction (e.g., binding) to non-pathogenic forms which may prevent conversion to non-pathogenic forms; binding to pathogenic forms which may prevent pathogenic consequences; and/or binding to pathogenic forms which may prevent the pathogenic forms from converting additional non-pathogenic forms to disease forms. (See, e.g., Peretz et al. (2001) *Nature* 412:739-743 assaying the ability of certain Fabs to inhibit prion propagation).

The compositions can comprise mixtures of one or more of the peptide reagents, antibodies and/or polynucleotides. These molecules may be obtained from a variety of sources, for example, recombinantly produced protein, synthetically produced proteins, etc. The compositions may also be administered in conjunction with other molecules, for example, antigens and immunoregulatory agents such as immunoglobulins, cytokines, lymphokines, and chemokines, including but not limited to IL-2, modified IL-2 (cys125-ser125), GM-CSF, IL-12, alpha- or gamma-interferon, IP-10, MIP1 and RANTES. The compositions may be administered as polypeptides or, alternatively, as naked nucleic acid (e.g., DNA), using viral vectors (e.g., retroviral vectors, adenoviral vectors, adeno-associated viral vectors, alphaviral vectors) or non-viral vectors (e.g., liposomes, particles coated with nucleic acid or protein).

The compositions may also comprise a mixture of peptide reagent and nucleic acid, which in turn may be delivered using the same or different modalities and/or vehicles. The same or different compositions may be given more than once (e.g., a "prime" administration followed by one or more "boosts") to achieve the desired effects. The same composition can be administered as the prime and as the one or more boosts. Alternatively, different compositions can be used for priming and boosting.

The compositions of the invention are preferably pharmaceutically acceptable and pharmacologically acceptable. In particularly, the compositions are preferably not biologically or otherwise undesirable, i.e., the material may be administered to an individual in a formulation or composition without causing any undesirable biological effects or interacting in a deleterious manner with any of the components of the composition in which it is contained.

Compositions as described herein will typically comprise a therapeutically effective amount of the molecules (peptide reagents) or nucleotide sequences encoding the same, antibodies directed to these molecules and any other of the above-mentioned components, as needed. By "therapeutically effective amount" is meant an amount that will induce a protective and/or therapeutic response in the uninfected, infected or unexposed subject to whom it is administered. A "therapeutically effective amount" will fall in a relatively broad range that can be determined through routine trials. The exact amount necessary will vary depending on the subject being treated; the age and general condition of the individual to be treated; the capacity of the individual's immune system to synthesize antibodies; the degree of protection desired; the severity of the condition being treated; the particular composition selected and its mode of administration, among other factors.

In certain embodiments, the peptide reagents are immunogenic and the methods of the invention comprise administering an immunogenic composition comprising a peptide reagent as described herein, an antibody specific for pathogenic prions and/or polynucleotides encoding, these peptide reagents or antibodies to an animal. The immunogenic compositions used in the invention preferably comprise an immunologically effective amount of these components. An "immunologically effective amount" is an amount sufficient to allow the mammal to raise an immune response to a prion protein, preferably a pathogenic prion. The immune response generally results in the development in the subject of a secretory, cellular and/or antibody-mediated immune response. Usually, such a response includes but is not limited to one or more of the following effects; the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell. The amount of antibodies produced will vary depending on several factors including the animal used, the presence of an adjuvant, etc.

The compositions of the invention may further comprise one or more adjuvants. Adjuvants suitable for use in the invention include one or more of the following:

*E. coli* heat-labile enterotoxin ("LT"), or detoxified mutants thereof, such as the K63 or R72 mutants;

cholera toxin ("CT"), or detoxified mutants thereof;

microparticles (i.e., a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(a-hydroxy acid), a polyhydroxybutyric acid, a polyorthoester, a polyanhydride, a polycaprolactone etc.);

a polyoxyethylene ether or a polyoxyethylene ester (see International patent application WO 99/52549);

a polyoxyethylene sorbitan ester surfactant in combination with an octoxynol (see International patent application WO 01/21207) or a polyoxyeyhylene alkyl ether or ester surfactant in combination with at least one additional non-ionic surfactant such as an octoxynol (see International patent application WO 01/21152);

chitosan (e.g. International patent application WO 99/27960)

an immunostimulatory oligonucleotide (e.g. a CpG oligonucleotide) and a saponin (see International patent application WO 00/62800)

immunostimulatory double stranded RNA.

aluminum compounds (e.g. aluminum hydroxide, aluminum phosphate, aluminum hydroxyphosphate, oxyhydroxide, orthophosphate, sulfate etc. (e.g. see chapters 8 & 9 of *Vaccine design: the subunit and adjuvant approach*, eds. Powell & Newman, Plenum Press 1995 (ISBN 0-306-44867-X) (hereinafter "*Vaccine design*"), or mixtures of different aluminum compounds, with the compounds taking any suitable form (e.g. gel, crystalline, amorphous etc.), and with adsorption being preferred;

MF59 (5% Squalene, 0.5% Tween 80, and 0.5% Span 85, formulated into submicron particles using a microfluidizer) (see Chapter 10 of *Vaccine design*; see also International patent application WO 90/14837);

liposomes (see Chapters 13 and 14 of *Vaccine design*);

ISCOMs (see Chapter 23 of *Vaccine design*);

SAF, containing 10% Squalane, 0.4% Tween 80, 5% pluronic-block polymer L121, and thr-MDP, either microfluidized into a submicron emulsion or vortexed to generate a larger particle size emulsion (see Chapter 12 of *Vaccine design*);

Ribi™ adjuvant system (RAS), (Ribi Immunochem) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+ CWS (Detox™);

saponin adjuvants, such as QuilA or QS21 (see Chapter 22 of *Vaccine design*), also known as Stimulon™;

ISCOMs, which may be devoid of additional detergent (International patent application WO 00/07621);

complete Freund's adjuvant (CFA) and incomplete Freund's adjuvant (IFA);

cytokines, such as interleukins (e.g. IL-1, IL-2, IL-4, IL-5, IL-6, IL-7, IL-12, etc.), interferons (e.g. interferon-?), macrophage colony stimulating factor, tumor necrosis factor, etc. (see Chapters 27 & 28 of *Vaccine design*);

monophosphoryl lipid A (MPL) or 3-O-deacylated MPL (3dMPL) (e.g. chapter 21 of *Vaccine design*);

combinations of 3dMPL with, for example, QS21 and/or oil-in-water emulsions (European patent applications 0835318, 0735898 and 0761231);

oligonucleotides comprising CpG motifs (see Krieg (2000) *Vaccine*, 19:618-622; Krieg (2001) *Curr. Opin. Mol. Ther.*, 2001, 3:15-24; WO 96/02555, WO 98/16247, WO 98/18810, WO 98/40100, WO 98/55495, WO 98/37919 and WO 98/52581, etc.) i.e. containing at least one CG dinucleotide, a polyoxyethylene ether or a polyoxyethylene ester (International patent application WO 99/52549);

a polyoxyethylene sorbitan ester surfactant in combination with an octoxynol (International patent application WO 01/21207) or a polyoxyethylene alkyl ether or ester surfactant in combination with at least one additional non-ionic surfactant such as an octoxynol (International patent application WO 01/21152);

an immunostimulatory oligonucleotide (e.g. a CpG oligonucleotide) and a saponin (International patent application WO 00/62800);

an immunostimulant and a particle of metal salt (International patent application WO 00/23105);

a saponin and an oil-in-water emulsion (International patent application WO 99/11241); and a saponin (e.g. QS21)+3dMPL+IL-12 (optionally+a sterol) (International patent application WO 98/57659).

Muramyl peptides include, but are not limited to, N-acetyl-muramyl-L-threonyl-D-isoglutamine (thr-MDP), N-acteyl-normuramyl-L-alanyl-D-isogluatme (nor-MDP), N-acetyl-muramyl-L-alanyl-D-isogluatminyl-L-alanine-2-(1'-2'-dipalmitoyl-sn-glycero-3-huydroxyphosphoryloxy)-ethylamine (MTP-PE), etc.

Other adjuvants suitable for mucosal or parenteral administration are also available (e.g. see chapter 7 of *Vaccine design: the subunit and adjuvant approach*, eds. Powell & Newman, Plenum Press 1995 (ISBN 0-306-44867-X).

Mutants of LT are preferred adjuvants (e.g., mucosal adjuvants), in particular the "K63" and "R72" mutants (e.g. see International patent application WO 98/18928), as these result in an enhanced immune response.

Microparticles are also useful and are preferably derived from a poly(a-hydroxy acid), in particular, from a poly(lactide) ("PLA"), a copolymer of D,L-lactide and glycolide or glycolic acid, such as a poly(D,L-lactide-co-glycolide) ("PLG" or "PLGA"), or a copolymer of D,L-lactide and caprolactone. The microparticles may be derived from any of various polymeric starting materials that have a variety of molecular weights and, in the case of the copolymers such as PLG, a variety of lactide:glycolide ratios, the selection of which will be largely a matter of choice. The prions, antibodies and/or polynucleotides of the invention may be entrapped within the microparticles, or may be adsorbed to them. Entrapment within PLG microparticles is preferred. PLG microparticles are discussed in further detail in Morris et al., (1994), Vaccine, 12:5-11, in chapter 13 of Mucosal Vaccines, eds. Kiyono et al., Academic Press 1996 (ISBN 012410587), and in chapters 16 & 18 of *Vaccine design: the subunit and adjuvant approach*, eds. Powell & Newman, Plenum Press 1995 (ISBN 0-306-44867-X).

LT mutants may advantageously be used in combination with microparticle-entrapped antigen, resulting in significantly enhanced immune responses.

Aluminum compounds and MF59 are preferred adjuvants for parenteral use.

Typically, the compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above.

Pharmaceutically acceptable salts can also be used in compositions of the invention, for example, mineral salts such as hydrochlorides, hydrobromides, phosphates, or sulfates, as well as salts of organic acids such as acetates, proprionates, malonates, or benzoates. Especially useful protein substrates are serum albumins, keyhole limpet hemocyanin, immunoglobulin molecules, thyroglobulin, ovalbumin, tetanus toxoid, and other proteins well known to those of skill in the art.

Compositions of the invention can also contain liquids or excipients, such as water, saline, glycerol, dextrose, ethanol, or the like, singly or in combination, as well as substances such as wetting agents, emulsifying agents, or pH buffering agents. A carrier is optionally present which is a molecule that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Furthermore, one or more polypeptides in the composition may be conjugated to a bacterial toxoid, such as toxoid from diphtheria, tetanus, cholera, etc.

D. Delivery

The compositions of the invention may be administered in a single dose, or as part of an administration regime. Nucleic acids and/or peptides may be administered may be administered by any suitable modality including, but not limited to intramuscularly, intramucosally, subcutaneously, intradermally, transdermally, intravaginally, intrarectally, orally and/or intravenously. The dosage regime may include priming and boosting doses, which may be administered mucosally, parenterally, or various combinations thereof.

In certain embodiments, one or more components of the compositions are administered parenterally or mucosally. Suitable routes of parenteral administration include intramuscular (IM), subcutaneous, intravenous, intraperitoneal, intradermal, transcutaneous, and transdermal (see e.g., International patent application WO 98/20734) routes, as well as delivery to the interstitial space of a tissue. Suitable routes of mucosal administration include oral, intranasal, intragastric, pulmonary, intestinal, rectal, ocular and vaginal routes. The composition may be adapted for mucosal administration. For instance, where the composition is for oral administration, it may be in the form of tablets or capsules, optionally enteric-coated, liquid, transgenic plants, etc. Where the composition is for intranasal administration, it may be in the form of a nasal spray, nasal drops, gel or powder. Dosage treatment may be a single dose schedule or a multiple dose schedule.

The compositions (or components thereof) may also be encapsulated, adsorbed to, or associated with, particulate carriers. Such carriers present multiple copies of a selected antigen to the immune system and promote trapping and retention of antigens in local lymph nodes. The particles can be phagocytosed by macrophages and can enhance antigen presentation through cytokine release. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* (1993) 10:362-368; McGee J P, et al., *J Microencapsul.* 14(2):197-210, 1997; O'Hagan D T, et al., *Vaccine* 11(2):149-54, 1993. Suitable microparticles may also be manufactured in the presence of charged detergents, such as anionic or cationic detergents, to yield microparticles with a surface having a net negative or a net positive charge. For example, microparticles manufactured with anionic detergents, such as hexadecyltrimethylammonium bromide (CTAB), i.e. CTAB-PLG microparticles, adsorb negatively charged macromolecules, such as DNA. (see, e.g., Int'l Application Number PCT/US99/17308).

Furthermore, other particulate systems and polymers can be used for the in vivo or ex vivo delivery. For example, polymers such as polylysine, polyarginine, polyornithine, spermine, spermidine, as well as conjugates of these molecules, are useful for transferring a nucleic acid of interest. Similarly, DEAE dextran-mediated transfection, calcium phosphate precipitation or precipitation using other insoluble inorganic salts, such as strontium phosphate, aluminum silicates including bentonite and kaolin, chromic oxide, magnesium silicate, talc, and the like, will find use with the present methods. See, e.g., Felgner, P. L., *Advanced Drug Delivery Reviews* (1990) 5:163-187, for a review of delivery systems useful for gene transfer. Peptoids (Zuckerman, R. N., et al., U.S. Pat. No. 5,831,005, issued Nov. 3, 1998, herein incorporated by reference) may also be used for delivery of a construct of the present invention.

As noted above, peptides (or antibodies) can also be delivered a nucleic acids encoding these molecules. The desired sequence is inserted into a uni-cistronic or multi-cistronic vector containing selected control elements (e.g., promoters, enhancers, etc.). Once complete, the constructs can be delivered using standard gene delivery protocols including, for example, injection using either a conventional syringe (e.g., U.S. Pat. Nos. 5,399,346, 5,580,859, 5,589,466) or a gene gun, such as the Accell® gene delivery system (PowderJect Technologies, Inc., Oxford, England); using viral based systems such as retroviral systems as described in (U.S. Pat. No. 5,219,740), adenoviral systems (Barr et al., *Gene Therapy* (1994) 1:51-58; Berkner, K. L. *BioTechniques* (1988) 6:616-629; and Rich et al., *Human Gene Therapy* (1993) 4:461-476), adeno-associated virus (AAV) systems (U.S. Pat. Nos. 5,173,414 and 5,139,941), pox viral systems, vaccinia viral delivery systems (see, e.g., International Publication No. WO 94/26911), avipoxyiral systems, such as the fowlpox and canarypox viruses, alphaviral delivery systems (U.S. Pat. Nos. 5,843,723; 5,789,245; 6,342,372; 6,329,201) as well as other viral systems; non-viral systems such as charged or uncharged liposomes (see, e.g,. Hug and Sleight, *Biochim. Biophys. Acta.* (1991) 1097:1-17; Straubinger et al., in *Methods of Enzymology* (1983), Vol. 101, pp. 512-527; Felgner et al., *Proc. Natl. Acad. Sci. USA* (1987) 84:7413-7416)); and/or cochleate lipid compositions similar to those described by Papahadjopoulos et al., *Biochem. Biophys. Acta.* (1975) 394:483-491. See, also, U.S. Pat. Nos. 4,663,161 and 4,871,488.

Polynucleotides can be delivered either directly to the vertebrate subject or, alternatively, delivered ex vivo, to cells derived from the subject and the cells reimplanted in the subject.

The methods of the invention further comprise treating or preventing a prion-relating disease by administering to an animal a composition comprising an effective amount of the antibodies of the invention.

Methods of treatment may combine any of the compositions described herein, for example peptide-containing compositions and/or antibody compositions. The various components may be administered together or separately.

Animals suitable for use in the methods of the invention include humans and other primates, including non-human primates such as chimpanzees, and other apes and monkey species; farm animals such as cattle, sheep, pigs, goats and horses, domestic animals such as dogs and cats; laboratory animals including rodents such as mice, rats, hamsters and guinea pigs; birds, including domestic, wild and game birds such as chickens, turkeys and other gallinaceous birds, ducks, geese and the like. Animals suitable for use in the invention can be of any age, including both adult and newborn. Transgenic animals can also be used in the invention. See generally, Prusiner "Prions" *Proc. Natl. Acad. Sci. USA* (1998) 95:13363-13383 for a discussion of transgenic animals currently used to study prion-related diseases.

The compositions of the invention can be used to treat or prevent prion-related diseases. Such prion-related diseases include a disease cause in whole or in part by a pathogenic prion protein ($PrP^{Sc}$). Prion-related diseases include scrapie, bovine spongiform encephalopathies (BSE), mad cow disease, feline spongiform encephalopathies, kuru, Creutzfeldt-Jakob Disease (CJD), Gerstmann-Strassier-Scheinker Disease (GSS), and fatal familial insomnia (FFI).

EXAMPLES

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Peptide Reagent Production

Peptide fragments of prion proteins were chemically synthesized using standard peptide synthesis techniques, essentially as described in Merrifield (1969) Advan. Enzymol. 32: 221 and Holm and Medal (1989), Multiple column peptide synthesis, p. 208E, Bayer and G. Jung (ed.), Peptides 1988, Walter de Gruyter & Co. Berlin-N.Y. Peptides were purified by HPLC and sequence verified by mass spectroscopy.

In certain cases, the peptides synthesized included additional residues at the N or C terminus, for example GGG residues and/or included one or more amino acid substitutions as compared to wild-type sequences.

A. Peptoid Substitutions

Peptoid substitutions were also made in the peptide presented in SEQ ID NO:14 (QWNKPSKPKTN, corresponding to residues 97 to 107 of SEQ ID NO:2), SEQ ID NO:67 (KKRPKPGGWNTGG, corresponding to residues 23-36 of SEQ ID NO:2) and SEQ ID NO:68 (KKRPKPGG, corresponding to residues 23-30 of SEQ ID NO:2). In particular, one or more proline residues of these peptides were substituted with various N-substituted peptoids. See, FIG. 3 for peptoids that can be substituted for any proline. Peptoids were prepared and synthesized as described in U.S. Pat. Nos. 5,877,278 and 6,033,631, both of which are incorporated by reference in their entireties herein; Simon et al. (1992) *Proc. Natl. Acad. Sci. USA* 89:9367.

B. Multimerization

Certain peptide reagents were also prepared as multimers, for example by preparing tandem repeats (linking multiple copies of a peptide via linkers such as GGG), multiple antigenic peptides (MAPS) and/or linearly-linked peptides.

In particular, MAPS were prepared using standard techniques, essentially as described in Wu et al. (2001) *J Am Chem Soc.* 2001 123(28):6778-84; Spetzler et al. (1995) *Int J Pept Protein Res.* 45(1):78-85.

Figure 5:
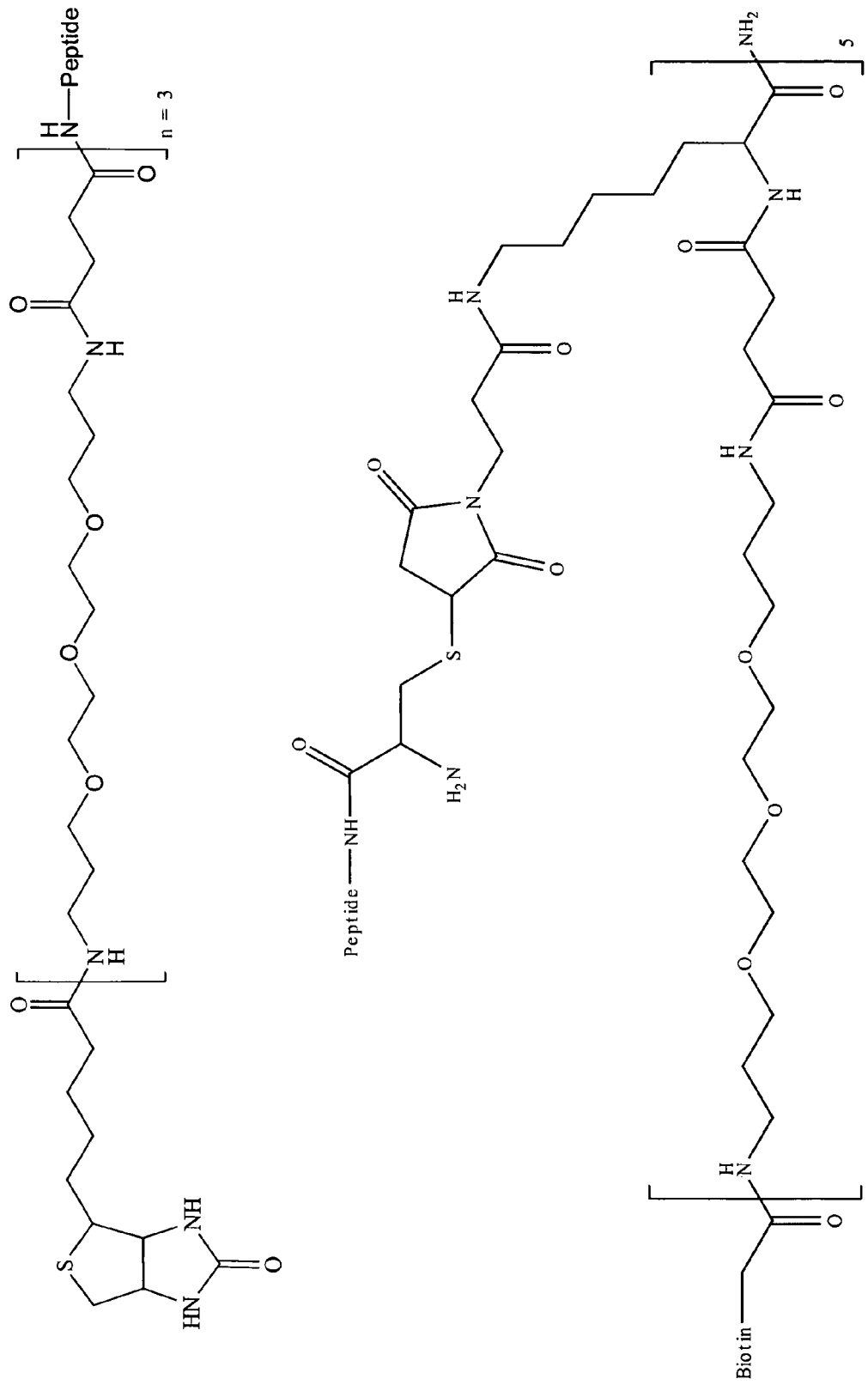
FIG. 5 depicts the structures of exemplary PEG-linked peptide reagents as described herein.

Linear and branched peptides (e.g., PEG linker multimerization) were also prepared using polyethylene glycol (PEG) linkers, using standard techniques. In particular, branched multipeptide PEG scaffolds were created with the following structures: Biotin-PEG-Lys-PEG-Lys-PEG-Lys-PEG-Lys-PEG-Lys (no peptide control) and Biotin-PEG-Lys(Peptide)-PEG-Lys(Peptide)-PEG-Lys(Peptide)-PEG-Lys(Peptide)-PEG-Lys(Peptide). In addition, peptide to Lys linkages were prepared: Lys-epsilon-NH—CO—(CH2)$_3$-Mal-S-Cys-peptide. See, FIG. 5.

C. Biotinylation

Peptides were biotinylated using standard techniques following synthesis and purification. Biotin was added to the N- or C-terminal of the peptide.

Example 2

Binding Assays

A. Pull-Down

Peptide reagents as described herein were tested for their ability to specifically bind to prion proteins using a magnetic bead pull down assay. For this assay, the peptide reagents were labeled with biotin, which allowed attachment to streptavidin coated magnetic beads.

Brain homogenates are prepared from RML PrP$^{Sc+}$ and PrP$^{C+}$ Balb-c mice. In brief, 5 mL of TBS buffer (50 mM Tris-HCl pH 7.5 and 37.5 mM NaCl) with 1% TW20 and 1% triton 100 was added to brains weighing ~0.5 g to produce a 10% homogenate. The brain slurry was dounced until large particles had disappeared. Aliquots of 200 µl were diluted 1:1 in buffer were added to pre-cooled eppendorf tubes and the samples sonicated for several repeats of several seconds each. Samples were centrifuged for 10-15 minutes at 500× and the supernatants removed.

To test the effect of Proteinase K digestion, certain supernatants were divided into two samples and 4 µl of Proteinase K was added to one sample and rotated at 37° C. for 1 hour. Eight microliters of PMSF was added to the proteinase K tubes to stop digestion and the tubes were incubated for a minimum of 1 hour at 4° C.

Homogenates were stored at 4° C. degrees until further use and sonicated again as described above if needed. A 10% w/v PrP$^{C+}$ or PrP$^{Sc+}$ preparation of the brain homogenates was incubated overnight at 4° C. with a biotin-labeled peptide reagent, as follows Tubes containing 400 µl of buffer, 50 µl of extract and 5 µl of biotin-labeled peptide reagent (10 mM stock) were prepared. The tubes were incubated for a minimum of 2 hours at room temperature or overnight at 4° C. on platform rocker.

Following incubation, 50 µl of SA-beads (Dynal M280 Streptavidin 112.06) were added and the tubes mixed by vortexing. The tubes were incubated, with rocking (VWR, Rocking platform, Model 100), for 1 hour at room temperature or overnight in at 4° C.

Samples were removed from shaker, placed in magnetic field to collect the magnetic beads with attached peptide reagent and prion and washed 5-6 time using 1 ml assay buffer. Samples were used immediately or stored at −20° C. until Western blotting or ELISA, described below.

B. Western blotting

Western blotting analysis was performed as follows. Bead-peptide-prion complexes precipitated as described above were denatured after the final wash by adding 25-30 µl of SDS buffer (Novex Tris-Glycine SDS-Sample Buffer 2×) added to each tube. The tubes were mixed by vortexing until all of the beads were suspended. The tubes were boiled until the tops started to come open, run on a standard SDS-PAGE gel and transferred to a solid membrane for WB analysis.

The membrane was blocked for 30 minutes in 5% Milk/TBS-T [50 ml 1 M Tris pH 7.5; 37.5 ml 4M NaCl, 1-10 mL Tween bring volume to 1 L with milk] at room temperature. Between 10-15 ml of anti-prion polyclonal antibodies, as described in International Application No. PCT/US03/31057, filed Sep. 30, 2003, entitled "Prion Chimeras and Uses Thereof" were added at a 1:50 fold dilution to the membrane and incubated for 1 hour at room temperature. The membrane was washed multiple times in TBS-T. After washing, the secondary antibody (goat anti-rabbit IgG (H+L) antibody (Pierce) conjugated to alkaline phosphatase (AP) was added at 1:1000 dilution (in TBS-T) and incubated for 20 minutes at room temperature. The membrane was washed multiple times in TBS-T. Alkaline phosphatase precipitating reagent (1-step NBT/BCIP (Pierce) was added and developed until background appeared or signal was apparent.

C. ELISA

Following the final wash, the bead-peptide complexes described above were denatured with Guanidine thiocyanate and ELISAs performed on the denatured protein as previously described in Ryou et al. (2003) *Lab Invest.* 83(6):837-43. O.D. values over blank controls (ranging from 0.172-0.259) were considered positive.

D. Results

Results of Western blotting and ELISA binding assays are summarized in Table 2. In brief, proteinase K digestion of brain homogenates was not necessary in order to detect specific binding of the peptide reagents as described herein to bind to PrP$^{Sc}$. As shown in FIG. 4, in no case was binding observed to wild type brain homogenates, indicating that the peptide reagents were binding to PrP$^{Sc}$ specifically. Furthermore, Western blotting analysis described above detected PrP$^{Sc}$ at over four logs dilution while ELISA was at least 10×more sensitive than Western blotting.

TABLE 2

| Peptide reagent (biotin labeled on N- or C-terminal) | Seq Id: | Western Blot[1] | ELISA $A_{405nm}$ |
|---|---|---|---|
| $^3$CGG$^5$WGQGGGTHNQWNKPSKPKTNLKHV$^3$C | 35 | + | 0.687 |
| $^3$GGWGQGGGTHNQWNKPSKPKTNLKV | 36 | + | ND |

TABLE 2-continued

| Peptide reagent (biotin labeled on N- or C-terminal) | Seq Id: | Western Blot[1] | ELISA A[405nm] |
|---|---|---|---|
| GGWGQGGGTHNQWNKPSKPKTNLKHV[3] | 37 | + | ND |
| C[5]GGWGQGGGTHNQWNKPSKPKTNLKHV[3]C | 40 | + | ND |
| RPMIHFGNDWEDRYYRENMYR[4] | 44 | − | ND |
| [4]RPMIHFGNDWEDRYYRENMYR[5]C | 76 | − | ND |
| [5]C[4]RPMIHFGNDWEDRYYRENMYR[4]C[2] | 46 | + | ND |
| QWNKPSKPKTN[4] | 50 | + | 0.932 |
| QWNKPSKPKTN | 14 | +++ | 0.775 |
| QWNKPSKPKTN[4]QWNKPSKPKTN | 51 | +++ | .923 |
| QWNKPSKPKTNLKHV[4] | 77 | ++ | 0.839 |
| GGWGQGGGTHNQWNKPSKPKTN | 53 | + | 0.254 |
| GGTHNQWNKPSKPKTN | 54 | + | 0.253 |
| [4]AGAAAAGAVVGGLGGYMLGSAM | 78 | insoluble | 0.259 |
| [4]AGAAAAGAVVGGLGG | 56 | insoluble | 0.313 |
| [6]AGAAAAGAVVGGLGGYMLGSAM | 57 | + | 0.901 |
| [6]AGAAAAGAVVGGLGG | 65 | ++ | 0.635 |
| [4]KKRPKPGGWNTGGSRYPGQGS | 66 | + | 0.533 |
| [4]KKRPKPGGWNTGG | 67 | ++ | 0.451 |
| [4]KKRPKPGG | 68 | +++ | 0.765 |
| PHGGGWGQPHGGSWGQPHGGSWGQ | 69 | − | 0.282 |
| PHGGGWGQPHGGSWGQ | 70 | − | 0.241 |
| PHGGGWGQ | 71 | − | 0.263 |
| [4]GPKRKGPK | 73 | + | 1.0621 |
| [4]WNKPSKPKT | 75 | − | 0.247 |
| [4]NKPSKPK | 79 | − | 0.24 |
| [4]KPSKPK | 80 | − | 0.225 |
| [4]KKRPKPGGGKKRPKPGG | 72 | + | 0.522 |
| [4]KKRPKPGGGQWNKPSKPKTN | 81 | + | 1.247 |
| KKKAGAAAAGAVVGGLGGYMLGSAMDDD | 82 | − | 0.340 |
| DDDAGAAAAGAVVGGLGGYMLGSAM | 83 | − | 0.237 |
| KKKAGAAAAGAVVGGLGGYMLGSAMKKK | 84 | + | 0.268 |
| [4]KKKKKKKK | 85 | +[3] | 0.530 |
| DDDAGAAAAGAVVGGLGGYMLGSAMDDD | 86 | − | 0.227 |
| [4]NNKQSPWPTKK | 87 | − | 0.277 |
| DKDKGGVGALAGAAVAAGGDKDK | 88 | − | 0.282 |
| [4]QANKPSKPKTN | 89 | + | 0.245 |
| [4]QWNKASKPKTN | 90 | − | 0.283 |
| [4]QWNKPSKAKTN | 91 | − | 0.256 |
| [4]QWNAPSKPKTN | 92 | − | 0.230 |
| [4]QWNKPSAPKTN | 93 | − | 0.250 |
| [4]QWNKPSKPATN | 94 | − | 0.260 |
| [4]QWNKASKAKTN | 95 | − | 0.241 |
| [4]KKRAKPGG | 96 | + | 2.19 |
| [4]KKRPKAGG | 97 | + | 1.24 |
| [4]KKRAKAGG | 98 | + | 1.46 |

[1]Visually evaluated relative signal intensity
[2]cyclized
[3]GGGG residues added/inserted at indicated position
[4]GGG residues added/inserted at indicated position
[5]GG residues added/inserted at indicated position
[6]KKK residues added/inserted at indicated position
ND = not determined Alanine scanning was also performed to identify residues involved in binding. Results are shown in Table 3.

TABLE 3

| Peptide reagent (biotin label on N- or C-terminus) | SEQ ID NO | Western Blot | ELISA A[405nm] |
|---|---|---|---|
| QWNKPSKPKTN | 14 | +++ | 0.775 |
| QANKPSKPKTN | 89 | +++ | 0.245 |
| QWNAPSKPKTN | 92 | + | 0.283 |
| QWNKPSAPKTN | 93 | + | 0.256 |
| QWNKPSKPATN | 94 | + | 0.230 |
| QWNKASKPKTN | 99 | +/− | 0.250 |
| QWNKPSKAKTN | 91 | + | 0.260 |
| QWNKASKAKTN | 95 | − | 0.241 |
| QWAKPSKPKTN | 100 | ND | 0.376 |
| QWNKPAKPKTN | 101 | ND | 0.356 |
| QWNKPSKPKAN | 102 | ND | 0.234 |
| QWNKPSKPKTA | 103 | ND | 0.262 |
| KKRPKPGG | 68 | +++ | 0.765 |
| AKRPKPGG | 104 | + | 0.273 |
| KARPKPGG | 105 | + | 0.256 |
| KKAPKPGG | 106 | + | 0.268 |
| KKRPAPGG | 107 | + | 0.578 |
| KKRAKPGG | 96 | ++ | 2.19 |
| KKRPKAGG | 97 | ++ | 1.24 |
| KKAPKAGG | 108 | + | 1.46 |

In addition, as shown in Table 4, binding to PrP$^{Sc}$ by the peptide reagents having SEQ ID NO:14, SEQ ID NO: 67 and SEQ ID NO:68 was further enhanced by substitutions at the proline residues by a number of N-substituted glycines (peptoids).

TABLE 4

| | Western Blot | ELISA $A_{405\ nm}$ |
|---|---|---|
| * in (GGG)[1]QWNKPSK*KTN (SEQ ID NO: 14) | | |
| Proline | +++ | 0.775 |
| N-(S)-(1-phenylethyl)glycine (peptoid as circled in FIG. 3A) (SEQ ID NO: 109) | ++ | 0.865 |
| N-(4-hydroxyphenyl)glycine (peptoid as circled in FIG. 3B) (SEQ ID NO: 110) | − | 0.934 |
| N-(cyclopropylmethyl)glycine (peptoid as circled in FIG. 3C) (SEQ ID NO: 111) | +++++ | 1.141 |
| N-(isopropyl)glycine (peptoid as circled in FIG. 3D) (SEQ ID NO: 112) | ND | 0.974 |
| N-(3,5-dimethoxybenzyl)glycine (peptoid as circled in FIG. 3E) (SEQ ID NO: 113) | +++ | 2.045 |
| N-butylglycine (peptoid as circled in FIG. 3F) (SEQ ID NO: 114) | ++++ | 0.776 |
| * in (GGG)[1]QWNK*SKPKTN (SEQ ID NO: 14) | | |
| N-(cyclopropylmethyl)glycine (SEQ ID NO: 115) | ND | 0.498 |
| N-(isopropyl)glycine (SEQ ID NO: 116) | ND | 1.57 |
| N-(3,5-dimethoxybenzyl)glycine (SEQ ID NO: 117) | ND | 0.823 |
| N-butylglycine (SEQ ID NO: 118) | ND | 0.619 |
| * in (GGG)[1]KKRPK*GG (SEQ ID NO: 68) | | |
| proline | ND | 0.765 |
| N-butylglycine (SEQ ID NO: 119) | ND | 0.61 |
| N-(3,5-dimethoxybenzyl)glycine (SEQ ID NO: 120) | ND | 0.631 |
| N-(isopropyl)glycine (SEQ ID NO: 121) | ND | 0.509 |
| N-(cyclopropylmethyl)glycine (SEQ ID NO: 122) | ND | 0.503 |
| * in (GGG)[1]KKRPK*GGWNTGG (SEQ ID NO: 67) | | |
| Proline | ND | 0.451 |
| N-butylglycine (SEQ ID NO: 123) | ND | 0.503 |
| N-(3,5-dimethoxybenzyl)glycine (SEQ ID NO: 124) | ND | 0.464 |
| N-(isopropyl)glycine (SEQ ID NO: 125) | ND | 0.555 |
| N-(cyclopropylmethyl)glycine (SEQ ID NO: 126) | ND | 0.344 |
| (GGG)[1]QWNKX1SKX2KTN | | |
| N-(cyclopropylmethyl)glycine at X1; N-(cyclopropylmethyl)glycine at X2 (SEQ ID NO: 129) | ND | ND |
| N-(cyclopropylmethyl)glycine at X1; N-(3,5-dimethoxybenzyl)glycine at X2 (SEQ ID NO: 130) | ND | ND |
| N-(cyclopropylmethyl)glycine at X1; N-butylglycine at X2 (SEQ ID NO: 131) | ND | ND |
| N-(isopropyl)glycine at X1; N-(cyclopropylmethyl)glycine at X2 (SEQ ID NO: 132) | ND | ND |

[1] The optional GGG linker was not present in the peptide reagents in the experiments shown in this table.

Furthermore, multimerization of PrP$^{Sc}$-binding peptide reagents also improved affinity for PrP$^{Sc}$. In particular, tandem repeats gave stronger signals (as measured by Western blotting) than single copies. Pre-derivatized MAP forms on beads increased binding in certain cases up to 2-fold. However, MAP forms caused precipitation of the peptide in solution. Linearly-linked peptides were also tested for their ability to enhance binding without causing precipitation.

Example 3

Antibody Production

The following provides an example of a protocol that can be used to generate antibodies to the peptide reagents of the invention.

Mice are immunized with a composition comprising a peptide reagent as described herein (e.g., any one of SEQ ID NOs:12-108, preferably any one of SEQ ID NOs:14, 35, 50, 51, 56, 57, 65, 66, 67, 68, 72, 73, 77, 81, 82) either IM (intramuscular) or IP (intraperitoneal) on day 0, followed by 2-5 boosts at intervals of not more frequently than every 2 weeks. Blood is collected before the first immunization and then 7 days following each boost to monitor the humoral response to the antigen. 6 orbital eye bleeds are taken from each animal (three from each eye) of approximately 0.2 mls or less per bleed. The final boost is delivered by IV (intravenous) injection. Three days after the final boost, mice are euthanized by exposure to $CO_2$ or isofluorane followed by cervical dislocation. Spleens are then harvested for hybridoma production.

Freund's adjuvant, complete, is used as an adjuvant for the first injection followed by Incomplete Freund's adjuvant for the remaining infections, except for the IV infection. The IV injections are prepared in saline.

Although preferred embodiments of the subject invention have been described in some detail, it is understood that obvious variations can be made without departing from the spirit and the scope of the invention as defined herein.

What is claimed is:

1. An isolated peptide reagent that interacts preferentially with pathogenic forms of a conformational disease protein as compared to nonpathogenic forms of the conformational disease protein, wherein the peptide reagent comprises SEQ ID NO:68 and further wherein the peptide reagent (i) is a fragment of a prion protein; or (ii) comprises no more than 100 amino acid residues in length.

2. The peptide reagent of claim 1, wherein the conformational disease is a prion-related disease, the pathogenic protein is PrP$^{Sc}$, and the nonpathogenic form is PrP$^{C}$.

3. The peptide reagent of claim 1, wherein said peptide reagent is genetically encoded.

4. The peptide reagent of claim 1, wherein the peptide reagent includes the amino acid sequence (G)n, where n=1, 2, 3 or 4, at the N-terminal end and/or at the C-terminal.

5. The peptide reagent of claim 1, wherein the peptide reagent is biotinylated.

6. A complex comprising the peptide reagent of claim 2 and a pathogenic prion protein.

7. A method for detecting the presence of a pathogenic prion in a sample comprising: (a) contacting a sample suspected of containing a pathogenic prion with a first peptide reagent according to claim 2 under conditions that allow the binding of the first peptide reagent to the pathogenic prion protein, if present, to form a first complex; and (b) detecting the presence the pathogenic prion, if any, in the sample by its binding to the first peptide reagent.

8. The method of claim 7, wherein said first peptide reagent is detectably labeled.

9. The method of claim 7, wherein said first peptide reagent is biotinylated.

10. The method of claim 7, wherein said first peptide reagent is attached to a solid support.

11. A method for detecting the presence of a pathogenic prion in a sample comprising: (a) contacting a sample suspected of containing a pathogenic prion with a first peptide reagent according to claim 2, under conditions that allow the binding of the first peptide reagent to the pathogenic prion, if present, to form a first complex; (b) contacting said first complex with a second peptide reagent according to claim 2 under conditions that allow the binding of the second peptide reagent to the pathogenic prion in said first complex, wherein said second peptide reagent comprises a detectable label; and (c) detecting the presence the pathogenic prion, if any, in the sample by its binding to the second peptide reagent.

12. The method of claim 11, wherein said first peptide reagent and said second peptide reagent are different.

13. The method of claim 11, wherein said first peptide reagent and said second peptide reagent are the same.

14. The method of claim 11, wherein said first peptide reagent is attached to a solid support.

15. The method of claim 11, wherein said first peptide reagent is biotinylated.

16. A method for detecting the presence of a pathogenic prion in a sample comprising: (a) contacting a sample suspected of containing a pathogenic prion with a first peptide reagent according to claim 2 under conditions that allow the binding of the first peptide reagent to the pathogenic prion, if present, to form a first complex; (b) removing unbound sample materials; (c) dissociating said pathogenic prion from said first complex; (d) contacting said dissociated pathogenic prion with a second peptide reagent according to claim 2 under conditions that allow the binding of the second peptide reagent to the pathogenic prion, wherein said second peptide reagent comprises a detectable label; and (e) detecting the presence the pathogenic prion, if any, in the sample by its binding to the second peptide reagent.

17. A method for detecting the presence of a pathogenic prion in a sample comprising: (a) contacting a sample suspected of containing a pathogenic prion with a first peptide reagent according to any of claim 2 under conditions that allow the binding of the first peptide reagent to the pathogenic prion, if present, to form a first complex; (b) removing unbound sample materials; (c) dissociating said pathogenic prion from said first complex; (d) contacting said dissociated pathogenic prion with a prion-binding reagent under conditions that allow the binding of the prion-binding reagent to the pathogenic prion, wherein said prion-binding reagent comprises a detectable label; and (e) detecting the presence the pathogenic prion, if any, in the sample by its binding to the prion-binding reagent.

18. The method of claim 17, wherein said prion-binding reagent is selected from the group consisting of anti-prion antibodies, motif-grafted hybrid polypeptides, cationic or anionic polymers, propagation catalysts and plasminogen.

19. A method for detecting the presence of a pathogenic prion in a sample comprising: (a) contacting a sample suspected of containing a pathogenic prion with a prion-binding reagent under conditions that allow the binding of the prion-binding reagent to the pathogenic prion, if present, to form a first complex; (b) removing unbound sample materials; (c) contacting said first complex with a peptide reagent according to claim 2 under conditions that allow the binding of the peptide reagent to the pathogenic prion, wherein said peptide reagent comprises a detectable label; and (d) detecting the presence the pathogenic prion, if any, in the sample by its binding to the peptide reagent.

20. A method for detecting a pathogenic prion in a sample, comprising: (a) providing a solid support comprising first peptide reagent according to claims 2; (b) contacting the solid support with a sample under conditions which allow pathogenic prions, when present in the sample, to bind to the first peptide reagent; contacting the solid support with a detectably labeled second peptide reagent according to claim 2 under conditions which allow the second peptide reagent to bind to pathogenic prions bound by the first peptide reagent; and, (c) detecting complexes formed between the first peptide reagent, a pathogenic prion from the sample and the second peptide reagent, thereby detecting the presence of the pathogenic prion in the sample.

21. A method for detecting the presence of a pathogenic prion in a sample comprising: (a) providing a solid support comprising a prion-binding reagent; (b) contacting the solid support to a sample under conditions which allow prion proteins, when present in the sample, to bind to the prion-binding reagent; (c) contacting the solid support to a detectably labeled second peptide reagent according to claim 2; and (d) detecting complexes formed between the prion-binding reagent, a pathogenic prion from the biological sample, and the second peptide reagent.

22. A method for detecting the presence of a pathogenic prion in a sample comprising: (a) providing a solid support comprising a first peptide reagent according to claim 2; (b) combining the solid support with a detectably labeled first ligand, wherein the first peptide reagent's binding affinity to the detectably labeled first ligand is weaker than the first peptide reagent's binding affinity to a pathogenic prion; (c) combining a sample with the solid support under conditions which allow a pathogenic prion, when present in the sample, to bind to the first peptide reagent and replace the first ligand; (d) detecting complexes formed between the first peptide reagent and the pathogenic prion from the sample.

23. The method of claim 10, wherein the solid support is selected from the group consisting of nitrocellulose, polystyrene latex, polyvinyl fluoride, diazotized paper, nylon membranes, activated beads, and magnetically responsive beads.

24. The method of claim 7, wherein the sample is a biological sample.

25. The method of claim 24, wherein the biological sample is selected from the group consisting of organs, whole blood, blood fractions, blood components, plasma, platelets, serum, cerebrospinal fluid (CSF), brain tissue, nervous system tissue, muscle tissue, bone marrow, urine, tears, non-nervous system tissue, organs, and/or biopsies or necropsies.

26. The method of claim 25, wherein the biological sample is whole blood, plasma, platelets, blood fractions, or serum.

27. A solid support comprising at least one peptide reagent according to claim 2.

28. A kit for detecting the presence of a pathogenic prion in a sample comprising: (a) a solid support according to claim 27; and other necessary reagents and, optionally, positive and negative controls.

29. A composition comprising a peptide reagent according to claim 2.

30. A method for isolating a pathogenic prion protein from a sample comprising: (a) providing a solid support comprising a peptide reagent according to claim 2; (b) contacting said sample with said solid support under conditions that allow the binding of a pathogenic prion protein, if present in said sample, to said first peptide reagent, to form a first complex and (c) removing unbound sample materials.

31. The method of claim 30, further comprising the step of dissociating said pathogenic prion protein from said first complex.

32. A method of preparing blood supply that is substantially free of pathogenic prions, said blood supply comprising whole blood, plasma, platelets or serum, said method comprising: (a) screening aliquots of whole blood, plasma, platelets or serum from collected blood samples, by the method claim 7; (b) eliminating samples in which pathogenic prions are detected; and (c) combining samples in which pathogenic prions are not detected to provide a blood supply that is substantially free of pathogenic prions.

* * * * *

SEQUENCE LISTING

```
<160> NUMBER OF SEQ ID NOS: 132

<210> SEQ ID NO 1
<211> LENGTH: 253
<212> TYPE: PRT
<213> ORGANISM: Artificial
<220> FEATURE:
<223> OTHER INFORMATION: Full length human prion protein

<400> SEQUENCE: 1

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
```

-continued

```
                35                  40                  45
Tyr Pro Pro Gln Gly Gly Gly Trp Gly Gln Pro His Gly Gly
         50                  55                  60
Trp Gly Gln Pro His Gly Gly Trp Gly Gln Pro His Gly Gly
 65                  70                  75                  80
Trp Gly Gln Pro His Gly Gly Trp Gly Gln Gly Gly Thr His
                 85                  90                  95
Ser Gln Trp Asn Lys Pro Ser Lys Pro Lys Thr Asn Met Lys His Met
                100                 105                 110
Ala Gly Ala Ala Ala Ala Gly Ala Val Val Gly Gly Leu Gly Gly Tyr
                115                 120                 125
Met Leu Gly Ser Ala Met Ser Arg Pro Ile Ile His Phe Gly Ser Asp
        130                 135                 140
Tyr Glu Asp Arg Tyr Tyr Arg Glu Asn Met His Arg Tyr Pro Asn Gln
145                 150                 155                 160
Val Tyr Tyr Arg Pro Met Asp Glu Tyr Ser Asn Gln Asn Asn Phe Val
                165                 170                 175
His Asp Cys Val Asn Ile Thr Ile Lys Gln His Thr Val Thr Thr Thr
                180                 185                 190
Thr Lys Gly Glu Asn Phe Thr Glu Thr Asp Val Lys Met Met Glu Arg
        195                 200                 205
Val Val Glu Gln Met Cys Ile Thr Gln Tyr Glu Arg Glu Ser Gln Ala
        210                 215                 220
Tyr Tyr Gln Arg Gly Ser Ser Met Val Leu Phe Ser Ser Pro Pro Val
225                 230                 235                 240
Ile Leu Leu Ile Ser Phe Leu Ile Phe Leu Ile Val Gly
                245                 250

<210> SEQ ID NO 2
<211> LENGTH: 254
<212> TYPE: PRT
<213> ORGANISM: Artificial
<220> FEATURE:
<223> OTHER INFORMATION: Full Length Mouse Prion Protein

<400> SEQUENCE: 2

Met Ala Asn Leu Gly Tyr Trp Leu Leu Ala Leu Phe Val Thr Met Trp
  1               5                  10                  15
Thr Asp Val Gly Leu Cys Lys Lys Arg Pro Lys Pro Gly Gly Trp Asn
                 20                  25                  30
Thr Gly Gly Ser Arg Tyr Pro Gly Gln Gly Ser Pro Gly Gly Asn Arg
             35                  40                  45
Tyr Pro Pro Gln Gly Gly Thr Trp Gly Gln Pro His Gly Gly Trp
         50                  55                  60
Gly Gln Pro His Gly Gly Ser Trp Gly Gln Pro His Gly Gly Ser Trp
 65                  70                  75                  80
Gly Gln Pro His Gly Gly Gly Trp Gly Gln Gly Gly Thr His Asn
                 85                  90                  95
Gln Trp Asn Lys Pro Ser Lys Pro Lys Thr Asn Leu Lys His Val Ala
                100                 105                 110
Gly Ala Ala Ala Ala Gly Ala Val Val Gly Gly Leu Gly Gly Tyr Met
            115                 120                 125
Leu Gly Ser Ala Met Ser Arg Pro Met Ile His Phe Gly Asn Asp Trp
        130                 135                 140
Glu Asp Arg Tyr Tyr Arg Glu Asn Met Tyr Arg Tyr Pro Asn Gln Val
```

```
                145                 150                 155                 160

Tyr Tyr Arg Pro Val Asp Gln Tyr Ser Asn Gln Asn Asn Phe Val His
                165                 170                 175

Asp Cys Val Asn Ile Thr Ile Lys Gln His Thr Val Thr Thr Thr Thr
                180                 185                 190

Lys Gly Glu Asn Phe Thr Glu Thr Asp Val Lys Met Met Glu Arg Val
                195                 200                 205

Val Glu Gln Met Cys Val Thr Gln Tyr Gln Lys Glu Ser Gln Ala Tyr
                210                 215                 220

Tyr Asp Gly Arg Arg Ser Ser Ser Thr Val Leu Phe Ser Ser Pro Pro
225                 230                 235                 240

Val Ile Leu Leu Ile Ser Phe Leu Ile Phe Leu Ile Val Gly
                245                 250

<210> SEQ ID NO 3
<211> LENGTH: 253
<212> TYPE: PRT
<213> ORGANISM: Artificial
<220> FEATURE:
<223> OTHER INFORMATION: human prion protein

<400> SEQUENCE: 3

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
                20                  25                  30

Thr Gly Gly Ser Arg Tyr Pro Gly Gln Gly Ser Pro Gly Gly Asn Arg
            35                  40                  45

Tyr Pro Pro Gln Gly Gly Gly Trp Gly Gln Pro His Gly Gly Gly
        50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
                85                  90                  95

Ser Gln Trp Asn Lys Pro Ser Lys Pro Lys Thr Asn Met Lys His Met
                100                 105                 110

Ala Gly Ala Ala Ala Ala Gly Ala Val Val Gly Gly Leu Gly Gly Tyr
            115                 120                 125

Met Leu Gly Ser Ala Met Ser Arg Pro Ile Ile His Phe Gly Ser Asp
        130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
                180                 185                 190

Thr Lys Gly Glu Asn Phe Thr Glu Thr Asp Val Lys Met Met Glu Arg
            195                 200                 205

Val Val Glu Gln Met Cys Ile Thr Gln Tyr Glu Arg Glu Ser Gln Ala
        210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250
```

```
<210> SEQ ID NO 4
<211> LENGTH: 254
<212> TYPE: PRT
<213> ORGANISM: Artificial
<220> FEATURE:
<223> OTHER INFORMATION: Hamster prion protein

<400> SEQUENCE: 4
```

Met Ala Asn Leu Ser Tyr Trp Leu Leu Ala Leu Phe Val Ala Met Trp
1               5                   10                  15

Thr Asp Val Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Thr Trp Gly Gln Pro His Gly Gly Gly
    50                  55                  60

Trp Gly Gln Pro His Gly Gly Trp Gly Gln Pro His Gly Gly Gly
65                  70                  75                  80

Trp Gly Gln Pro His Gly Gly Gly Trp Gly Gln Gly Gly Gly Thr His
                85                  90                  95

Asn Gln Trp Asn Lys Pro Ser Lys Pro Lys Thr Asn Met Lys His Met
            100                 105                 110

Ala Gly Ala Ala Ala Ala Gly Ala Val Val Gly Gly Leu Gly Gly Tyr
        115                 120                 125

Met Leu Gly Ser Ala Met Ser Arg Pro Met Met His Phe Gly Asn Asp
    130                 135                 140

Trp Glu Asp Arg Tyr Tyr Arg Glu Asn Met Asn Arg Tyr Pro Asn Gln
145                 150                 155                 160

Val Tyr Tyr Arg Pro Val Asp Gln Tyr Asn Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Ile Lys Ile Met Glu Arg
        195                 200                 205

Val Val Glu Gln Met Cys Thr Thr Gln Tyr Gln Lys Glu Ser Gln Ala
    210                 215                 220

Tyr Tyr Asp Gly Arg Arg Ser Ser Ala Val Leu Phe Ser Ser Pro Pro
225                 230                 235                 240

Val Ile Leu Leu Ile Ser Phe Leu Ile Phe Leu Met Val Gly
                245                 250

```
<210> SEQ ID NO 5
<211> LENGTH: 264
<212> TYPE: PRT
<213> ORGANISM: Artificial
<220> FEATURE:
<223> OTHER INFORMATION: Bovine prion protein
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (154)..(154)
<223> OTHER INFORMATION: Xaa can be any naturally occurring amino acid

<400> SEQUENCE: 5
```

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly

-continued

```
                    20                  25                  30
Gly Trp Asn Thr Gly Gly Ser Arg Tyr Pro Gly Gln Gly Xaa Pro Gly
                35                  40                  45
Gly Asn Arg Tyr Pro Pro Gln Gly Gly Gly Trp Gly Gln Pro His
 50                  55                  60
Gly Gly Gly Trp Gly Gln Pro His Gly Gly Trp Gly Gln Pro His
 65                  70                  75                  80
Gly Gly Gly Trp Gly Gln Pro His Gly Gly Trp Gly Gln Pro His
                85                  90                  95
Gly Gly Gly Gly Trp Gly Gln Gly Thr His Gly Gln Trp Asn Lys
                100                 105                 110
Pro Ser Lys Pro Lys Thr Asn Met Lys His Val Ala Gly Ala Ala Ala
                115                 120                 125
Ala Gly Ala Val Val Gly Gly Leu Gly Gly Tyr Met Leu Gly Ser Ala
 130                 135                 140
Met Ser Arg Pro Leu Ile His Phe Gly Xaa Asp Tyr Glu Asp Arg Tyr
 145                 150                 155                 160
Tyr Arg Glu Asn Met His Arg Tyr Pro Asn Gln Val Tyr Tyr Arg Pro
                165                 170                 175
Val Asp Gln Tyr Ser Asn Gln Asn Asn Phe Val His Asp Cys Val Asn
                180                 185                 190
Ile Thr Val Lys Glu His Thr Val Thr Thr Thr Lys Gly Glu Asn
                195                 200                 205
Phe Thr Glu Thr Asp Ile Lys Met Met Glu Arg Val Val Glu Gln Met
 210                 215                 220
Cys Ile Thr Gln Tyr Gln Arg Glu Ser Gln Ala Tyr Tyr Gln Arg Gly
 225                 230                 235                 240
Ala Ser Val Ile Leu Phe Ser Ser Pro Val Ile Leu Leu Ile Ser
                245                 250                 255
Phe Leu Ile Phe Leu Ile Val Gly
                260

<210> SEQ ID NO 6
<211> LENGTH: 256
<212> TYPE: PRT
<213> ORGANISM: Artificial
<220> FEATURE:
<223> OTHER INFORMATION: Sheep prion protein

<400> SEQUENCE: 6

Met Val Lys Ser His Ile Gly Ser Trp Ile Leu Val Leu Phe Val Ala
 1               5                   10                  15
Met Trp Ser Asp Val Gly Leu Cys Lys Lys Arg Pro Lys Pro Gly Gly
                20                  25                  30
Gly Trp Asn Thr Gly Gly Ser Arg Tyr Pro Gly Gln Gly Ser Pro Gly
                35                  40                  45
Gly Asn Arg Tyr Pro Pro Gln Gly Gly Gly Trp Gly Gln Pro His
 50                  55                  60
Gly Gly Gly Trp Gly Gln Pro His Gly Gly Trp Gly Gln Pro His
 65                  70                  75                  80
Gly Gly Gly Trp Gly Gln Pro His Gly Gly Gly Trp Gly Gln Gly
                85                  90                  95
Gly Ser His Ser Gln Trp Asn Lys Pro Ser Lys Pro Lys Thr Asn Met
                100                 105                 110
Lys His Val Ala Gly Ala Ala Ala Ala Gly Ala Val Val Gly Gly Leu
```

```
                    115                 120                 125
Gly Gly Tyr Met Leu Gly Ser Ala Met Ser Arg Pro Leu Ile His Phe
            130                 135                 140
Gly Asn Asp Tyr Glu Asp Arg Tyr Tyr Arg Glu Asn Met Tyr Arg Tyr
145                 150                 155                 160
Pro Asn Gln Val Tyr Tyr Arg Pro Val Asp Arg Tyr Ser Asn Gln Asn
                165                 170                 175
Asn Phe Val His Asp Cys Val Asn Ile Thr Val Lys Gln His Thr Val
            180                 185                 190
Thr Thr Thr Thr Lys Gly Glu Asn Phe Thr Glu Thr Asp Ile Lys Ile
            195                 200                 205
Met Glu Arg Val Val Glu Gln Met Cys Ile Thr Gln Tyr Gln Arg Glu
        210                 215                 220
Ser Gln Ala Tyr Tyr Gln Arg Gly Ala Ser Val Ile Leu Phe Ser Ser
225                 230                 235                 240
Pro Pro Val Ile Leu Leu Ile Ser Phe Leu Ile Phe Leu Ile Val Gly
                245                 250                 255

<210> SEQ ID NO 7
<211> LENGTH: 254
<212> TYPE: PRT
<213> ORGANISM: Artificial
<220> FEATURE:
<223> OTHER INFORMATION: Mouse prion protein

<400> SEQUENCE: 7

Met Ala Asn Leu Gly Tyr Trp Leu Leu Ala Leu Phe Val Thr Met Trp
1               5                   10                  15
Thr Asp Val Gly Leu Cys Lys Lys Arg Pro Lys Pro Gly Gly Trp Asn
            20                  25                  30
Thr Gly Gly Ser Arg Tyr Pro Gly Gln Gly Ser Pro Gly Gly Asn Arg
        35                  40                  45
Tyr Pro Pro Gln Gly Gly Thr Trp Gly Gln Pro His Gly Gly Gly Trp
50                  55                  60
Gly Gln Pro His Gly Gly Ser Trp Gly Gln Pro His Gly Gly Ser Trp
65                  70                  75                  80
Gly Gln Pro His Gly Gly Trp Gly Gln Gly Gly Gly Thr His Asn
                85                  90                  95
Gln Trp Asn Lys Pro Ser Lys Pro Lys Thr Asn Leu Lys His Val Ala
            100                 105                 110
Gly Ala Ala Ala Ala Gly Ala Val Val Gly Gly Leu Gly Gly Tyr Met
        115                 120                 125
Leu Gly Ser Ala Met Ser Arg Pro Met Ile His Phe Gly Asn Asp Trp
    130                 135                 140
Glu Asp Arg Tyr Tyr Arg Glu Asn Met Tyr Arg Tyr Pro Asn Gln Val
145                 150                 155                 160
Tyr Tyr Arg Pro Val Asp Gln Tyr Ser Asn Gln Asn Asn Phe Val His
                165                 170                 175
Asp Cys Val Asn Ile Thr Ile Lys Gln His Thr Val Thr Thr Thr Thr
            180                 185                 190
Lys Gly Glu Asn Phe Thr Glu Thr Asp Val Lys Met Met Glu Arg Val
        195                 200                 205
Val Glu Gln Met Cys Val Thr Gln Tyr Gln Lys Glu Ser Gln Ala Tyr
    210                 215                 220
Tyr Asp Gly Arg Arg Ser Ser Ser Thr Val Leu Phe Ser Ser Pro Pro
```

```
                225                 230                 235                 240
Val Ile Leu Leu Ile Ser Phe Leu Ile Phe Leu Ile Val Gly
                245                 250

<210> SEQ ID NO 8
<211> LENGTH: 256
<212> TYPE: PRT
<213> ORGANISM: Artificial
<220> FEATURE:
<223> OTHER INFORMATION: Elk prion protein

<400> SEQUENCE: 8

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Trp Gly Gln Pro His
    50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Trp Gly Gln Gly
                85                  90                  95

Gly Thr His Ser Gln Trp Asn Lys Pro Ser Lys Pro Lys Thr Asn Met
            100                 105                 110

Lys His Val Ala Gly Ala Ala Ala Ala Gly Ala Val Val Gly Gly Leu
        115                 120                 125

Gly Gly Tyr Met Leu Gly Ser Ala Met Ser Arg Pro Leu Ile His Phe
    130                 135                 140

Gly Asn Asp Tyr Glu Asp Arg Tyr Tyr Arg Glu Asn Met Tyr Arg Tyr
145                 150                 155                 160

Pro Asn Gln Val Tyr Tyr Arg Pro Val Asp Gln Tyr Asn Asn Gln Asn
                165                 170                 175

Thr Phe Val His Asp Cys Val Asn Ile Thr Val Lys Gln His Thr Val
            180                 185                 190

Thr Thr Thr Thr Lys Gly Glu Asn Phe Thr Glu Thr Asp Ile Lys Met
        195                 200                 205

Met Glu Arg Val Val Glu Gln Met Cys Ile Thr Gln Tyr Gln Arg Glu
    210                 215                 220

Ser Glu Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255

<210> SEQ ID NO 9
<211> LENGTH: 256
<212> TYPE: PRT
<213> ORGANISM: Artificial
<220> FEATURE:
<223> OTHER INFORMATION: Fallow prion protein

<400> SEQUENCE: 9

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30
```

```
Gly Trp Asn Thr Gly Gly Ser Arg Tyr Pro Gly Gln Gly Ser Pro Gly
         35                  40                  45

Gly Asn Arg Tyr Pro Pro Gln Gly Gly Gly Trp Gly Gln Pro His
 50                  55                  60

Gly Gly Gly Trp Gly Gln Pro His Gly Gly Trp Gly Gln Pro His
 65                  70                  75                  80

Gly Gly Gly Trp Gly Gln Pro His Gly Gly Gly Trp Gly Gln Gly
                     85                  90                  95

Gly Thr His Ser Gln Trp Asn Lys Pro Ser Lys Pro Lys Thr Asn Met
                100                 105                 110

Lys His Val Ala Gly Ala Ala Ala Gly Ala Val Val Gly Gly Leu
                115                 120                 125

Gly Gly Tyr Met Leu Gly Ser Ala Met Asn Arg Pro Leu Ile His Phe
            130                 135                 140

Gly Asn Asp Tyr Glu Asp Arg Tyr Tyr Arg Glu Asn Met Tyr Arg Tyr
145                 150                 155                 160

Pro Asn Gln Val Tyr Tyr Arg Pro Val Asp Gln Tyr Asn Asn Gln Asn
                165                 170                 175

Thr Phe Val His Asp Cys Val Asn Ile Thr Val Lys Gln His Thr Val
                180                 185                 190

Thr Thr Thr Thr Lys Gly Glu Asn Phe Thr Glu Thr Asp Ile Lys Met
            195                 200                 205

Met Glu Arg Val Val Glu Gln Met Cys Ile Thr Gln Tyr Gln Arg Glu
                210                 215                 220

Ser Glu Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255

<210> SEQ ID NO 10
<211> LENGTH: 256
<212> TYPE: PRT
<213> ORGANISM: Artificial
<220> FEATURE:
<223> OTHER INFORMATION: Mule prion protein

<400> SEQUENCE: 10

Met Val Lys Ser His Ile Gly Ser Trp Ile Leu Val Leu Phe Val Ala
 1               5                  10                  15

Met Trp Ser Asp Val Gly Leu Cys Lys Lys Arg Pro Lys Pro Gly Gly
                 20                  25                  30

Gly Trp Asn Thr Gly Gly Ser Arg Tyr Pro Gly Gln Gly Ser Pro Gly
         35                  40                  45

Gly Asn Arg Tyr Pro Pro Gln Gly Gly Gly Trp Gly Gln Pro His
 50                  55                  60

Gly Gly Gly Trp Gly Gln Pro His Gly Gly Trp Gly Gln Pro His
 65                  70                  75                  80

Gly Gly Gly Trp Gly Gln Pro His Gly Gly Gly Trp Gly Gln Gly
                     85                  90                  95

Gly Thr His Ser Gln Trp Asn Lys Pro Ser Lys Pro Lys Thr Asn Met
                100                 105                 110

Lys His Val Ala Gly Ala Ala Ala Gly Ala Val Val Gly Gly Leu
                115                 120                 125

Gly Gly Tyr Met Leu Gly Ser Ala Met Ser Arg Pro Leu Ile His Phe
            130                 135                 140
```

```
Gly Asn Asp Tyr Glu Asp Arg Tyr Tyr Arg Glu Asn Met Tyr Arg Tyr
145                 150                 155                 160

Pro Asn Gln Val Tyr Tyr Arg Pro Val Asp Gln Tyr Asn Asn Gln Asn
                165                 170                 175

Thr Phe Val His Asp Cys Val Asn Ile Thr Val Lys Gln His Thr Val
            180                 185                 190

Thr Thr Thr Thr Lys Gly Glu Asn Phe Thr Glu Thr Asp Ile Lys Met
        195                 200                 205

Met Glu Arg Val Val Glu Gln Met Cys Ile Thr Gln Tyr Gln Arg Glu
            210                 215                 220

Ser Gln Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255

<210> SEQ ID NO 11
<211> LENGTH: 256
<212> TYPE: PRT
<213> ORGANISM: Artificial
<220> FEATURE:
<223> OTHER INFORMATION: White-tailed deer prion protein

<400> SEQUENCE: 11

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20

```
<210> SEQ ID NO 12
<211> LENGTH: 5
<212> TYPE: PRT
<213> ORGANISM: Artificial
<220> FEATURE:
<223> OTHER INFORMATION: peptide

<400> SEQUENCE: 12

Lys Lys Arg Pro Lys
1               5

<210> SEQ ID NO 13
<211> LENGTH: 22
<212> TYPE: PRT
<213> ORGANISM: Artificial
<220> FEATURE:
<223> OTHER INFORMATION: peptide

<400> SEQUENCE: 13

Met Ala Asn Leu Gly Cys Trp Met Leu Val Leu Phe Val Ala Thr Trp
1               5                   10                  15

Ser Asp Leu Gly Leu Cys
            20

<210> SEQ ID NO 14
<211> LENGTH: 14
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 14

Gly Gly Gly Gln Trp Asn Lys Pro Ser Lys Pro Lys Thr Asn
1               5                   10

<210> SEQ ID NO 15
<211> LENGTH: 15
<212> TYPE: PRT
<213> ORGANISM: Artificial
<220> FEATURE:
<223> OTHER INFORMATION: peptide

<400> SEQUENCE: 15

Gln Trp Asn Lys Pro Ser Lys Pro Lys Thr Asn Met Lys His Val
1               5                   10                  15

<210> SEQ ID NO 16
<211> LENGTH: 30
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (5)..(5)
<223> OTHER INFORMATION: Xaa = Asn or Thr

<400> SEQUENCE: 16

Asn Gln Asn Asn Xaa Phe Val His Asp Cys Val Asn Ile Thr Ile Val
1               5                   10                  15

Lys Gln Glu His Thr Val Thr Thr Thr Thr Lys Gly Glu Asn
            20                  25                  30
```

```
<210> SEQ ID NO 17
<211> LENGTH: 11
<212> TYPE: PRT
<213> ORGANISM: Artificial
<220> FEATURE:
<223> OTHER INFORMATION: peptide

<400> SEQUENCE: 17

Thr Thr Lys Gly Glu Asn Phe Thr Glu Thr Asp
1               5                   10

<210> SEQ ID NO 18
<211> LENGTH: 8
<212> TYPE: PRT
<213> ORGANISM: Artificial
<220> FEATURE:
<223> OTHER INFORMATION: peptide

<400> SEQUENCE: 18

Gly Glu Asn Phe Thr Glu Thr Asp
1               5

<210> SEQ ID NO 19
<211> LENGTH: 38
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (9)..(9)
<223> OTHER INFORMATION: Xaa = Val or Ile
<220> FEATURE:
<221> NAME/KEY: MISC_FEATURE
<222> LOCATION: (11)..(11)
<223> OTHER INFORMATION: Xaa = Met or Ile
<220> FEATURE:
<221> NAME/KEY: MISC_FEATURE
<222> LOCATION: (21)..(21)
<223> OTHER INFORMATION: Xaa = Ile or Val
<220> FEATURE:
<221> NAME/KEY: MISC_FEATURE
<222> LOCATION: (25)..(25)
<223> OTHER INFORMATION: Xaa = Glu or  Gln
<220> FEATURE:
<221> NAME/KEY: MISC_FEATURE
<222> LOCATION: (32)..(32)
<223> OTHER INFORMATION: Xaa = Gln or Asp
<220> FEATURE:
<221> NAME/KEY: MISC_FEATURE
<222> LOCATION: (33)..(33)
<223> OTHER INFORMATION: Gly may be present or absent
<220> FEATURE:
<221> NAME/KEY: MISC_FEATURE
<222> LOCATION: (34)..(34)
<223> OTHER INFORMATION: Arg may be present or absent
<220> FEATURE:
<221> NAME/KEY: MISC_FEATURE
<222> LOCATION: (36)..(36)
<223> OTHER INFORMATION: Xaa = Gly or Ser
<220> FEATURE:
<221> NAME/KEY: MISC_FEATURE
<222> LOCATION: (37)..(37)
<223> OTHER INFORMATION: Xaa = Ser or Ala

<400> SEQUENCE: 19

Gly Glu Asn Phe Thr Glu Thr Asp Xaa Lys Xaa Met Glu Arg Val Val
1               5                   10                  15

Glu Gln Met Cys Xaa Thr Gln Tyr Xaa Glu Ser Gln Ala Tyr Tyr Xaa
            20                  25                  30

Gly Arg Arg Xaa Xaa Ser
```

```
                                    35

<210> SEQ ID NO 20
<211> LENGTH: 63
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (5)..(5)
<223> OTHER INFORMATION: Xaa = Asn or Thr
<220> FEATURE:
<221> NAME/KEY: MISC_FEATURE
<222> LOCATION: (15)..(15)
<223> OTHER INFORMATION: Xaa = Ile or Val
<220> FEATURE:
<221> NAME/KEY: MISC_FEATURE
<222> LOCATION: (17)..(17)
<223> OTHER INFORMATION: Xaa = Gln or Glu
<220> FEATURE:
<221> NAME/KEY: MISC_FEATURE
<222> LOCATION: (34)..(34)
<223> OTHER INFORMATION: Xaa = Val or Ile
<220> FEATURE:
<221> NAME/KEY: MISC_FEATURE
<222> LOCATION: (36)..(36)
<223> OTHER INFORMATION: Xaa = Met or Ile
<220> FEATURE:
<221> NAME/KEY: MISC_FEATURE
<222> LOCATION: (46)..(46)
<223> OTHER INFORMATION: Xaa = Ile or Val
<220> FEATURE:
<221> NAME/KEY: MISC_FEATURE
<222> LOCATION: (50)..(50)
<223> OTHER INFORMATION: Xaa = Glu or Gln
<220> FEATURE:
<221> NAME/KEY: MISC_FEATURE
<222> LOCATION: (57)..(57)
<223> OTHER INFORMATION: Xaa = Gln or Asp
<220> FEATURE:
<221> NAME/KEY: MISC_FEATURE
<222> LOCATION: (58)..(58)
<223> OTHER INFORMATION: Gly may be present or absent
<220> FEATURE:
<221> NAME/KEY: MISC_FEATURE
<222> LOCATION: (59)..(59)
<223> OTHER INFORMATION: Arg may be present or absent
<220> FEATURE:
<221> NAME/KEY: MISC_FEATURE
<222> LOCATION: (61)..(61)
<223> OTHER INFORMATION: Xaa = Gly or Ser
<220> FEATURE:
<221> NAME/KEY: MISC_FEATURE
<222> LOCATION: (62)..(62)
<223> OTHER INFORMATION: Xaa = Ser or Ala

<400> SEQUENCE: 20

Asn Gln Asn Asn Xaa Phe Val His Asp Cys Val Asn Ile Thr Xaa Lys
1               5                   10                  15

Xaa His Thr Val Thr Thr Thr Thr Lys Gly Glu Asn Phe Thr Glu Thr
            20                  25                  30

Asp Xaa Lys Xaa Met Glu Arg Val Val Glu Gln Met Cys Xaa Thr Gln
        35                  40                  45

Tyr Xaa Glu Ser Gln Ala Tyr Tyr Xaa Gly Arg Arg Xaa Xaa Ser
    50                  55                  60

<210> SEQ ID NO 21
<211> LENGTH: 22
<212> TYPE: PRT
<213> ORGANISM: Artificial
<220> FEATURE:
<223> OTHER INFORMATION: peptide
```

```
<220> FEATURE:
<221> NAME/KEY: MISC_FEATURE
<222> LOCATION: (1)..(1)
<223> OTHER INFORMATION: Xaa = Ala, Val, Thr or Met
<220> FEATURE:
<221> NAME/KEY: MISC_FEATURE
<222> LOCATION: (2)..(2)
<223> OTHER INFORMATION: Xaa = Val or Ile
<220> FEATURE:
<221> NAME/KEY: MISC_FEATURE
<222> LOCATION: (20)..(20)
<223> OTHER INFORMATION: Xaa = Ile or Met

<400> SEQUENCE: 21

Xaa Xaa Leu Phe Ser Ser Pro Pro Val Ile Leu Leu Ile Ser Phe Leu
1               5                   10                  15

Ile Phe Leu Xaa Val Gly
            20

<210> SEQ ID NO 22
<211> LENGTH: 36
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Xaa = Asn or Ser
<220> FEATURE:
<221> NAME/KEY: MISC_FEATURE
<222> LOCATION: (4)..(4)
<223> OTHER INFORMATION: Xaa = Trp or Tyr
<220> FEATURE:
<221> NAME/KEY: MISC_FEATURE
<222> LOCATION: (14)..(14)
<223> OTHER INFORMATION: Xaa = His or Tyr
<220> FEATURE:
<221> NAME/KEY: MISC_FEATURE
<222> LOCATION: (25)..(25)
<223> OTHER INFORMATION: Xaa = Met or Val
<220> FEATURE:
<221> NAME/KEY: MISC_FEATURE
<222> LOCATION: (27)..(27)
<223> OTHER INFORMATION: Xaa = Gln, Glu or Arg
<220> FEATURE:
<221> NAME/KEY: MISC_FEATURE
<222> LOCATION: (29)..(29)
<223> OTHER INFORMATION: Xaa = Ser or Asn
<220> FEATURE:
<221> NAME/KEY: MISC_FEATURE
<222> LOCATION: (33)..(33)
<223> OTHER INFORMATION: Xaa = Asn or Thr

<400> SEQUENCE: 22

Gly Xaa Asp Xaa Glu Asp Arg Tyr Tyr Arg Glu Asn Met Xaa Arg Tyr
1               5                   10                  15

Pro Asn Gln Val Tyr Tyr Arg Pro Xaa Asp Xaa Tyr Xaa Asn Gln Asn
                20                  25                  30

Xaa Phe Val His
        35

<210> SEQ ID NO 23
<211> LENGTH: 22
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Xaa = Asn or Thr
```

```
<220> FEATURE:
<221> NAME/KEY: MISC_FEATURE
<222> LOCATION: (12)..(12)
<223> OTHER INFORMATION: Xaa = Ile or Val
<220> FEATURE:
<221> NAME/KEY: MISC_FEATURE
<222> LOCATION: (14)..(14)
<223> OTHER INFORMATION: Xaa = Gln or Glu

<400> SEQUENCE: 23

Asn Xaa Phe Val His Asp Cys Val Asn Ile Thr Xaa Lys Xaa His Thr
1               5                   10                  15

Val Thr Thr Thr Thr Lys
            20

<210> SEQ ID NO 24
<211> LENGTH: 4
<212> TYPE: PRT
<213> ORGANISM: Artificial
<220> FEATURE:
<223> OTHER INFORMATION: peptide

<400> SEQUENCE: 24

Val Tyr Tyr Arg
1

<210> SEQ ID NO 25
<211> LENGTH: 13
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (11)..(11)
<223> OTHER INFORMATION: Xaa = Met or Val
<220> FEATURE:
<221> NAME/KEY: MISC_FEATURE
<222> LOCATION: (13)..(13)
<223> OTHER INFORMATION: Xaa = Gln, Glu or Arg

<400> SEQUENCE: 25

Arg Tyr Pro Asn Gln Val Tyr Tyr Arg Pro Xaa Asp Xaa
1               5                   10

<210> SEQ ID NO 26
<211> LENGTH: 33
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (9)..(9)
<223> OTHER INFORMATION: Gly may be present or absent

<400> SEQUENCE: 26

Lys Lys Arg Pro Lys Pro Gly Gly Gly Trp Asn Thr Gly Gly Ser Arg
1               5                   10                  15

Tyr Pro Gly Gln Gly Ser Pro Gly Gly Asn Arg Tyr Pro Pro Gln Gly
            20                  25                  30

Gly

<210> SEQ ID NO 27
<211> LENGTH: 25
<212> TYPE: PRT
<213> ORGANISM: Artificial
<220> FEATURE:
```

```
<223> OTHER INFORMATION: peptide
<220> FEATURE:
<221> NAME/KEY: MISC_FEATURE
<222> LOCATION: (25)..(25)
<223> OTHER INFORMATION: Gly may be present or absent

<400> SEQUENCE: 27

Trp Asn Thr Gly Gly Ser Arg Tyr Pro Gly Gln Gly Ser Pro Gly Gly
1               5                   10                  15

Asn Arg Tyr Pro Pro Gln Gly Gly Gly
            20                  25

<210> SEQ ID NO 28
<211> LENGTH: 33
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (25)..(25)
<223> OTHER INFORMATION: Gly may be present or absent
<220> FEATURE:
<221> NAME/KEY: MISC_FEATURE
<222> LOCATION: (26)..(26)
<223> OTHER INFORMATION: Xaa = Gly or Thr

<400> SEQUENCE: 28

Trp Asn Thr Gly Gly Ser Arg Tyr Pro Gly Gln Gly Ser Pro Gly Gly
1               5                   10                  15

Asn Arg Tyr Pro Pro Gln Gly Gly Gly Xaa Trp Gly Gln Pro His Gly
            20                  25                  30

Gly

<210> SEQ ID NO 29
<211> LENGTH: 21
<212> TYPE: PRT
<213> ORGANISM: Artificial
<220> FEATURE:
<223> OTHER INFORMATION: peptide

<400> SEQUENCE: 29

Gly Gly Trp Gly Gln Gly Gly Thr His Ser Gln Trp Asn Lys Pro Ser
1               5                   10                  15

Lys Pro Lys Thr Asn
            20

<210> SEQ ID NO 30
<211> LENGTH: 16
<212> TYPE: PRT
<213> ORGANISM: Artificial
<220> FEATURE:
<223> OTHER INFORMATION: peptide

<400> SEQUENCE: 30

Gly Gly Thr His Ser Gln Trp Asn Lys Pro Ser Lys Pro Lys Thr Asn
1               5                   10                  15

<210> SEQ ID NO 31
<211> LENGTH: 49
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (25)..(25)
```

```
<223> OTHER INFORMATION: Gly may be present or absent
<220> FEATURE:
<221> NAME/KEY: MISC_FEATURE
<222> LOCATION: (26)..(26)
<223> OTHER INFORMATION: Xaa =  Gly or Thr

<400> SEQUENCE: 31

Trp Asn Thr Gly Gly Ser Arg Tyr Pro Gly Gln Gly Ser Pro Gly Gly
1               5                   10                  15

Asn Arg Tyr Pro Pro Gln Gly Gly Xaa Trp Gly Gln Pro His Gly
            20                  25                  30

Gly Gly Trp Gly Gln Pro His Gly Gly Trp Gly Gln Pro His Gly
        35                  40                  45

Gly

<210> SEQ ID NO 32
<211> LENGTH: 8
<212> TYPE: PRT
<213> ORGANISM: Artificial
<220> FEATURE:
<223> OTHER INFORMATION: peptide

<400> SEQUENCE: 32

Gly Gln Pro His Gly Gly Gly Trp
1               5

<210> SEQ ID NO 33
<211> LENGTH: 21
<212> TYPE: PRT
<213> ORGANISM: Artificial
<220> FEATURE:
<223> OTHER INFORMATION: peptide

<400> SEQUENCE: 33

Arg Pro Ile Ile His Phe Gly Ser Asp Tyr Glu Asp Arg Tyr Tyr Arg
1               5                   10                  15

Glu Asn Met His Arg
            20

<210> SEQ ID NO 34
<211> LENGTH: 21
<212> TYPE: PRT
<213> ORGANISM: Artificial
<220> FEATURE:
<223> OTHER INFORMATION: peptide

<400> SEQUENCE: 34

Arg Pro Met Ile His Phe Gly Asn Asp Trp Glu Asp Arg Tyr Tyr Arg
1               5                   10                  15

Glu Asn Met Tyr Arg
            20

<210> SEQ ID NO 35
<211> LENGTH: 38
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(4)
<223> OTHER INFORMATION: Gly may be present or absent
<220> FEATURE:
<221> NAME/KEY: MISC_FEATURE
<222> LOCATION: (6)..(7)
<223> OTHER INFORMATION: Gly may be present or absent
```

```
<220> FEATURE:
<221> NAME/KEY: MISC_FEATURE
<222> LOCATION: (34)..(37)
<223> OTHER INFORMATION: Gly may be present or absent

<400> SEQUENCE: 35

Gly Gly Gly Gly Cys Gly Gly Gly Gly Trp Gly Gln Gly Gly Gly Thr
1               5                   10                  15

His Asn Gln Trp Asn Lys Pro Ser Lys Pro Lys Thr Asn Leu Lys His
            20                  25                  30

Val Gly Gly Gly Gly Cys
        35

<210> SEQ ID NO 36
<211> LENGTH: 30
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(4)
<223> OTHER INFORMATION: Gly may be present or absent

<400> SEQUENCE: 36

Gly Gly Gly Gly Gly Gly Trp Gly Gln Gly Gly Gly Thr His Asn Gln
1               5                   10                  15

Trp Asn Lys Pro Ser Lys Pro Lys Thr Asn Leu Lys His Val
            20                  25                  30

<210> SEQ ID NO 37
<211> LENGTH: 30
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (27)..(30)
<223> OTHER INFORMATION: Gly may be present or absent

<400> SEQUENCE: 37

Gly Gly Trp Gly Gln Gly Gly Gly Thr His Asn Gln Trp Asn Lys Pro
1               5                   10                  15

Ser Lys Pro Lys Thr Asn Leu Lys His Val Gly Gly Gly Gly
            20                  25                  30

<210> SEQ ID NO 38
<211> LENGTH: 4
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: Xaa = Met or Leu
<220> FEATURE:
<221> NAME/KEY: MISC_FEATURE
<222> LOCATION: (4)..(4)
<223> OTHER INFORMATION: Xaa = Met or Val

<400> SEQUENCE: 38

Xaa Lys His Xaa
1

<210> SEQ ID NO 39
```

```
<211> LENGTH: 9
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (6)..(6)
<223> OTHER INFORMATION: Xaa = Met or Leu
<220> FEATURE:
<221> NAME/KEY: MISC_FEATURE
<222> LOCATION: (9)..(9)
<223> OTHER INFORMATION: Xaa = Met or Val

<400> SEQUENCE: 39

Lys Pro Lys Thr Asn Xaa Lys His Xaa
1               5

<210> SEQ ID NO 40
<211> LENGTH: 34
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (2)..(3)
<223> OTHER INFORMATION: Gly may be present or absent
<220> FEATURE:
<221> NAME/KEY: MISC_FEATURE
<222> LOCATION: (30)..(33)
<223> OTHER INFORMATION: Gly may be present or absent

<400> SEQUENCE: 40

Cys Gly Gly Gly Gly Trp Gly Gln Gly Gly Thr His Asn Gln Trp
1               5                   10                  15

Asn Lys Pro Ser Lys Pro Lys Thr Asn Leu Lys His Val Gly Gly Gly
            20                  25                  30

Gly Cys

<210> SEQ ID NO 41
<211> LENGTH: 25
<212> TYPE: PRT
<213> ORGANISM: Artificial
<220> FEATURE:
<223> OTHER INFORMATION: peptide

<400> SEQUENCE: 41

Ser Arg Pro Ile Ile His Phe Gly Ser Asp Tyr Glu Asp Arg Tyr Tyr
1               5                   10                  15

Arg Glu Asn Met His Arg Tyr Pro Asn
            20                  25

<210> SEQ ID NO 42
<211> LENGTH: 23
<212> TYPE: PRT
<213> ORGANISM: Artificial
<220> FEATURE:
<223> OTHER INFORMATION: peptide

<400> SEQUENCE: 42

Pro Met Ile His Phe Gly Asn Asp Trp Glu Asp Arg Tyr Tyr Arg Glu
1               5                   10                  15

Asn Met Tyr Arg Pro Val Asp
            20

<210> SEQ ID NO 43
```

```
<211> LENGTH: 22
<212> TYPE: PRT
<213> ORGANISM: Artificial
<220> FEATURE:
<223> OTHER INFORMATION: peptide

<400> SEQUENCE: 43

Ala Gly Ala Ala Ala Ala Gly Ala Val Val Gly Gly Leu Gly Gly Tyr
1               5                   10                  15

Met Leu Gly Ser Ala Met
            20

<210> SEQ ID NO 44
<211> LENGTH: 24
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (22)..(24)
<223> OTHER INFORMATION: Gly may be present or absent

<400> SEQUENCE: 44

Arg Pro Met Ile His Phe Gly Asn Asp Trp Glu Asp Arg Tyr Tyr Arg
1               5                   10                  15

Glu Asn Met Tyr Arg Gly Gly Gly
            20

<210> SEQ ID NO 45
<211> LENGTH: 26
<212> TYPE: PRT
<213> ORGANISM: Artificial
<220> FEATURE:
<223> OTHER INFORMATION: peptide

<400> SEQUENCE: 45

Gly Gly Gly Arg Pro Met Ile His Phe Gly Asn Asp Trp Glu Asp Arg
1               5                   10                  15

Tyr Tyr Arg Glu Asn Met Tyr Arg Gly Gly
            20                  25

<210> SEQ ID NO 46
<211> LENGTH: 31
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(2)
<223> OTHER INFORMATION: Gly may be present or absent
<220> FEATURE:
<221> NAME/KEY: MISC_FEATURE
<222> LOCATION: (4)..(6)
<223> OTHER INFORMATION: Gly may be present or absent
<220> FEATURE:
<221> NAME/KEY: MISC_FEATURE
<222> LOCATION: (28)..(30)
<223> OTHER INFORMATION: Gly may be present or absent

<400> SEQUENCE: 46

Gly Gly Cys Gly Gly Gly Arg Pro Met Ile His Phe Gly Asn Asp Trp
1               5                   10                  15

Glu Asp Arg Tyr Tyr Arg Glu Asn Met Tyr Arg Gly Gly Gly Cys
            20                  25                  30
```

```
<210> SEQ ID NO 47
<211> LENGTH: 15
<212> TYPE: PRT
<213> ORGANISM: Artificial
<220> FEATURE:
<223> OTHER INFORMATION: peptide

<400> SEQUENCE: 47

Ala Gly Ala Ala Ala Ala Gly Ala Val Val Gly Gly Leu Gly Gly
1               5                   10                  15

<210> SEQ ID NO 48
<211> LENGTH: 5
<212> TYPE: PRT
<213> ORGANISM: Artificial
<220> FEATURE:
<223> OTHER INFORMATION: peptide

<400> SEQUENCE: 48

Gly Gly Leu Gly Gly
1               5

<210> SEQ ID NO 49
<211> LENGTH: 3
<212> TYPE: PRT
<213> ORGANISM: Artificial
<220> FEATURE:
<223> OTHER INFORMATION: peptide

<400> SEQUENCE: 49

Leu Gly Ser
1

<210> SEQ ID NO 50
<211> LENGTH: 14
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (12)..(14)
<223> OTHER INFORMATION: Gly may be present or absent

<400> SEQUENCE: 50

Gln Trp Asn Lys Pro Ser Lys Pro Lys Thr Asn Gly Gly Gly
1               5                   10

<210> SEQ ID NO 51
<211> LENGTH: 25
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (12)..(14)
<223> OTHER INFORMATION: Gly may be present or absent

<400> SEQUENCE: 51

Gln Trp Asn Lys Pro Ser Lys Pro Lys Thr Asn Gly Gly Gly Gln Trp
1               5                   10                  15

Asn Lys Pro Ser Lys Pro Lys Thr Asn
            20                  25

<210> SEQ ID NO 52
<211> LENGTH: 18
<212> TYPE: PRT
```

```
<213> ORGANISM: Artificial
<220> FEATURE:
<223> OTHER INFORMATION: peptide
<220> FEATURE:
<221> NAME/KEY: MISC_FEATURE
<222> LOCATION: (16)..(18)
<223> OTHER INFORMATION: Gly may be present or absent

<400> SEQUENCE: 52

Gln Trp Asn Lys Pro Ser Lys Pro Lys Thr Asn Leu Lys His Val Gly
1               5                   10                  15

Gly Gly

<210> SEQ ID NO 53
<211> LENGTH: 22
<212> TYPE: PRT
<213> ORGANISM: Artificial
<220> FEATURE:
<223> OTHER INFORMATION: peptide

<400> SEQUENCE: 53

Gly Gly Trp Gly Gln Gly Gly Gly Thr His Asn Gln Trp Asn Lys Pro
1               5                   10                  15

Ser Lys Pro Lys Thr Asn
            20

<210> SEQ ID NO 54
<211> LENGTH: 16
<212> TYPE: PRT
<213> ORGANISM: Artificial
<220> FEATURE:
<223> OTHER INFORMATION: peptide

<400> SEQUENCE: 54

Gly Gly Thr His Asn Gln Trp Asn Lys Pro Ser Lys Pro Lys Thr Asn
1               5                   10                  15

<210> SEQ ID NO 55
<211> LENGTH: 25
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 55

Gly Gly Gly Ala Gly Ala Ala Ala Gly Ala Val Val Gly Gly Leu
1               5                   10                  15

Gly Gly Tyr Met Leu Gly Ser Ala Met
            20                  25

<210> SEQ ID NO 56
<211> LENGTH: 18
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 56

Gly Gly Gly Ala Gly Ala Ala Ala Ala Gly Ala Val Val Gly Gly Leu
```

-continued

```
1               5                   10                  15

Gly Gly

<210> SEQ ID NO 57
<211> LENGTH: 25
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Lys may be present or absent

<400> SEQUENCE: 57

Lys Lys Lys Ala Gly Ala Ala Ala Gly Ala Val Val Gly Gly Leu
1               5                   10                  15

Gly Gly Tyr Met Leu Gly Ser Ala Met
            20                  25

<210> SEQ ID NO 58
<211> LENGTH: 9
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (8)..(8)
<223> OTHER INFORMATION: Xaa = Ser or Asn

<400> SEQUENCE: 58

Tyr Met Leu Gly Ser Ala Met Xaa Arg
1               5

<210> SEQ ID NO 59
<211> LENGTH: 6
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: Xaa = Ser or Asn
<220> FEATURE:
<221> NAME/KEY: MISC_FEATURE
<222> LOCATION: (4)..(4)
<223> OTHER INFORMATION: Xaa = Met, Ile or Leu
<220> FEATURE:
<221> NAME/KEY: MISC_FEATURE
<222> LOCATION: (5)..(5)
<223> OTHER INFORMATION: Xaa = Ile or Leu

<400> SEQUENCE: 59

Xaa Arg Pro Xaa Xaa His
1               5

<210> SEQ ID NO 60
<211> LENGTH: 13
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (8)..(8)
<223> OTHER INFORMATION: Xaa = Ser or Asn
<220> FEATURE:
<221> NAME/KEY: MISC_FEATURE
```

```
<222> LOCATION: (11)..(11)
<223> OTHER INFORMATION: Xaa = Met, Ile or Leu
<220> FEATURE:
<221> NAME/KEY: MISC_FEATURE
<222> LOCATION: (12)..(12)
<223> OTHER INFORMATION: Xaa = Ile or Leu

<400> SEQUENCE: 60

Tyr Met Leu Gly Ser Ala Met Xaa Arg Pro Xaa Xaa His
1               5                   10

<210> SEQ ID NO 61
<211> LENGTH: 17
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (8)..(8)
<223> OTHER INFORMATION: Xaa = Ser or Asn
<220> FEATURE:
<221> NAME/KEY: MISC_FEATURE
<222> LOCATION: (11)..(11)
<223> OTHER INFORMATION: Xaa = Met, Ile or Leu
<220> FEATURE:
<221> NAME/KEY: MISC_FEATURE
<222> LOCATION: (12)..(12)
<223> OTHER INFORMATION: Xaa = Ile or Leu
<220> FEATURE:
<221> NAME/KEY: MISC_FEATURE
<222> LOCATION: (16)..(16)
<223> OTHER INFORMATION: Xaa = Asn or Ser

<400> SEQUENCE: 61

Tyr Met Leu Gly Ser Ala Met Xaa Arg Pro Xaa Xaa His Phe Gly Xaa
1               5                   10                  15

Asp

<210> SEQ ID NO 62
<211> LENGTH: 25
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: Xaa = Trp or Tyr
<220> FEATURE:
<221> NAME/KEY: MISC_FEATURE
<222> LOCATION: (11)..(11)
<223> OTHER INFORMATION: Xaa = His or Tyr
<220> FEATURE:
<221> NAME/KEY: MISC_FEATURE
<222> LOCATION: (22)..(22)
<223> OTHER INFORMATION: Xaa = Met or Val
<220> FEATURE:
<221> NAME/KEY: MISC_FEATURE
<222> LOCATION: (24)..(24)
<223> OTHER INFORMATION: Xaa = Gln, Glu or Arg

<400> SEQUENCE: 62

Xaa Glu Asp Arg Tyr Tyr Arg Glu Asn Met Xaa Arg Tyr Pro Asn Gln
1               5                   10                  15

Val Tyr Tyr Arg Pro Xaa Asp Xaa Tyr
            20                  25

<210> SEQ ID NO 63
<211> LENGTH: 30
<212> TYPE: PRT
```

```
<213> ORGANISM: Artificial
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: Xaa = Trp or Tyr
<220> FEATURE:
<221> NAME/KEY: MISC_FEATURE
<222> LOCATION: (11)..(11)
<223> OTHER INFORMATION: Xaa = His or Tyr
<220> FEATURE:
<221> NAME/KEY: MISC_FEATURE
<222> LOCATION: (22)..(22)
<223> OTHER INFORMATION: Xaa = Met or Val
<220> FEATURE:
<221> NAME/KEY: MISC_FEATURE
<222> LOCATION: (24)..(24)
<223> OTHER INFORMATION: Xaa = Gln, Glu or Arg
<220> FEATURE:
<221> NAME/KEY: MISC_FEATURE
<222> LOCATION: (26)..(26)
<223> OTHER INFORMATION: Xaa = Ser or Asn
<220> FEATURE:
<221> NAME/KEY: MISC_FEATURE
<222> LOCATION: (30)..(30)
<223> OTHER INFORMATION: Xaa = Asn or Tyr

<400> SEQUENCE: 63

Xaa Glu Asp Arg Tyr Tyr Arg Glu Asn Met Xaa Arg Tyr Pro Asn Gln
1               5                   10                  15

Val Tyr Tyr Arg Pro Xaa Asp Xaa Tyr Xaa Asn Gln Asn Xaa
            20                  25                  30

<210> SEQ ID NO 64
<211> LENGTH: 8
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Xaa = Gln, Glu or Arg
<220> FEATURE:
<221> NAME/KEY: MISC_FEATURE
<222> LOCATION: (4)..(4)
<223> OTHER INFORMATION: Xaa = Ser or Asn
<220> FEATURE:
<221> NAME/KEY: MISC_FEATURE
<222> LOCATION: (8)..(8)
<223> OTHER INFORMATION: Xaa = Asn or Thr

<400> SEQUENCE: 64

Asp Xaa Tyr Xaa Asn Gln Asn Xaa
1               5

<210> SEQ ID NO 65
<211> LENGTH: 18
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Lys may be present or absent

<400> SEQUENCE: 65

Lys Lys Lys Ala Gly Ala Ala Ala Gly Ala Val Val Gly Gly Leu
1               5                   10                  15

Gly Gly
```

```
<210> SEQ ID NO 66
<211> LENGTH: 24
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 66

Gly Gly Gly Lys Lys Arg Pro Lys Pro Gly Gly Trp Asn Thr Gly Gly
1               5                   10                  15

Ser Arg Tyr Pro Gly Gln Gly Ser
            20

<210> SEQ ID NO 67
<211> LENGTH: 16
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 67

Gly Gly Gly Lys Lys Arg Pro Lys Pro Gly Gly Trp Asn Thr Gly Gly
1               5                   10                  15

<210> SEQ ID NO 68
<211> LENGTH: 11
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 68

Gly Gly Gly Lys Lys Arg Pro Lys Pro Gly Gly
1               5                   10

<210> SEQ ID NO 69
<211> LENGTH: 23
<212> TYPE: PRT
<213> ORGANISM: Artificial
<220> FEATURE:
<223> OTHER INFORMATION: peptide

<400> SEQUENCE: 69

Pro His Gly Gly Gly Trp Gly Gln His Gly Gly Ser Trp Gly Gln Pro
1               5                   10                  15

His Gly Gly Ser Trp Gly Gln
            20

<210> SEQ ID NO 70
<211> LENGTH: 16
<212> TYPE: PRT
<213> ORGANISM: Artificial
<220> FEATURE:
<223> OTHER INFORMATION: peptide
```

```
<400> SEQUENCE: 70

Pro His Gly Gly Gly Trp Gly Gln Pro His Gly Gly Ser Trp Gly Gln
1               5                   10                  15

<210> SEQ ID NO 71
<211> LENGTH: 8
<212> TYPE: PRT
<213> ORGANISM: Artificial
<220> FEATURE:
<223> OTHER INFORMATION: peptide

<400> SEQUENCE: 71

Pro His Gly Gly Gly Trp Gly Gln
1               5

<210> SEQ ID NO 72
<211> LENGTH: 20
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 72

Gly Gly Gly Lys Lys Arg Pro Lys Pro Gly Gly Lys Lys Arg Pro
1               5                   10                  15

Lys Pro Gly Gly
            20

<210> SEQ ID NO 73
<211> LENGTH: 11
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 73

Gly Gly Gly Gly Pro Lys Arg Lys Gly Pro Lys
1               5                   10

<210> SEQ ID NO 74
<211> LENGTH: 16
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 74

Gly Gly Gly Trp Asn Thr Gly Gly Ser Arg Tyr Pro Gly Gln Gly Ser
1               5                   10                  15

<210> SEQ ID NO 75
<211> LENGTH: 12
<212> TYPE: PRT
<213> ORGANISM: Artificial
<220> FEATURE:
<223> OTHER INFORMATION: peptide
```

```
<220> FEATURE:
<221> NAME/KEY: MISC_FEATURE
<222> LOCATION: (1)..(3)
<223> OTHER INFORMATION: Gly may be present or absent

<400> SEQUENCE: 75

Gly Gly Gly Trp Asn Lys Pro Ser Lys Pro Lys Thr
1               5                   10

<210> SEQ ID NO 76
<211> LENGTH: 27
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent
<220> FEATURE:
<221> NAME/KEY: MISC_FEATURE
<222> LOCATION: (25)..(26)
<223> OTHER INFORMATION: Gly may be present or absent

<400> SEQUENCE: 76

Gly Gly Gly Arg Pro Met Ile His Phe Gly Asn Asp Trp Glu Asp Arg
1               5                   10                  15

Tyr Tyr Arg Glu Asn Met Tyr Arg Gly Gly Cys
            20                  25

<210> SEQ ID NO 77
<211> LENGTH: 18
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (16)..(18)
<223> OTHER INFORMATION: Gly may be present or absent

<400> SEQUENCE: 77

Gln Trp Asn Lys Pro Ser Lys Pro Lys Thr Asn Leu Lys His Val Gly
1               5                   10                  15

Gly Gly

<210> SEQ ID NO 78
<211> LENGTH: 25
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 78

Gly Gly Gly Ala Gly Ala Ala Ala Gly Ala Val Val Gly Gly Leu
1               5                   10                  15

Gly Gly Tyr Met Leu Gly Ser Ala Met
            20                  25

<210> SEQ ID NO 79
<211> LENGTH: 10
<212> TYPE: PRT
<213> ORGANISM: Artificial
<220> FEATURE:
```

```
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 79

Gly Gly Gly Asn Lys Pro Ser Lys Pro Lys
1               5                   10

<210> SEQ ID NO 80
<211> LENGTH: 9
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 80

Gly Gly Gly Lys Pro Ser Lys Pro Lys
1               5

<210> SEQ ID NO 81
<211> LENGTH: 23
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 81

Gly Gly Gly Lys Lys Arg Pro Lys Pro Gly Gly Gly Gln Trp Asn Lys
1               5                   10                  15

Pro Ser Lys Pro Lys Thr Asn
            20

<210> SEQ ID NO 82
<211> LENGTH: 28
<212> TYPE: PRT
<213> ORGANISM: Artificial
<220> FEATURE:
<223> OTHER INFORMATION: peptide

<400> SEQUENCE: 82

Lys Lys Lys Ala Gly Ala Ala Ala Gly Ala Val Val Gly Gly Leu
1               5                   10                  15

Gly Gly Tyr Met Leu Gly Ser Ala Met Asp Asp Asp
            20                  25

<210> SEQ ID NO 83
<211> LENGTH: 25
<212> TYPE: PRT
<213> ORGANISM: Artificial
<220> FEATURE:
<223> OTHER INFORMATION: peptide

<400> SEQUENCE: 83

Asp Asp Asp Ala Gly Ala Ala Ala Gly Ala Val Val Gly Gly Leu
1               5                   10                  15

Gly Gly Tyr Met Leu Gly Ser Ala Met
            20                  25
```

-continued

<210> SEQ ID NO 84
<211> LENGTH: 28
<212> TYPE: PRT
<213> ORGANISM: Artificial
<220> FEATURE:
<223> OTHER INFORMATION: peptide

<400> SEQUENCE: 84

Lys Lys Lys Ala Gly Ala Ala Ala Gly Ala Val Val Gly Gly Leu
1               5                   10                  15

Gly Gly Tyr Met Leu Gly Ser Ala Met Lys Lys Lys
            20                  25

<210> SEQ ID NO 85
<211> LENGTH: 11
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 85

Gly Gly Gly Lys Lys Lys Lys Lys Lys Lys
1               5                   10

<210> SEQ ID NO 86
<211> LENGTH: 28
<212> TYPE: PRT
<213> ORGANISM: Artificial
<220> FEATURE:
<223> OTHER INFORMATION: peptide

<400> SEQUENCE: 86

Asp Asp Asp Ala Gly Ala Ala Ala Gly Ala Val Val Gly Gly Leu
1               5                   10                  15

Gly Gly Tyr Met Leu Gly Ser Ala Met Asp Asp Asp
            20                  25

<210> SEQ ID NO 87
<211> LENGTH: 14
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 87

Gly Gly Gly Asn Asn Lys Gln Ser Pro Trp Pro Thr Lys Lys
1               5                   10

<210> SEQ ID NO 88
<211> LENGTH: 23
<212> TYPE: PRT
<213> ORGANISM: Artificial
<220> FEATURE:
<223> OTHER INFORMATION: peptide

<400> SEQUENCE: 88

Asp Lys Asp Lys Gly Gly Val Gly Ala Leu Ala Gly Ala Ala Val Ala
1               5                   10                  15

```
Ala Gly Gly Asp Lys Asp Lys
            20

<210> SEQ ID NO 89
<211> LENGTH: 14
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 89

Gly Gly Gly Gln Ala Asn Lys Pro Ser Lys Pro Lys Thr Asn
1               5                   10

<210> SEQ ID NO 90
<211> LENGTH: 14
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 90

Gly Gly Gly Gln Trp Asn Lys Ala Ser Lys Pro Lys Thr Asn
1               5                   10

<210> SEQ ID NO 91
<211> LENGTH: 14
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 91

Gly Gly Gly Gln Trp Asn Lys Pro Ser Lys Ala Lys Thr Asn
1               5                   10

<210> SEQ ID NO 92
<211> LENGTH: 14
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 92

Gly Gly Gly Gln Trp Asn Ala Pro Ser Lys Pro Lys Thr Asn
1               5                   10

<210> SEQ ID NO 93
<211> LENGTH: 14
<212> TYPE: PRT
<213> ORGANISM: Artificial
<220> FEATURE:
<223> OTHER INFORMATION: peptide
```

```
<220> FEATURE:
<221> NAME/KEY: MISC_FEATURE
<222> LOCATION: (1)..(3)
<223> OTHER INFORMATION: Gly may be present or absent

<400> SEQUENCE: 93

Gly Gly Gly Gln Trp Asn Lys Pro Ser Ala Pro Lys Thr Asn
1               5                   10

<210> SEQ ID NO 94
<211> LENGTH: 14
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 94

Gly Gly Gly Gln Trp Asn Lys Pro Ser Lys Pro Ala Thr Asn
1               5                   10

<210> SEQ ID NO 95
<211> LENGTH: 14
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 95

Gly Gly Gly Gln Trp Asn Lys Ala Ser Lys Ala Lys Thr Asn
1               5                   10

<210> SEQ ID NO 96
<211> LENGTH: 11
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 96

Gly Gly Gly Lys Lys Arg Ala Lys Pro Gly Gly
1               5                   10

<210> SEQ ID NO 97
<211> LENGTH: 11
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 97

Gly Gly Gly Lys Lys Arg Pro Lys Ala Gly Gly
1               5                   10
```

```
<210> SEQ ID NO 98
<211> LENGTH: 11
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly is present or absent

<400> SEQUENCE: 98

Gly Gly Gly Lys Lys Arg Ala Lys Ala Gly Gly
1               5                   10

<210> SEQ ID NO 99
<211> LENGTH: 14
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 99

Gly Gly Gly Gln Trp Asn Lys Ala Ser Lys Pro Lys Thr Asn
1               5                   10

<210> SEQ ID NO 100
<211> LENGTH: 14
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 100

Gly Gly Gly Gln Trp Ala Lys Pro Ser Lys Pro Lys Thr Asn
1               5                   10

<210> SEQ ID NO 101
<211> LENGTH: 14
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 101

Gly Gly Gly Gln Trp Asn Lys Pro Ala Lys Pro Lys Thr Asn
1               5                   10

<210> SEQ ID NO 102
<211> LENGTH: 14
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent
```

```
<400> SEQUENCE: 102

Gly Gly Gly Gln Trp Asn Lys Pro Ser Lys Pro Lys Ala Asn
1               5                   10

<210> SEQ ID NO 103
<211> LENGTH: 14
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 103

Gly Gly Gly Gln Trp Asn Lys Pro Ser Lys Pro Lys Thr Ala
1               5                   10

<210> SEQ ID NO 104
<211> LENGTH: 11
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 104

Gly Gly Gly Ala Lys Arg Pro Lys Pro Gly Gly
1               5                   10

<210> SEQ ID NO 105
<211> LENGTH: 11
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 105

Gly Gly Gly Lys Ala Arg Pro Lys Pro Gly Gly
1               5                   10

<210> SEQ ID NO 106
<211> LENGTH: 11
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 106

Gly Gly Gly Lys Lys Ala Pro Lys Pro Gly Gly
1               5                   10

<210> SEQ ID NO 107
<211> LENGTH: 11
<212> TYPE: PRT
<213> ORGANISM: Artificial
<220> FEATURE:
```

```
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 107

Gly Gly Gly Lys Lys Arg Pro Ala Pro Gly Gly
1               5                   10

<210> SEQ ID NO 108
<211> LENGTH: 11
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 108

Gly Gly Gly Lys Lys Ala Pro Lys Ala Gly Gly
1               5                   10

<210> SEQ ID NO 109
<211> LENGTH: 11
<212> TYPE: PRT
<213> ORGANISM: Artificial
<220> FEATURE:
<223> OTHER INFORMATION: peptoid
<220> FEATURE:
<221> NAME/KEY: MISC_FEATURE
<222> LOCATION: (8)..(8)
<223> OTHER INFORMATION: Xaa = N-(S)-(1-phenylethyl)glycine

<400> SEQUENCE: 109

Gln Trp Asn Lys Pro Ser Lys Xaa Lys Thr Asn
1               5                   10

<210> SEQ ID NO 110
<211> LENGTH: 11
<212> TYPE: PRT
<213> ORGANISM: Artificial
<220> FEATURE:
<223> OTHER INFORMATION: peptoid
<220> FEATURE:
<221> NAME/KEY: MISC_FEATURE
<222> LOCATION: (8)..(8)
<223> OTHER INFORMATION: Xaa = N-(4-hydroxyphenyl)glycine

<400> SEQUENCE: 110

Gln Trp Asn Lys Pro Ser Lys Xaa Lys Thr Asn
1               5                   10

<210> SEQ ID NO 111
<211> LENGTH: 11
<212> TYPE: PRT
<213> ORGANISM: Artificial
<220> FEATURE:
<223> OTHER INFORMATION: peptoid
<220> FEATURE:
<221> NAME/KEY: MISC_FEATURE
<222> LOCATION: (8)..(8)
<223> OTHER INFORMATION: Xaa = N-(cyclopropylmethyl)glycine

<400> SEQUENCE: 111

Gln Trp Asn Lys Pro Ser Lys Xaa Lys Thr Asn
1               5                   10
```

```
<210> SEQ ID NO 112
<211> LENGTH: 11
<212> TYPE: PRT
<213> ORGANISM: Artificial
<220> FEATURE:
<223> OTHER INFORMATION: peptoid
<220> FEATURE:
<221> NAME/KEY: MISC_FEATURE
<222> LOCATION: (8)..(8)
<223> OTHER INFORMATION: Xaa = N-(isopropyl)glycine

<400> SEQUENCE: 112

Gln Trp Asn Lys Pro Ser Lys Xaa Lys Thr Asn
1               5                   10

<210> SEQ ID NO 113
<211> LENGTH: 11
<212> TYPE: PRT
<213> ORGANISM: Artificial
<220> FEATURE:
<223> OTHER INFORMATION: peptoid
<220> FEATURE:
<221> NAME/KEY: MISC_FEATURE
<222> LOCATION: (8)..(8)
<223> OTHER INFORMATION: Xaa = N-(3,5-dimethoxybenzyl)glycine

<400> SEQUENCE: 113

Gln Trp Asn Lys Pro Ser Lys Xaa Lys Thr Asn
1               5                   10

<210> SEQ ID NO 114
<211> LENGTH: 11
<212> TYPE: PRT
<213> ORGANISM: Artificial
<220> FEATURE:
<223> OTHER INFORMATION: peptoid
<220> FEATURE:
<221> NAME/KEY: MISC_FEATURE
<222> LOCATION: (8)..(8)
<223> OTHER INFORMATION: Xaa = N-butylglycine

<400> SEQUENCE: 114

Gln Trp Asn Lys Pro Ser Lys Xaa Lys Thr Asn
1               5                   10

<210> SEQ ID NO 115
<211> LENGTH: 11
<212> TYPE: PRT
<213> ORGANISM: Artificial
<220> FEATURE:
<223> OTHER INFORMATION: peptoid
<220> FEATURE:
<221> NAME/KEY: MISC_FEATURE
<222> LOCATION: (5)..(5)
<223> OTHER INFORMATION: Xaa = N-(cyclopropylmethyl)glycine

<400> SEQUENCE: 115

Gln Trp Asn Lys Xaa Ser Lys Pro Lys Thr Asn
1               5                   10

<210> SEQ ID NO 116
<211> LENGTH: 11
<212> TYPE: PRT
<213> ORGANISM: Artificial
<220> FEATURE:
<223> OTHER INFORMATION: peptoid
<220> FEATURE:
<221> NAME/KEY: MISC_FEATURE
<222> LOCATION: (5)..(5)
<223> OTHER INFORMATION: Xaa = N-(isopropyl)glycine
```

```
<400> SEQUENCE: 116

Gln Trp Asn Lys Xaa Ser Lys Pro Lys Thr Asn
1               5                   10

<210> SEQ ID NO 117
<211> LENGTH: 11
<212> TYPE: PRT
<213> ORGANISM: Artificial
<220> FEATURE:
<223> OTHER INFORMATION: peptoid
<220> FEATURE:
<221> NAME/KEY: MISC_FEATURE
<222> LOCATION: (5)..(5)
<223> OTHER INFORMATION: Xaa = N-(3,5-dimethoxybenzyl)glycine

<400> SEQUENCE: 117

Gln Trp Asn Lys Xaa Ser Lys Pro Lys Thr Asn
1               5                   10

<210> SEQ ID NO 118
<211> LENGTH: 11
<212> TYPE: PRT
<213> ORGANISM: Artificial
<220> FEATURE:
<223> OTHER INFORMATION: peptoid
<220> FEATURE:
<221> NAME/KEY: MISC_FEATURE
<222> LOCATION: (5)..(5)
<223> OTHER INFORMATION: Xaa = N-butylglycine

<400> SEQUENCE: 118

Gln Trp Asn Lys Xaa Ser Lys Pro Lys Thr Asn
1               5                   10

<210> SEQ ID NO 119
<211> LENGTH: 8
<212> TYPE: PRT
<213> ORGANISM: Artificial
<220> FEATURE:
<223> OTHER INFORMATION: peptoid
<220> FEATURE:
<221> NAME/KEY: MISC_FEATURE
<222> LOCATION: (6)..(6)
<223> OTHER INFORMATION: Xaa = N-butylglycine

<400> SEQUENCE: 119

Lys Lys Arg Pro Lys Xaa Gly Gly
1               5

<210> SEQ ID NO 120
<211> LENGTH: 8
<212> TYPE: PRT
<213> ORGANISM: Artificial
<220> FEATURE:
<223> OTHER INFORMATION: peptoid
<220> FEATURE:
<221> NAME/KEY: MISC_FEATURE
<222> LOCATION: (6)..(6)
<223> OTHER INFORMATION: Xaa = N-(3,5-dimethoxybenzyl)glycine

<400> SEQUENCE: 120

Lys Lys Arg Pro Lys Xaa Gly Gly
1               5

<210> SEQ ID NO 121
<211> LENGTH: 8
<212> TYPE: PRT
<213> ORGANISM: Artificial
```

```
<220> FEATURE:
<223> OTHER INFORMATION: peptoid
<220> FEATURE:
<221> NAME/KEY: MISC_FEATURE
<222> LOCATION: (6)..(6)
<223> OTHER INFORMATION: Xaa = N-(isopropyl)glycine

<400> SEQUENCE: 121

Lys Lys Arg Pro Lys Xaa Gly Gly
1               5

<210> SEQ ID NO 122
<211> LENGTH: 8
<212> TYPE: PRT
<213> ORGANISM: Artificial
<220> FEATURE:
<223> OTHER INFORMATION: peptoid
<220> FEATURE:
<221> NAME/KEY: MISC_FEATURE
<222> LOCATION: (6)..(6)
<223> OTHER INFORMATION: Xaa = N-(cyclopropylmethyl)glycine

<400> SEQUENCE: 122

Lys Lys Arg Pro Lys Xaa Gly Gly
1               5

<210> SEQ ID NO 123
<211> LENGTH: 13
<212> TYPE: PRT
<213> ORGANISM: Artificial
<220> FEATURE:
<223> OTHER INFORMATION: peptoid
<220> FEATURE:
<221> NAME/KEY: MISC_FEATURE
<222> LOCATION: (6)..(6)
<223> OTHER INFORMATION: Xaa = N-butylglycine

<400> SEQUENCE: 123

Lys Lys Arg Pro Lys Xaa Gly Gly Trp Asn Thr Gly Gly
1               5                   10

<210> SEQ ID NO 124
<211> LENGTH: 13
<212> TYPE: PRT
<213> ORGANISM: Artificial
<220> FEATURE:
<223> OTHER INFORMATION: peptoid
<220> FEATURE:
<221> NAME/KEY: MISC_FEATURE
<222> LOCATION: (6)..(6)
<223> OTHER INFORMATION: Xaa = N-(3,5-dimethoxybenzyl)glycine

<400> SEQUENCE: 124

Lys Lys Arg Pro Lys Xaa Gly Gly Trp Asn Thr Gly Gly
1               5                   10

<210> SEQ ID NO 125
<211> LENGTH: 13
<212> TYPE: PRT
<213> ORGANISM: Artificial
<220> FEATURE:
<223> OTHER INFORMATION: peptoid
<220> FEATURE:
<221> NAME/KEY: MISC_FEATURE
<222> LOCATION: (6)..(6)
<223> OTHER INFORMATION: Xaa = N-(isopropyl)glycine

<400> SEQUENCE: 125

Lys Lys Arg Pro Lys Xaa Gly Gly Trp Asn Thr Gly Gly
1               5                   10
```

```
<210> SEQ ID NO 126
<211> LENGTH: 13
<212> TYPE: PRT
<213> ORGANISM: Artificial
<220> FEATURE:
<223> OTHER INFORMATION: peptoid
<220> FEATURE:
<221> NAME/KEY: MISC_FEATURE
<222> LOCATION: (6)..(6)
<223> OTHER INFORMATION: Xaa = N-(cyclopropylmethyl)glycine

<400> SEQUENCE: 126

Lys Lys Arg Pro Lys Xaa Gly Gly Trp Asn Thr Gly Gly
1               5                   10

<210> SEQ ID NO 127
<211> LENGTH: 17
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Gly may be present or absent

<400> SEQUENCE: 127

Gly Gly Gly Lys Lys Arg Pro Lys Pro Gly Gly Gly Trp Asn Thr Gly
1               5                   10                  15

Gly

<210> SEQ ID NO 128
<211> LENGTH: 39
<212> TYPE: PRT
<213> ORGANISM: Artificial
<220> FEATURE:
<223> OTHER INFORMATION: peptide

<400> SEQUENCE: 128

Gln Trp Asn Lys Pro Ser Lys Pro Lys Thr Asn Gly Gly Gly Gln Trp
1               5                   10                  15

Asn Lys Pro Ser Lys Pro Lys Thr Asn Gly Gly Gly Gln Trp Asn Lys
            20                  25                  30

Pro Ser Lys Pro Lys Thr Asn
            35

<210> SEQ ID NO 129
<211> LENGTH: 11
<212> TYPE: PRT
<213> ORGANISM: Artificial
<220> FEATURE:
<223> OTHER INFORMATION: peptoid
<220> FEATURE:
<221> NAME/KEY: MISC_FEATURE
<222> LOCATION: (5)..(5)
<223> OTHER INFORMATION: Xaa = N-(cyclopropylmethyl)glycine
<220> FEATURE:
<221> NAME/KEY: MISC_FEATURE
<222> LOCATION: (8)..(8)
<223> OTHER INFORMATION: Xaa = N-(cyclopropylmethyl)glycine

<400> SEQUENCE: 129

Gln Trp Asn Lys Xaa Ser Lys Xaa Lys Thr Asn
1               5                   10

<210> SEQ ID NO 130
```

```
<210> SEQ ID NO 131
<211> LENGTH: 11
<212> TYPE: PRT
<213> ORGANISM: Artificial
<220> FEATURE:
<223> OTHER INFORMATION: peptoid
<220> FEATURE:
<221> NAME/KEY: MISC_FEATURE
<222> LOCATION: (5)..(5)
<223> OTHER INFORMATION: Xaa = N-(cyclopropylmethyl)glycine
<220> FEATURE:
<221> NAME/KEY: MISC_FEATURE
<222> LOCATION: (8)..(8)
<223> OTHER INFORMATION: Xaa = N-(3,5-dimethoxybenzyl)glycine

<400> SEQUENCE: 130

Gln Trp Asn Lys Xaa Ser Lys Xaa Lys Thr Asn
1               5                   10

<210> SEQ ID NO 131
<211> LENGTH: 11
<212> TYPE: PRT
<213> ORGANISM: Artificial
<220> FEATURE:
<223> OTHER INFORMATION: peptoid
<220> FEATURE:
<221> NAME/KEY: MISC_FEATURE
<222> LOCATION: (5)..(5)
<223> OTHER INFORMATION: Xaa = N-(cyclopropylmethyl)glycine
<220> FEATURE:
<221> NAME/KEY: MISC_FEATURE
<222> LOCATION: (8)..(8)
<223> OTHER INFORMATION: Xaa = N-butylglycine

<400> SEQUENCE: 131

Gln Trp Asn Lys Xaa Ser Lys Xaa Lys Thr Asn
1               5                   10

<210> SEQ ID NO 132
<211> LENGTH: 11
<212> TYPE: PRT
<213> ORGANISM: Artificial
<220> FEATURE:
<223> OTHER INFORMATION: peptoid
<220> FEATURE:
<221> NAME/KEY: MISC_FEATURE
<222> LOCATION: (5)..(5)
<223> OTHER INFORMATION: Xaa = N-(isopropyl)glycine
<220> FEATURE:
<221> NAME/KEY: MISC_FEATURE
<222> LOCATION: (8)..(8)
<223> OTHER INFORMATION: Xaa = N-(cyclopropylmethyl)glycine

<400> SEQUENCE: 132

Gln Trp Asn Lys Xaa Ser Lys Xaa Lys Thr Asn
1               5                   10
```